(12) United States Patent
Kodama et al.

(10) Patent No.: US 11,464,885 B2
(45) Date of Patent: Oct. 11, 2022

(54) ULTRAVIOLET LIGHT IRRADIATION DEVICE

(71) Applicant: ASAHI KASEI KABUSHIKI KAISHA, Tokyo (JP)

(72) Inventors: Atsushi Kodama, Tokyo (JP); Sumire Jinno, Tokyo (JP); Ryosuke Baba, Tokyo (JP); Naoto Yabuki, Tokyo (JP); Naoto Ito, Tokyo (JP); Hiroyuki Kishi, Tokyo (JP); Sho Sugiyama, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 131 days.

(21) Appl. No.: 16/382,501

(22) Filed: Apr. 12, 2019

(65) Prior Publication Data

US 2019/0321505 A1     Oct. 24, 2019

(30) Foreign Application Priority Data

Apr. 20, 2018 (JP) .............................. JP2018-081804
Apr. 20, 2018 (JP) .............................. JP2018-081805

(Continued)

(51) Int. Cl.
| | | |
|---|---|---|
| *A61L 9/20* | (2006.01) | |
| *C02F 1/32* | (2006.01) | |
| *A61L 2/10* | (2006.01) | |

(52) U.S. Cl.
CPC .................................. *A61L 9/20* (2013.01);
*A61L 2/10* (2013.01); *C02F 1/32* (2013.01);
*C02F 2201/3222* (2013.01)

(58) Field of Classification Search
CPC ...... A61L 9/20; A61L 2/10; C02F 1/32; C02F 2201/3222; C02F 1/325; C02F 2201/328; C02F 2201/3228
See application file for complete search history.

(56) References Cited

U.S. PATENT DOCUMENTS 3,840,051 A    10/1974 Koga et al.
9,321,665 B2 *  4/2016 Kolstad ..................... C02F 1/32
(Continued)

FOREIGN PATENT DOCUMENTS

EP    3388087 A1   10/2018
JP    H0361982 U    6/1991
(Continued)

OTHER PUBLICATIONS

Partial European search report dated Oct. 23, 2019 issued by the European Patent Office for the corresponding European Patent Application No. 19168925.6, 16 pages.
(Continued)

*Primary Examiner* — Regina M Yoo
(74) *Attorney, Agent, or Firm* — Morgan, Lewis & Bockius LLP

(57) ABSTRACT

A fluid sterilization module includes an inner cylinder forming a processing flow path extending in a longitudinal direction, a first chamber communicating with the processing flow path via an opening on one end side of the inner cylinder, an inflow portion allowing an object to flow in the first chamber, an outflow portion allowing the object having passed through the processing flow path to flow out from an other end side of the inner cylinder, and a light emitting element facing an opening on the other end side of the processing flow path and irradiating the object passing through the processing flow path with ultraviolet light along the longitudinal direction. The first chamber has an inner volume equal to or more than ⅔ of the cube of an equivalent inner diameter of the processing flow path and equal to or less than 3 times of inner volume of the processing flow path.

20 Claims, 37 Drawing Sheets

(30) Foreign Application Priority Data

Apr. 20, 2018 (JP) .............................. JP2018-081806
Apr. 20, 2018 (JP) .............................. JP2018-081807
Apr. 20, 2018 (JP) .............................. JP2018-081808

(56) References Cited

U.S. PATENT DOCUMENTS

| | | | |
|---|---|---|---|
| 10,472,260 B2 * | 11/2019 | Mochizuki | A61L 2/10 |
| 10,736,980 B2 | 8/2020 | Mochizuki et al. | |
| 2012/0318749 A1 | 12/2012 | Stokes et al. | |
| 2013/0119266 A1 | 5/2013 | Mondt et al. | |
| 2014/0240695 A1 | 8/2014 | Pagan et al. | |
| 2015/0314024 A1 | 11/2015 | Khan et al. | |
| 2016/0185622 A1 * | 6/2016 | Kolstad | C02F 9/00 |
| | | | 210/198.1 |
| 2017/0290943 A1 | 10/2017 | Stokes et al. | |
| 2018/0147314 A1 | 5/2018 | Stokes et al. | |
| 2018/0228928 A1 | 8/2018 | Ochi et al. | |
| 2018/0257953 A1 | 9/2018 | Mochizuki et al. | |
| 2019/0184045 A1 | 6/2019 | Mochizuki et al. | |
| 2019/0321505 A1 | 10/2019 | Kodama et al. | |

FOREIGN PATENT DOCUMENTS

| | | |
|---|---|---|
| JP | H5-20744 U | 3/1993 |
| JP | 2003-155721 A | 5/2003 |
| JP | 2008107330 A | 5/2008 |
| JP | 10-169621 A | 8/2010 |
| JP | 2012126769 A | 7/2012 |
| JP | 5432286 B2 | 12/2013 |
| JP | 2015174026 | 10/2015 |
| JP | 2016-501676 A | 1/2016 |
| JP | 2016-511138 A | 4/2016 |
| JP | 6080937 B1 | 1/2017 |
| JP | 1578940 S | 6/2017 |
| JP | 2017104230 A | 6/2017 |
| JP | 2018-26045 A | 2/2018 |
| JP | 201834101 | 3/2018 |
| JP | 2018202205 A | 12/2018 |
| JP | 201998055 | 6/2019 |
| WO | 2010055288 A1 | 5/2010 |
| WO | 2011014717 A2 | 2/2011 |
| WO | 2012014108 A1 | 2/2012 |
| WO | 2017/064950 A1 | 4/2017 |

OTHER PUBLICATIONS

European Search Report for European Application No. 20191293.8, dated Nov. 9, 2020, 4 pages.

Extended European Search Report for application No. 19168922.3, dated Jun. 2, 2020, 8 pages.

Tribology of Polymer Materials by Yoshinori Takeichi, Department of Mechanical Engineering, Toyohashi University of Technology (1-1,Hibarigaoka, Tempaku-cho, Toyohashi-shi, Aichi 441-8580, 12 pages (2014).

* cited by examiner

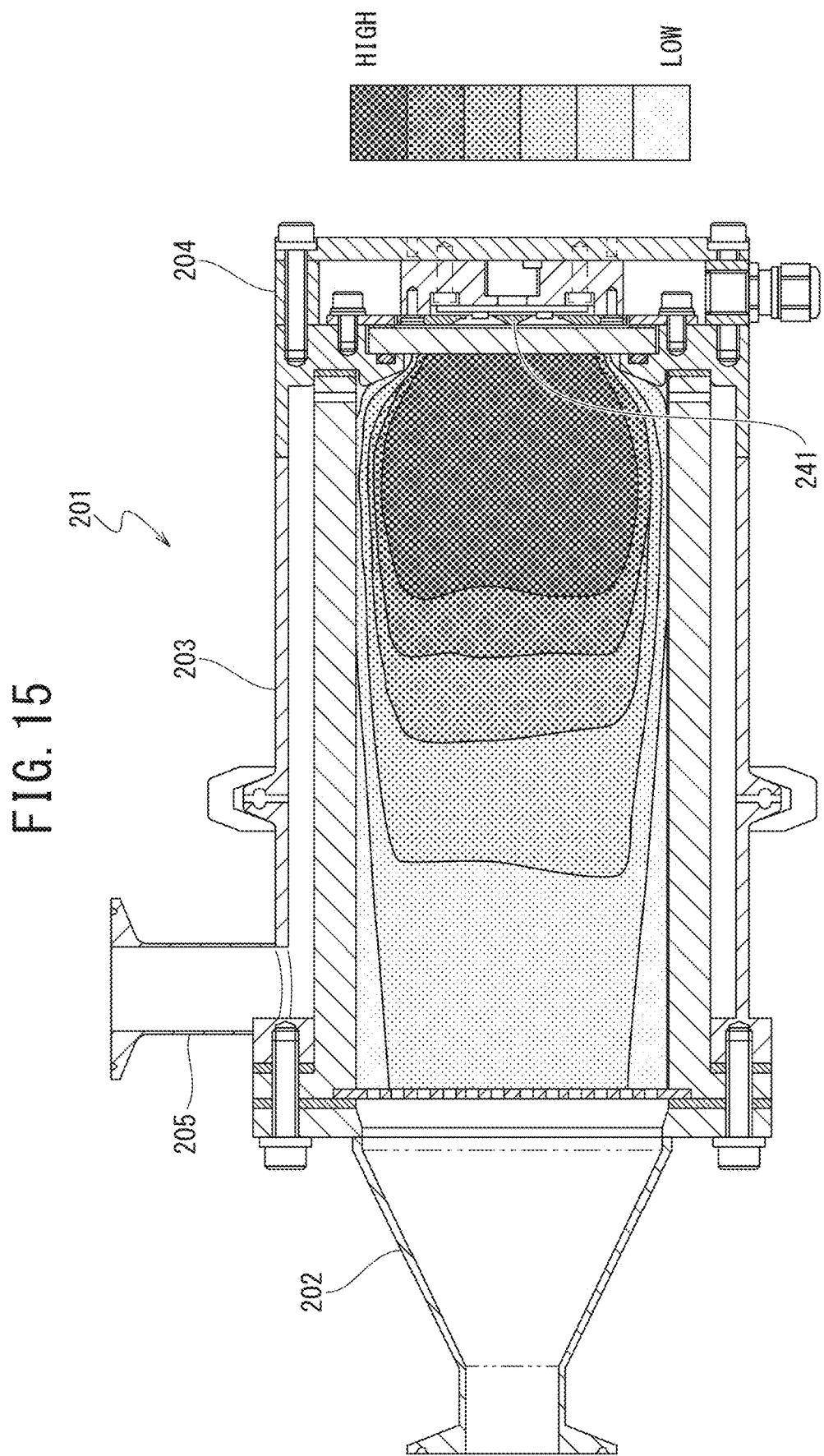

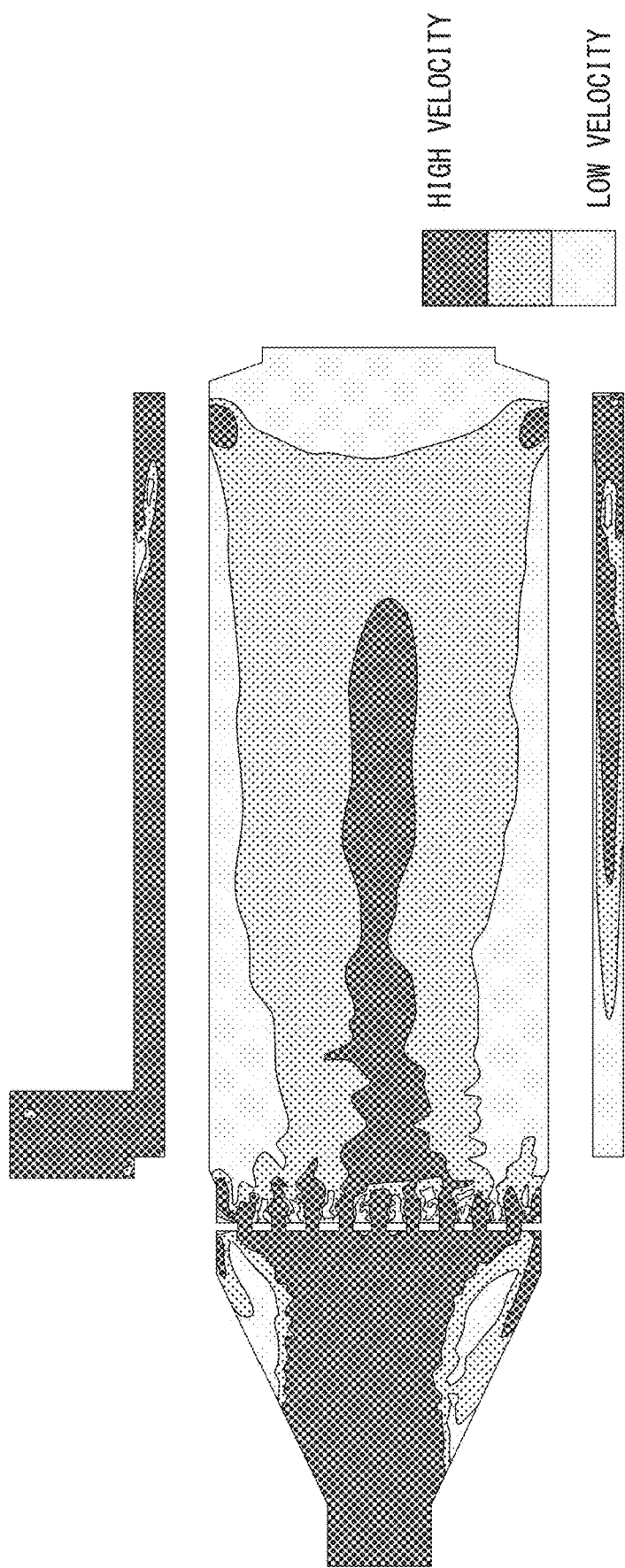

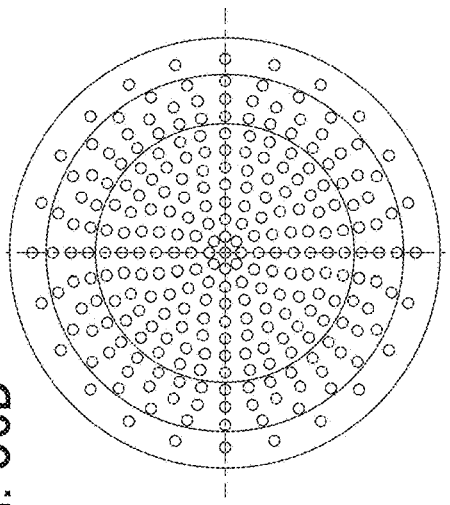
FIG. 36B
FLOW STRAIGHTENING PLATE 206-2
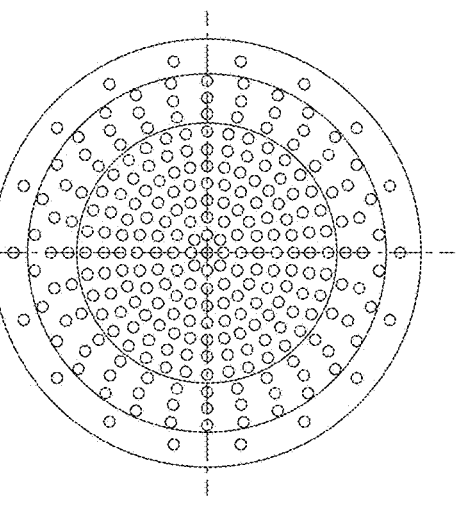
FIG. 36E
FLOW STRAIGHTENING PLATE 206-5
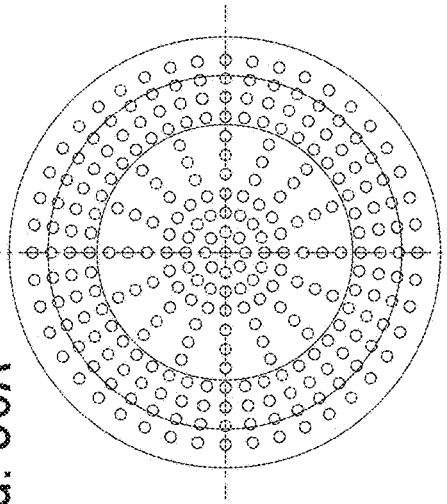
FIG. 36A
FLOW STRAIGHTENING PLATE 206-1
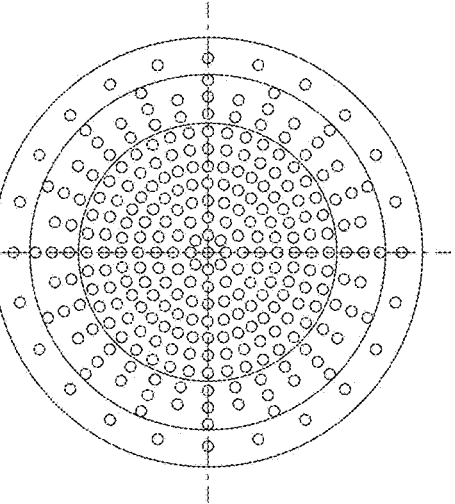
FIG. 36D
FLOW STRAIGHTENING PLATE 206-4
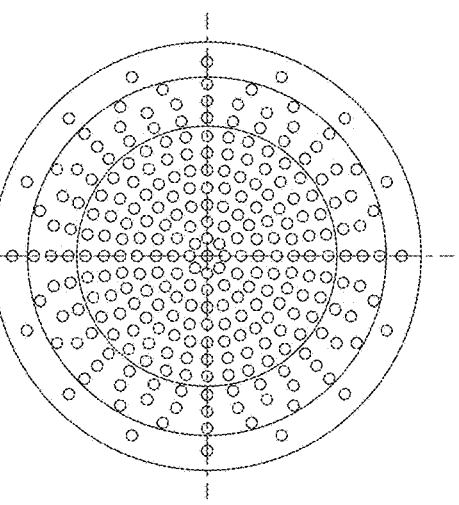
FIG. 36C
FLOW STRAIGHTENING PLATE 206-3
FIG. 36F
FLOW STRAIGHTENING PLATE 206-6

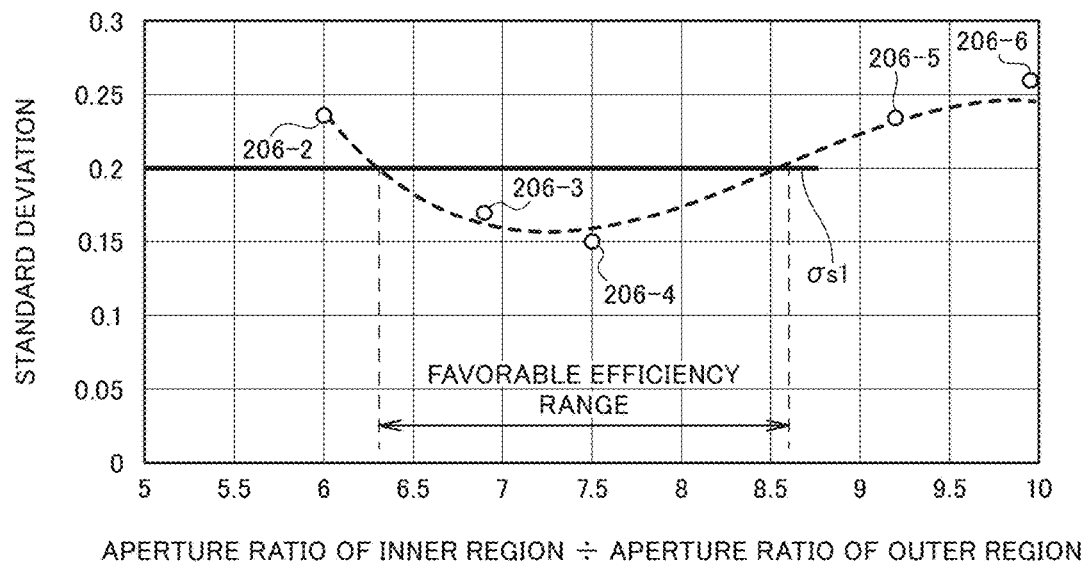
APERTURE RATIO OF INNER REGION ÷ APERTURE RATIO OF OUTER REGION
FIG. 39
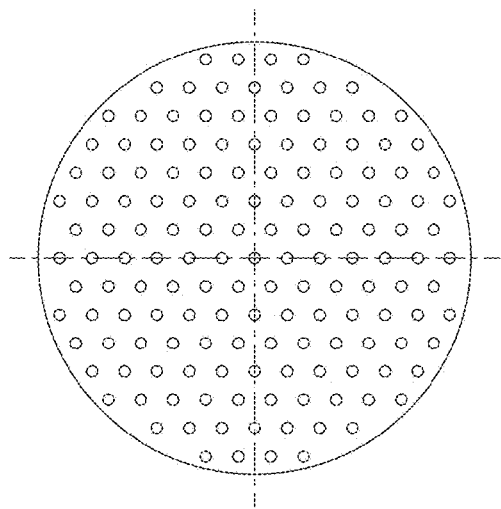
FLOW STRAIGHTENING PLATE 206-11
APERTURE RATIO OF FLOW
STRAIGHTENING PLATE 9.4%
NUMBER OF HOLES 151
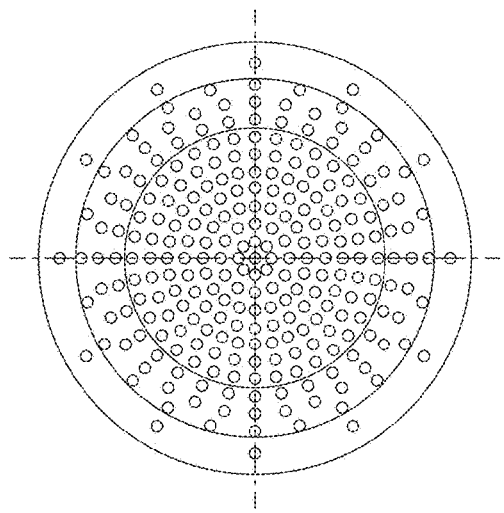
FLOW STRAIGHTENING PLATE 206-12
APERTURE RATIO OF FLOW
STRAIGHTENING PLATE 16.6%
NUMBER OF HOLES 265

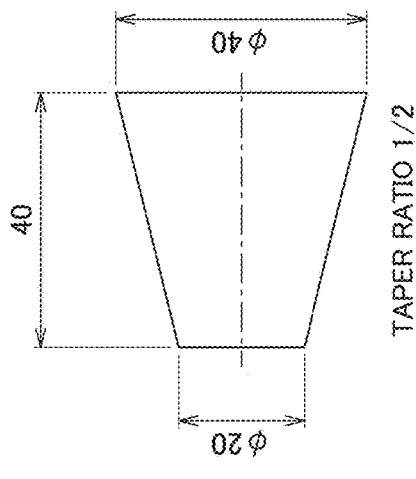
FIG. 41A TAPERED PORTION 222-1 TAPER RATIO 1/4
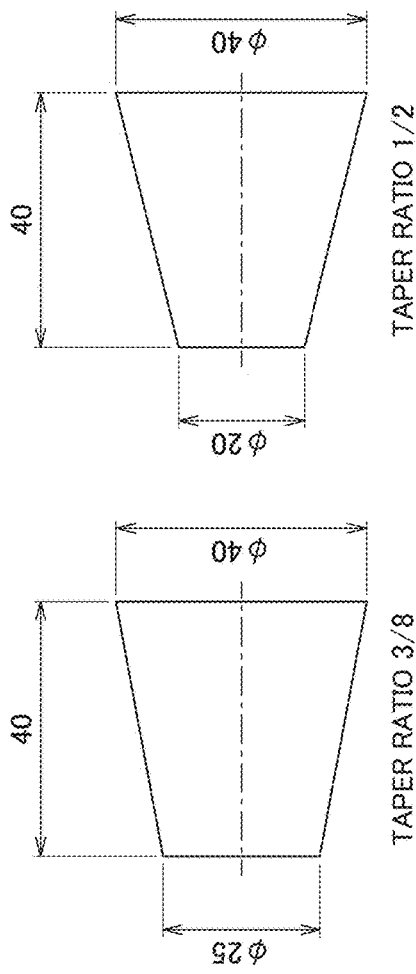
FIG. 41B TAPERED PORTION 222-2 TAPER RATIO 3/8
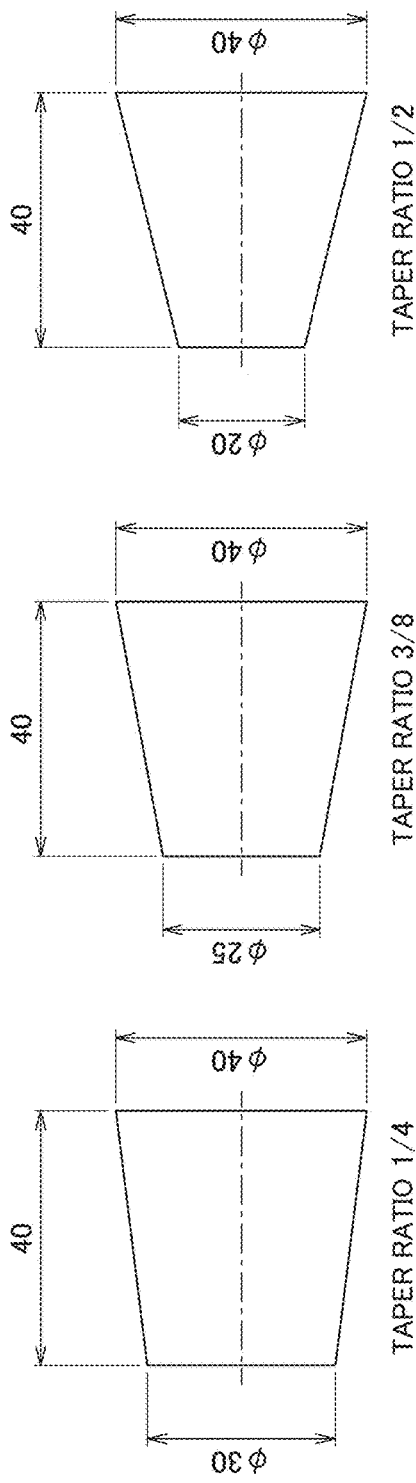
FIG. 41C TAPERED PORTION 222-3 TAPER RATIO 1/2
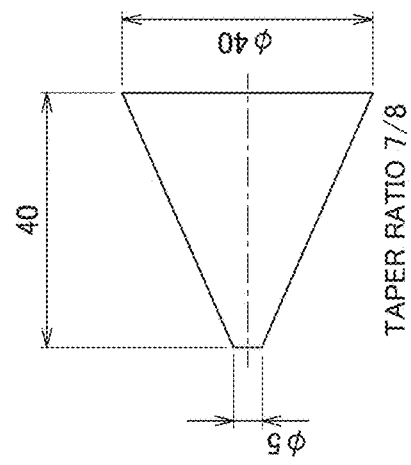
FIG. 41D TAPERED PORTION 222-4 TAPER RATIO 3/4
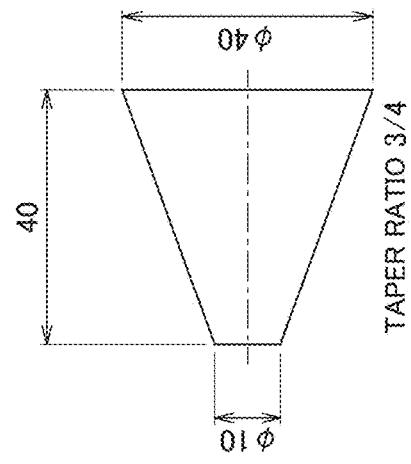
FIG. 41E TAPERED PORTION 222-5 TAPER RATIO 7/8

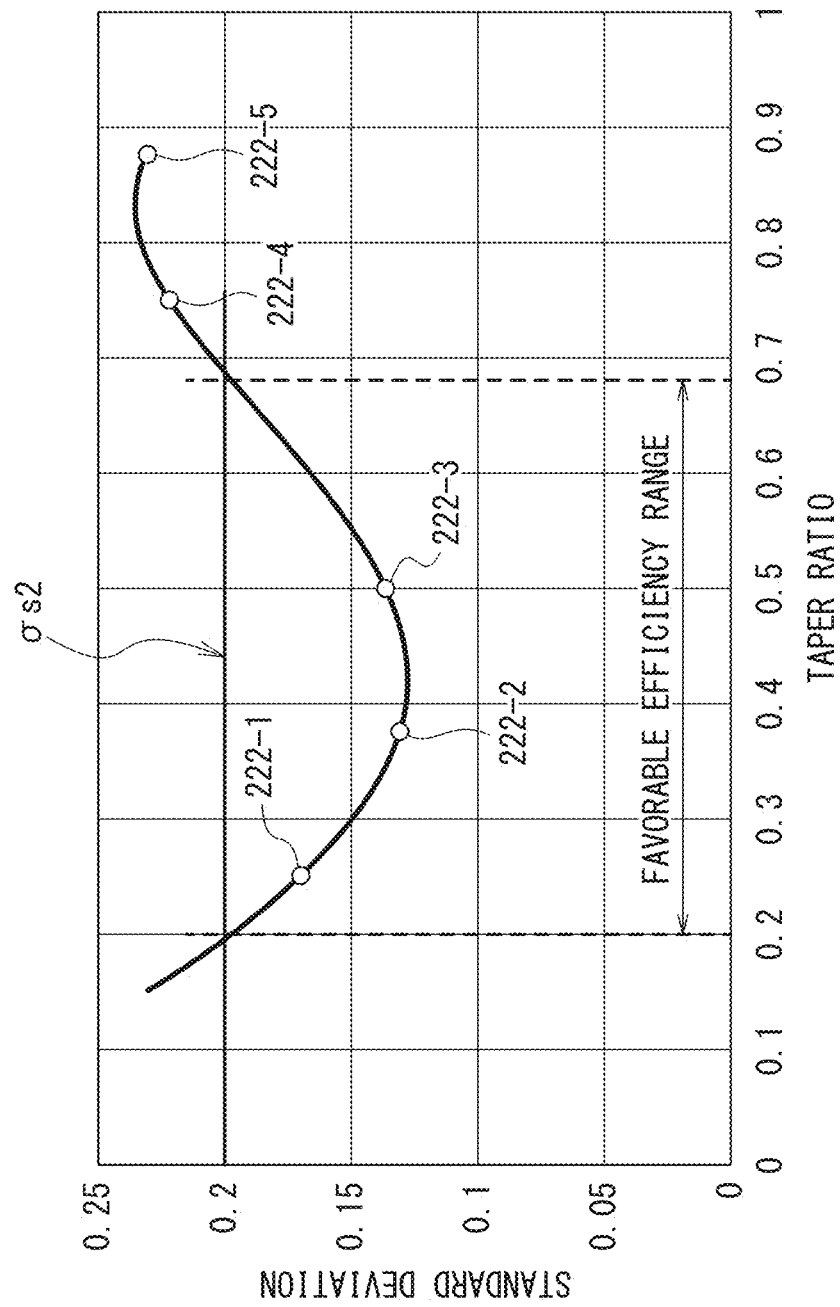

FIG. 44A
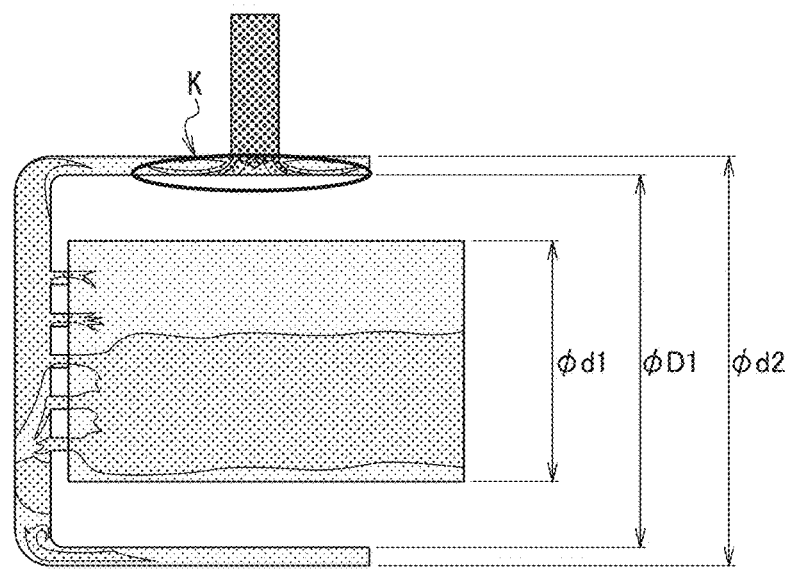
FLUID STERILIZATION
MODULE 1-1
FIG. 44B
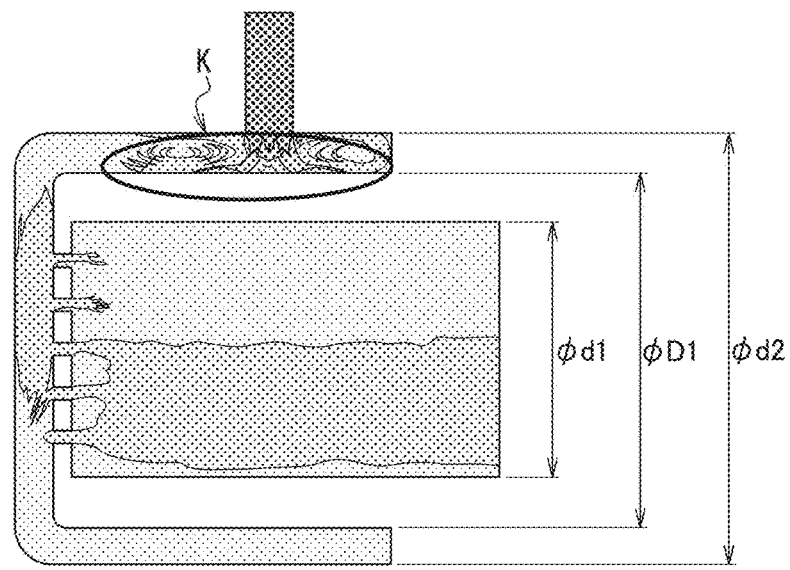
FLUID STERILIZATION
MODULE 1-2
FIG. 44C
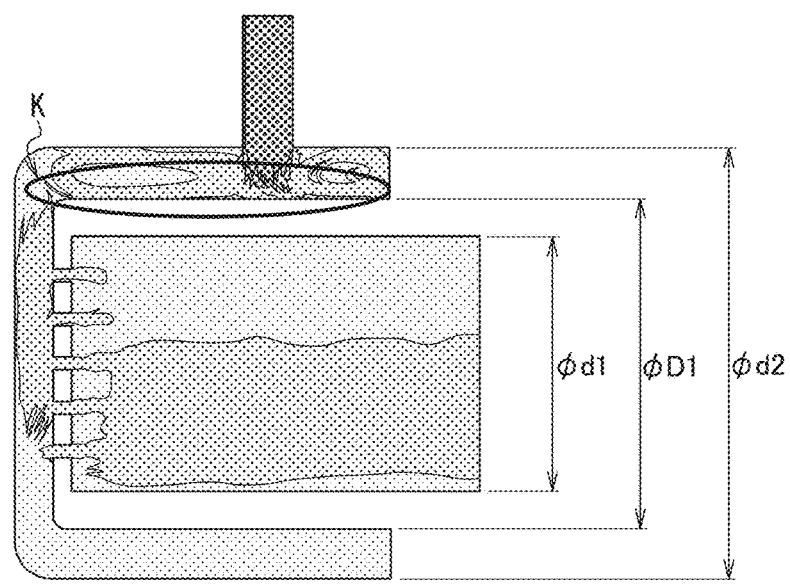
FLUID STERILIZATION
MODULE 1-3
FLOW
VELOCITY
HIGH ←→ LOW
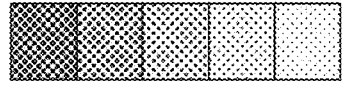

ULTRAVIOLET LIGHT IRRADIATION DEVICE

TECHNICAL FIELD

The present invention relates to ultraviolet light irradiation devices.

BACKGROUND ART

Since ultraviolet light has sterilization capability, there have been proposed devices for irradiating a fluid such as water with ultraviolet light to continuously sterilize the fluid.

Such devices conventionally use bulb (s) such as a mercury lamp or a xenon lamp as an ultraviolet light source. Additionally, those such as fluid sterilization devices have also been proposed that use, as an ultraviolet light source, light emitting diode(s) (LEDs) capable of applying light with sterilizable wavelength to apply ultraviolet light longitudinally toward a fluid flowing through the inside of a flow path tube forming a flow path extending longitudinally.

In addition, to improve sterilization efficiency in a fluid sterilization module using LED(s) as an ultraviolet light source as mentioned above, it is preferable to form a flow velocity distribution matching with a light flux distribution of ultraviolet light in a sterilization region. To this end, a method has been proposed in which inlet/outlet ports are provided to use as the inlet or outlet of a flow path, and flow straightening chambers each including a facing member facing each end of a flow path tube are arranged so as to surround the ends of the flow path tube. A fluid flown into one of the flow straightening chambers from one of the inlet/output ports or flown out from an other flow straightening chamber is allowed to flow into or flow out from the flow path tube via gaps formed between the facing members and the ends, whereby flow velocity of the fluid is adjusted (e.g., see JP 6080937 B1).

SUMMARY

However, in the technology disclosed in JP 6080937 B1, when pressure loss is set to be large, i.e., the gaps are made small, a small dimensional error induces a velocity difference in the flow velocity since the flow velocity is adjusted by inflow or outflow via the gaps between the ends of the processing flow path and the facing members. This results in formation of a portion with high flow velocity where ultraviolet light irradiation dose is insufficient. If the pressure loss is set to be small, i.e., the gaps are made large to prevent the above problem, velocity difference due to inertia of fluid cannot be sufficiently reduced.

Accordingly, the present invention has been accomplished focusing on the unsolved problem of the conventional technology, and it is an object of the present invention to provide an ultraviolet light irradiation device capable of suppressing variation in ultraviolet light irradiation dose to be applied to a fluid flowing through a flow path, which is caused by a high flow velocity portion formed in the fluid flowing therethrough due to an assembly error.

According to an aspect of the present invention, there is provided an ultraviolet light irradiation device including: a cylindrical portion configured to form a cylindrical processing flow path extending in a longitudinal direction and include an opening at one end side of the cylindrical portion; a first chamber configured to cover the opening and communicate with the processing flow path via the opening; an inflow portion configured to allow an object to flow into the first chamber; an outflow portion configured to allow the object having passed through the processing flow path to flow out from an other end of the cylindrical portion; and a light emitting element provided at least on the one end side or the other end side of the cylindrical portion and configured to apply ultraviolet light to the object passing through the processing flow path, wherein the first chamber has an inner volume equal to or more than ⅔ of the cube of an equivalent inner diameter of the processing flow path and equal to or less than 3 times of inner volume of the processing flow path.

Herein, note that the equivalent inner diameter of the processing flow path refers to "(four times a cross-sectional area of the processing flow path)/(a cross-sectional peripheral length of the processing flow path)".

According to one aspect of the present invention, it is possible to suppress variation in ultraviolet light irradiation dose to be applied to a fluid flowing through a flow path, which is caused by a high flow velocity portion formed in the fluid flowing therethrough due to low assembly accuracy.

BRIEF DESCRIPTION OF DRAWINGS

FIG. 15 is an illustrative diagram for illustrating ultraviolet light intensity of a light source;

FIG. 16 is a distribution diagram illustrating one example of a flow velocity distribution in the fluid sterilization module according to the second embodiment;

FIGS. 36A to 36F illustrate one example of flow straightening plates assumed in flow velocity simulation using the fluid sterilization module according to the second embodiment;

FIG. 38 illustrates one example of correspondences between aperture ratios of flow straightening plates and standard deviations of ultraviolet light intensity ratios by flow velocity simulation using the fluid sterilization module according to the second embodiment;

FIG. 39 illustrates one example of correspondences between aperture ratios of flow straightening plates and pressure losses by flow velocity simulation using the fluid sterilization module according to the second embodiment;

FIGS. 41A to 41E illustrate one example of taper ratios assumed in flow velocity simulation using the fluid sterilization module according to the second embodiment;

FIG. 43 illustrates one example of correspondences between taper ratios, aperture ratios of flow straightening plates, and standard deviations of ultraviolet light intensity ratios by flow velocity simulation using the fluid sterilization module according to the second embodiment; and FIGS. 44A to 44C illustrate one example of flow velocity deviations in fluid sterilization modules by simulation using the fluid sterilization module according to the first embodiment.

DESCRIPTION OF EMBODIMENTS

Figure 1:
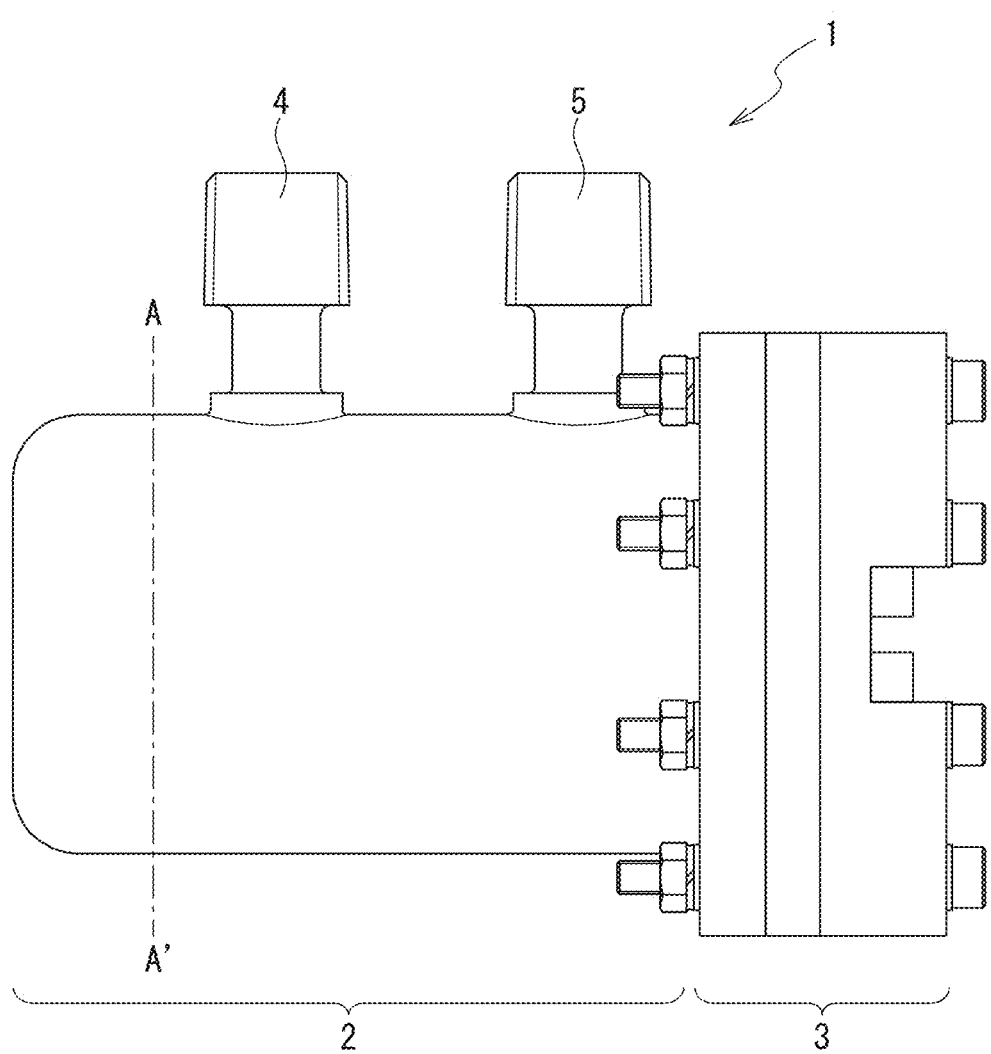
FIG. 1 is a diagram of an external appearance illustrating one example of a fluid sterilization module according to a first embodiment to which an ultraviolet light irradiation device according to the present invention is applied.

Next, referring to the drawings, an embodiment of the present invention will be described. In the description of the drawings, same or similar elements are denoted by the same or similar reference signs. The drawings are schematic and relations between thicknesses and two-dimensional dimensions, ratios between thicknesses of respective layers, and the like may be different from actual ones. The embodiments to be described below are intended to exemplify a device and a method for embodying the technical idea of the present invention, and the technical idea of the present invention does not limit materials, shapes, structures, arrangements, and the like of components to those described below. Various modifications may be made to the technical idea of the present invention within the technical scope defined by the claims.

First Embodiment

First, a first embodiment will be described.

FIG. 1 is a front view illustrating one example of a fluid sterilization module to which an ultraviolet light irradiation device according to the present invention is applied. Additionally, FIG. 2A is a longitudinal cross-sectional diagram of FIG. 1, and FIG. 2B is an end face diagram taken along line A-A' of FIG. 1.

A fluid sterilization module 1 includes a sterilization processing unit 2, a light emitting unit 3, an inflow portion 4, and an outflow portion 5, as illustrated in FIG. 1.

Figure 2A:
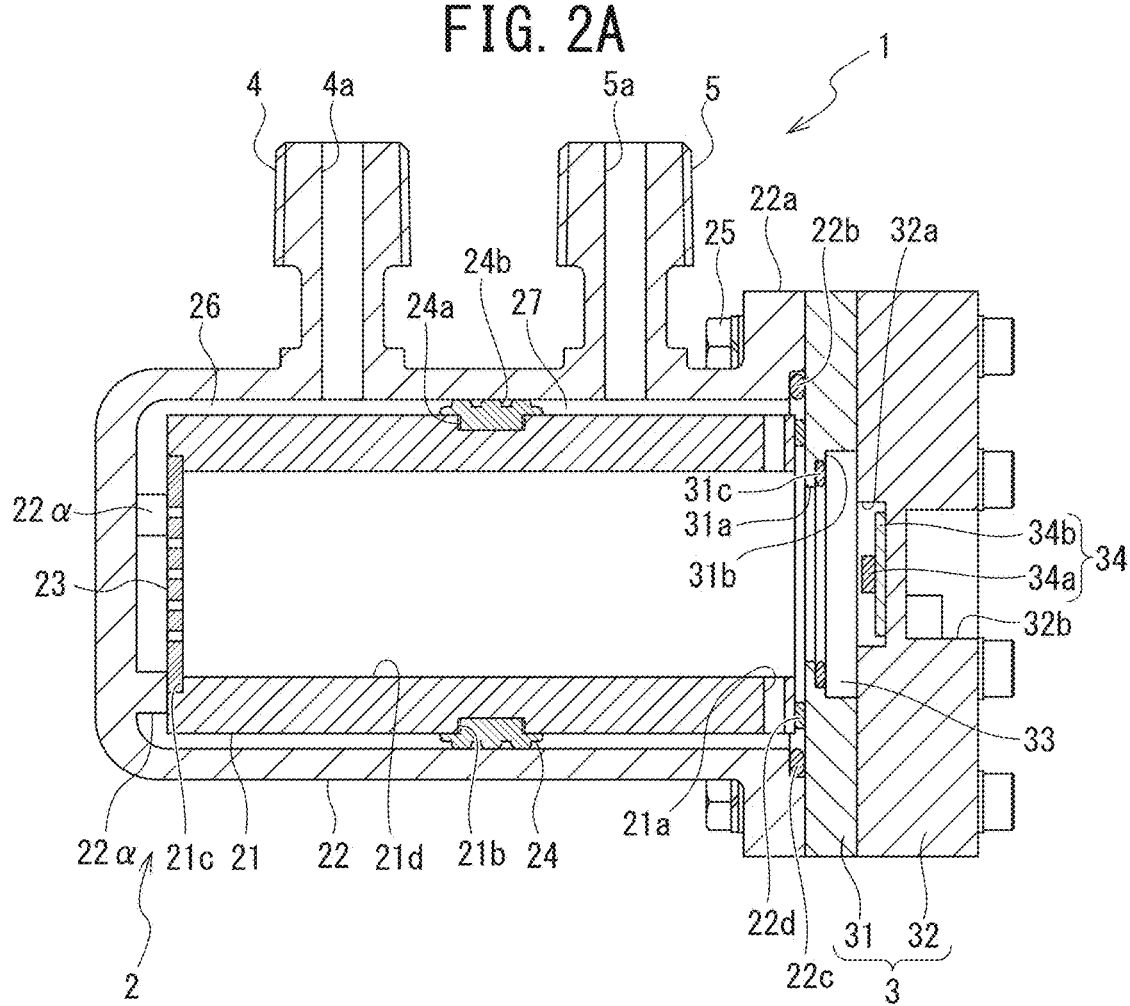
FIG. 2A is a longitudinal cross-sectional diagram of FIG. 1.
Figure 2B:
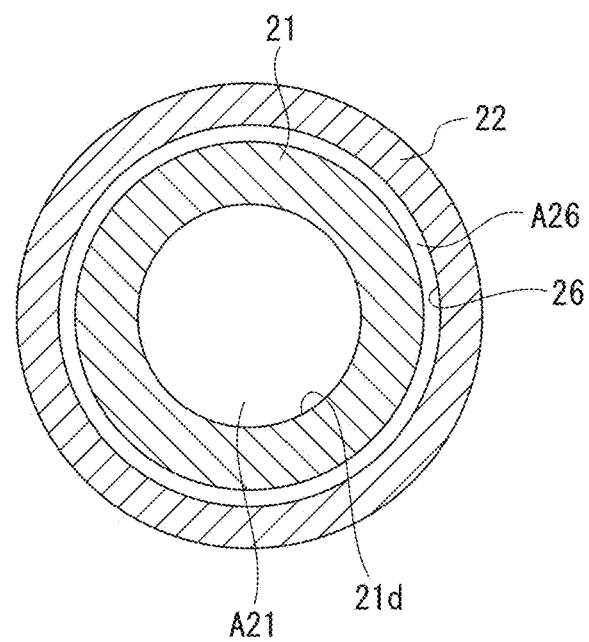
FIG. 2B is an end face diagram taken along line A-A' of FIG. 1.

As illustrated in FIG. 2A, the sterilization processing unit 2 includes an inner cylinder (a cylindrical portion) 21, a case portion 22 housing the inner cylinder 21, a disc-shaped plate (a plate configured to cover an opening) 23 fixed to the opening on one end side of the inner cylinder 21 and configured to straighten the flow of a fluid to be flown into the inner cylinder 21, and a member 24 arranged between the inner cylinder 21 and the case portion 22 to partition a gap between the inner cylinder 21 and the case portion 22.

The inner cylinder 21 is formed into a cylindrical shape having both open ends, and preferably has a thickness of from 1 mm to 20 mm. Additionally, the inner cylinder 21 is formed using an ultraviolet light reflecting material whose diffuse transmittance is from 1%/mm to 20%/mm and whose total reflectance in an ultraviolet light region is from 80%/mm to 99%/mm. Preferably, a sum of the diffuse transmittance and the total reflectance in the ultraviolet light region is 90%/mm or more. Examples of the ultraviolet light reflecting material to be applied to the inner cylinder 21 include at least any one of polytetrafluoroethylene (PTFE), silicon resins, quartz glasses containing bubbles having a size of from 0.05 μm to 10 μm thereinside, partially crystallized quartz glasses containing crystalline particles having a size of from 0.05 μm to 10 μm thereinside, crystalline particulate alumina sintered bodies having a size of from 0.05 μm to 10 μm, and crystalline particulate mullite sintered bodies having a size of from 0.05 μm to 10 μm.

Herein, in the case of using a diffusive reflecting material as the inner cylinder 21, assuming that there is no absorption of ultraviolet light by the material itself, at least a part of irradiation light applied by the light emitting unit 3 provided on the one end side of the inner cylinder 21 is set to be transmitted up to the other end side of the inner cylinder 21. When the transmittance in this case is higher than 20%/mm, a very thick material is needed for the thickness of the inner cylinder 21 in order to increase an effective ultraviolet light reflection amount. Due to this, the entire fluid sterilization module 1 becomes large in size, or it becomes difficult to appropriately design a flow path, as well as it becomes necessary to control reflection from a deep layer, which makes optical design difficult. High scatter optical density and low transmittance are generally desirable. However, when the material is non-porous, density difference in the inside of the material including crystalline and non-crystalline portions and the like becomes a scatterer, so that it is difficult to set the transmittance to be lower than 1%/mm. When the material is porous, it is possible to have a structure with a transmittance of less than 1%/mm. However, since a processing flow path 21d, which will be described later, contacts with an object to be sterilized (hereinafter also referred to simply as "object"), there will be provided a minute hole structure that results in a hotbed for bacteria. Thus, such a material is not suitable as the component of the inner cylinder 21.

In addition, when the total transmittance in the ultraviolet light region is 80%/mm or less, multiple reflection effect of effective ultraviolet light cannot be obtained. Higher total transmittance is more desirable. However, in the case of a non-porous material, density difference in the inside of the material including crystal and non-crystal portions and the like becomes a scatterer, so that it is difficult to set the total reflectance to be higher than 99%/mm. In the case of a porous material, it is possible to have a structure with a total reflectance of more than 99%/mm. However, since the processing flow path 21d contacts with the object, there will be provided a minute hole structure that results in a hotbed for bacteria. Thus, such a material is not suitable as the component of the inner cylinder 21.

Furthermore, materials whose sum of the diffuse transmittance and the total reflectance in the ultraviolet light region is 90%/mm or less, i.e., whose amount of energy absorbed thereinside is 10% or more cannot have multiple reflection effects of effective ultraviolet light, and thus are not suitable as the component of the processing flow path 21d.

Note that the diffuse transmittance is measured using plate-shaped samples obtained by cutting an ultraviolet light reflecting material into slices. Specifically, for example, when measuring the diffuse transmittance of PTFE as an ultraviolet light reflecting material, the following steps will be performed.

Specifically, since PTFE is a material having diffusivity, it is difficult to appropriately measure the diffusive transmittance by measurement of transmittance using ordinary linear light. Thus, the diffuse transmittance is measured by using an integrating sphere. The measurement of the diffuse transmittance using an integrating sphere may be performed using a spectrophotometer or the like commonly used in measuring diffuse transmittances of suspended substances, for example, as illustrated in FIG. 3.

Figure 3:
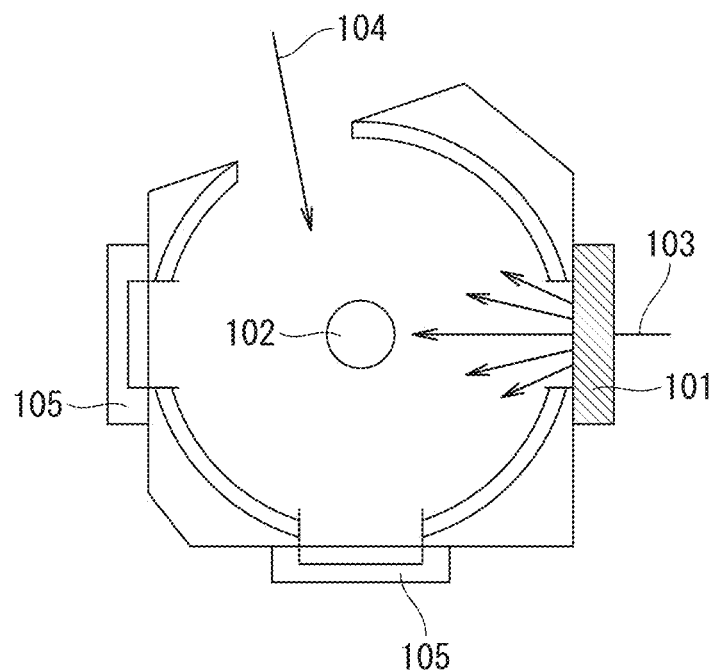
FIG. 3 illustrates one example of a device for use in measurement of diffuse transmittance.

Note that, in FIG. 3, reference sign 101 denotes a plate-shaped sample, 102 denotes a detector, 103 denotes a sample beam, 104 denotes a reference beam, and 105 denotes a white reference plate.

Returning to FIGS. 2A and 2B, preferably, the inner cylinder 21 is formed using a material such that an outer peripheral surface of the inner cylinder 21 has a static friction coefficient smaller than a static friction coefficient of an inner peripheral surface of the case portion 22. In other words, in a first chamber 26, which will be described later, formed by a gap between the inner cylinder 21 and the case portion 22, preferably, the static friction coefficient of the outer peripheral surface of the inner cylinder 21 forming a wall surface on an inner peripheral side of the first chamber 26 is smaller than the static friction coefficient of the inner peripheral surface of the case portion 22 forming a wall surface on an outer peripheral side of the first chamber 26. With this structure, in a situation where biofilm formation occurs, biofilm will be formed on the wall surface on the outer peripheral side of the first chamber 26 earlier than on the wall surface on the inner peripheral surface of the first chamber 26. The presence of the biofilm adherent on the wall surface on the outer peripheral side of the first chamber 26, i.e., on the inner peripheral surface of the case 22 can be confirmed by a shadow formed when a beam of a flashlight or the like is applied from outside. Thus, biofilm formation in the first chamber 26 can be easily detected, and also, biofilm formation can be detected upon formation of biofilm on the wall surface on the outer peripheral side of the first chamber 26, i.e., on the inner peripheral surface side of the case portion 22 prior to biofilm formation on the entire first chamber 26. This can suppress the occurrence of risks due to biofilm.

Note that to further reduce risks due to biofilm, the static friction coefficient of the outer peripheral surface of the inner cylinder 21 is preferably equal to or less than ½ of the static friction coefficient of the inner peripheral surface of the case portion 22. Additionally, the static friction coefficient of the outer peripheral surface of the inner cylinder 21 is more preferably equal to or less than ¹⁄₁₀ of the static friction coefficient of the inner peripheral surface of the case portion 22.

Tables 1 and 2 depict friction coefficients of resins, in which Table 1 depicts friction coefficients of typical resins, and Table 2 depicts static friction coefficients and dynamic friction coefficients of fluoro resins.

TABLE 1

| Type of material | Polymer/polymer | Polymer/Steel | Steel/polymer |
|---|---|---|---|
| PTFE | 0.04 | 0.04 | 0.10 |
| Polyethylene | 0.10 | 0.15 | 0.2 |
| Polystyrene | 0.5 | 0.3 | 0.35 |
| Polymethyl methacrylate | 0.8 | 0.5 | 0.45 |

TABLE 2

| Type of material | Friction coefficients | |
| --- | --- | --- |
| Fluororesin | Static | Dynamic |
| PTFE | 0.02-0.03 | 0.1-0.2 |
| PFA | 0.05-0.06 | 0.2 |
| FEP | 0.05-0.06 | 0.3-0.4 |
| PCTFE | 0.23-0.36 | 0.15-0.34 |
| ETFE | 0.40 | 0.4 |
| PVDF | 0.3 | 0.14-0.17 |
| PVF | 0.3 | 0.4 |

Returning to FIG. 2A, in positions on the inner cylinder 21 close to an end of the light emitting unit 3 side, for example, at six places spaced apart from each other by 60 degrees in a circumferential direction is formed a communication port 21a orienting in a radial direction and penetrating through the inner cylinder 21. Note that the arrangement positions and number of arrangement of the communication ports 21a are not limited thereto.

The shape of each communication port 21a is preferably circular in cross section from the viewpoint of mechanical processing. The cross-sectional shape of the communication portion 21a is not limited to a circular shape, and can be any optional shape. In addition, the communication port 21a has a diameter of preferably from 1/100 to 1/4, and more preferably from 1/20 to 1/5, of a diameter of the processing flow path 21d.

The arrangement position of the communication port 21a is preferably a position where the distance between a center position of an opening of the communication port 21a and the end of the processing flow path 21d on the light emitting unit 3 side is equal to or more than 1/20 of the diameter of the processing flow path 21d and equal to or less than the diameter, which is a position slightly shifted from the light emitting unit 3 toward the opposite end of the processing flow path 21d with respect to the light emitting unit 3. More preferably, the arrangement position of the communication port 21a is a position slightly shifted toward the opposite end of the processing flow path 21d where the distance is from 1/10 to 1/4 of the diameter of the processing flow path 21d.

On an outer peripheral surface of the inner cylinder 21 at a center portion in a direction in which the inner cylinder 21 extends is formed a groove 21b to be fitted with a member 24. The groove 21b has, for example, a rectangular cross-sectional shape.

On an inner peripheral surface of the end of the inner cylinder 21 on the side opposite to the light emitting unit 3 is formed a step portion 21c to be fitted with a plate 23. Then, a hollow portion of the inner cylinder 21 forms the processing flow path 21d.

Note that, in the processing flow path 21d, from the viewpoint of suppressing variation in the flow velocity of an object in the processing flow path 21d, the amount of change of a main cross-sectional area from a most upstream portion of the processing flow path 21d, i.e., from an end of the plate 23 side on the inner peripheral surface of the inner cylinder 21 to the end of the light emitting unit 3 side on the inner peripheral surface of the inner cylinder 21 is preferably 5% or less. Additionally, the processing flow path 21d does not have to be cylindrical.

The case portion 22 is formed using, for example, polyolefin, and specifically, polypropylene or polyethylene, and has a cylindrical shape having one closed end and the other open end, whose cross-sectional shape is circular. On an outer peripheral surface of the open end of the case portion 22 is formed a flange portion 22a. In addition, on an inner peripheral surface of the open end of the case portion 22 is formed a step portion 22b.

At the closed end of the case portion 22 on a side opposite to the open end is formed protruding portions 22a protruding toward an inside of the case portion 22. The protruding portions 22a are provided at three places spaced apart from each other by, for example, 120 degrees in the circumferential direction. Note that the arrangement positions and number of arrangement of the protruding portions 22a are not limited thereto, and, in short, can be optional as long as the plate 23 can be fixed, as will be described later.

On an outer peripheral surface close to the closed end of the case portion 22 is formed the inflow portion 4 having a cylindrical hollow portion thereinside and formed integrally with the case portion 22. On an outer peripheral surface close to the open end of the case portion 22 is formed the outflow portion 5 having a cylindrical hollow portion thereinside and formed integrally with the case portion 22. An opening of the hollow portion of the inflow portion 4 is used as an inflow port 4a, and an opening of the hollow portion of the outflow portion 5 is used as an outflow port 5a.

Preferably, the inflow portion 4 and the outflow portion 5 are formed such that a direction in which the object flows through each hollow portion and a longitudinal direction of the case portion 22 are orthogonal to each other.

The inflow portion 4 is formed at a position where a distance between an end of an outer peripheral surface of the inner cylinder 21 on the step portion 21c side and the inflow portion 4 is close to an end of the inner cylinder 21 on the communication port 21a side by a distance equal to or more than an inflow port equivalent radius of the inflow port 4a and equal to or less than 2/3 of a processing flow path length of the processing flow path 21d.

The outflow portion 5 is formed at a position where a distance thereof from the communication port 21a is close to the end of the inner cylinder 21 on the step portion 21c side by a distance equal to or more than an outflow port equivalent radius of the outflow port 5a and equal to or less than 2/3 of the processing flow path length.

Forming each of the inflow portion 4 and the outflow portion 5 within such a range can suppress the occurrence of an extremely high flow velocity portion in the processing flow path 21d.

Note that the arrangement position of the inflow portion 4 is more preferably a position where the distance between the end of the outer peripheral surface of the inner cylinder 21 on the step portion 21c side and the inflow portion 4 is close to the end of the inner cylinder 21 on the communication port 21a side by a distance equal to or more than 1/2 of an equivalent diameter of the processing flow path 21d (hereinafter also referred to as "processing flow path equivalent inner diameter) and equal to or less than 2/3 of the processing flow path length, and still more preferably a position where the distance therebetween is close to the end of the inner cylinder 21 on the communication port 21a side by a distance equal to or more than 3/4 of the processing flow path equivalent inner diameter and equal to or less than 2/3 of the processing flow path length.

Similarly, the arrangement position of the outflow portion 5 is preferably a position where a distance thereof from the communication port 21a is close to the end on the step portion 21c side by a distance equal to or more than 1/2 of the processing flow path equivalent inner diameter and equal to or less than 2/3 of the processing flow path length, and more preferably a position where the distance therefrom is close to the end on the step portion 21c side by a distance equal to or more than ¾ of the processing flow path equivalent inner diameter and equal to or less than ⅔ of the processing flow path length.

Note that when the arrangement positions of the inflow portion 4 and the outflow portion 5 are positions exceeding ⅔ of the processing flow path length, design flexibility for arranging the inflow portion 4 and the outflow portion 5 is reduced, so that the range of equal to or less than ⅔ of the processing flow path length is preferable.

Figure 4:
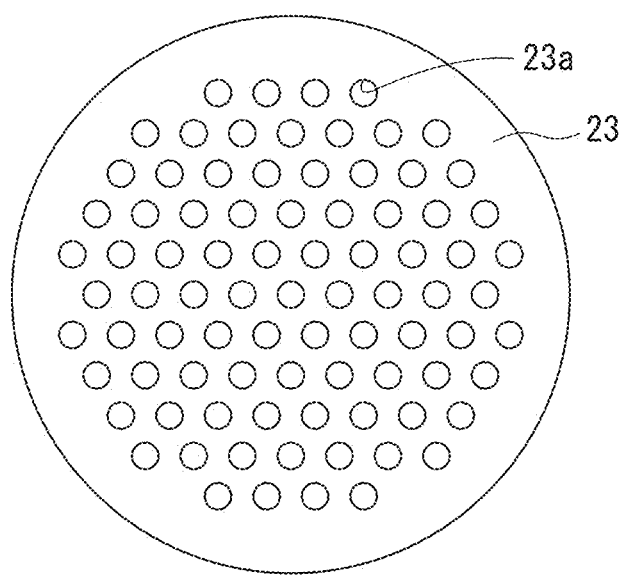
FIG. 4 is a plan view illustrating one example of a flow straightening plate.

The plate 23 is formed using an ultraviolet light reflecting material such as PTFE. The plate 23 includes a plurality of opening holes 23a penetrating between front and back surfaces, as illustrated in a plan view of FIG. 4, and has an aperture ratio of from 0.05 to 0.8. Additionally, each opening hole 23a has an equivalent diameter set to be equal to or more than 0.5 mm and equal to or less than ⅓ of the processing flow path equivalent inner diameter of the processing flow path 21d.

Setting the aperture ratio to from 0.05 to 0.8 can provide a further flow straightening effect, as compared with when not providing the first chamber 26 and a second chamber 27, which will be described later. In other words, variation in the flow velocity of the object in the processing flow path 21d can be suppressed. The aperture ratio is preferably from 0.05 to 0.6, and more preferably from 0.05 to 0.35. Note that when the aperture ratio is below 0.05, the maximum processing flow rate decreases with respect to the size of the processing flow path 21d, so that the aperture ratio is preferably 0.05 or more.

Note that herein, while the plate 23 is provided in order to control the flow of the object to be flown into the processing flow path 21d from the first chamber 26, the plate 23 is illustrative only, and it is possible to provide a flow straightening mechanism that can straighten the flow. Alternatively, the plate 23, i.e., the flow straightening mechanism does not have to be provided if a required sterilization effect can be obtained.

Returning to FIGS. 2A and 2B, the member 24 is formed using, for example, a fluorine rubber such as VITON (registered trademark). The member 24 is formed into an annular shape, and on an inner peripheral surface side thereof is formed a protruding portion 24a to be fitted with the groove 21b formed on the inner cylinder 21. On an outer peripheral surface side of the member 24 are formed a plurality of (e.g., three) annular protruding portions 24b having a semi-circular cross-section in a widthwise direction.

In addition, the member 24 is in close contact with the inner cylinder 21 and the case portion 22 by a radial thickness thereof, and has a shape forming a predetermined fixed gap between them.

Then, in the gap between the inner cylinder 21 and the case portion 22, a closed end-side region of the case portion 22 in sections partitioned by the member 24 is provided between the inflow portion 4 and the processing flow path 21d to form the first chamber 26 serving as an inflow-side flow straightening chamber, which communicates with the opening of the inner cylinder 21 on the step portion 21c side. Additionally, an open end-side region of the case portion 22 in the sections partitioned by the member 24 is provided between the outflow portion 5 and the processing flow path 21d to form the second chamber 27 serving as an outflow-side flow straightening chamber, which communicates with the processing flow path 21d via the communication port 21a.

In this case, an inner volume of the first chamber 26 is set to be equal to or more than ⅔ of the cube of the processing flow path equivalent inner diameter of the processing flow path 21d (about 67% or more) and equal to or less than 3 times of processing flow path inner volume of the processing flow path 21d. By setting the inner volume of the first chamber 26 to within such a range, a further flow straightening effect can be obtained as compared with when not providing the first and second chambers 26 and 27. Note that the inner volume of the first chamber 26 is more preferably equal to or more than 75% of the cube of the processing flow path equivalent inner diameter and equal to or less than 2 times of the processing flow path inner volume, and still more preferably equal to or more than 85% of the cube of the processing flow path equivalent inner diameter and equal to or less than the processing flow path inner volume. When the inner volume of the first chamber 26 exceeds 3 times of the processing flow path inner volume, the entire size of the fluid sterilization module 1 becomes too large relative to processing flow rate, so that the inner volume of the first chamber 26 is preferably equal to or less than 3 times of the processing flow path inner volume.

Additionally, a cross-sectional area A26 of the first chamber 26 illustrated in FIG. 2B is set to be preferably 1/10 to 1 of a cross-sectional area A21 of the processing flow path 21d, and more preferably from 1/10 to ½ thereof. When the cross-sectional area A26 of the first chamber 26 is smaller than 1/10 of the cross-sectional area A21 of the processing flow path 21d, it is difficult to function as the fluid sterilization module 1. Setting the cross-sectional area A26 to be larger than the cross-sectional area A21 makes it difficult to sufficiently suppress biofilm formation.

Specifically, assume that when the fluid sterilization module 1 performs sterilization processing at a processing flow rate of 2 L/min, a cross-sectional area necessary for sterilization, i.e., the cross-sectional area A21 of the processing flow path 21d is $A21 > 3.14$ cm$^2$, and the cross-sectional area A26 of the first chamber 26 necessary for prevention of biofilm formation is $A26 < 1.53$ cm$^2$. The relative values are considered to be proportional to the flow rate. Thus, when the processing flow rate is X L/min, the cross-sectional area A21 of the processing flow path 21d necessary for sterilization can be represented as $A21 > 1.57 \times X$ cm$^2$, and the cross-sectional area A26 of the first chamber 26 necessary for prevention of biofilm formation can be represented as $A26 < 0.76 \times X$ cm$^2$. Accordingly, "the cross-sectional area A21 necessary for sterilization the cross-sectional area A26 necessary for prevention of biofilm formation" is preferably larger than 2.06 (($A21/A26) > 2.06$). Note that the length of the processing flow path 21d is determined depending on the transmittance of the object, and not depending on intended processing flow rate.

Figure 5:
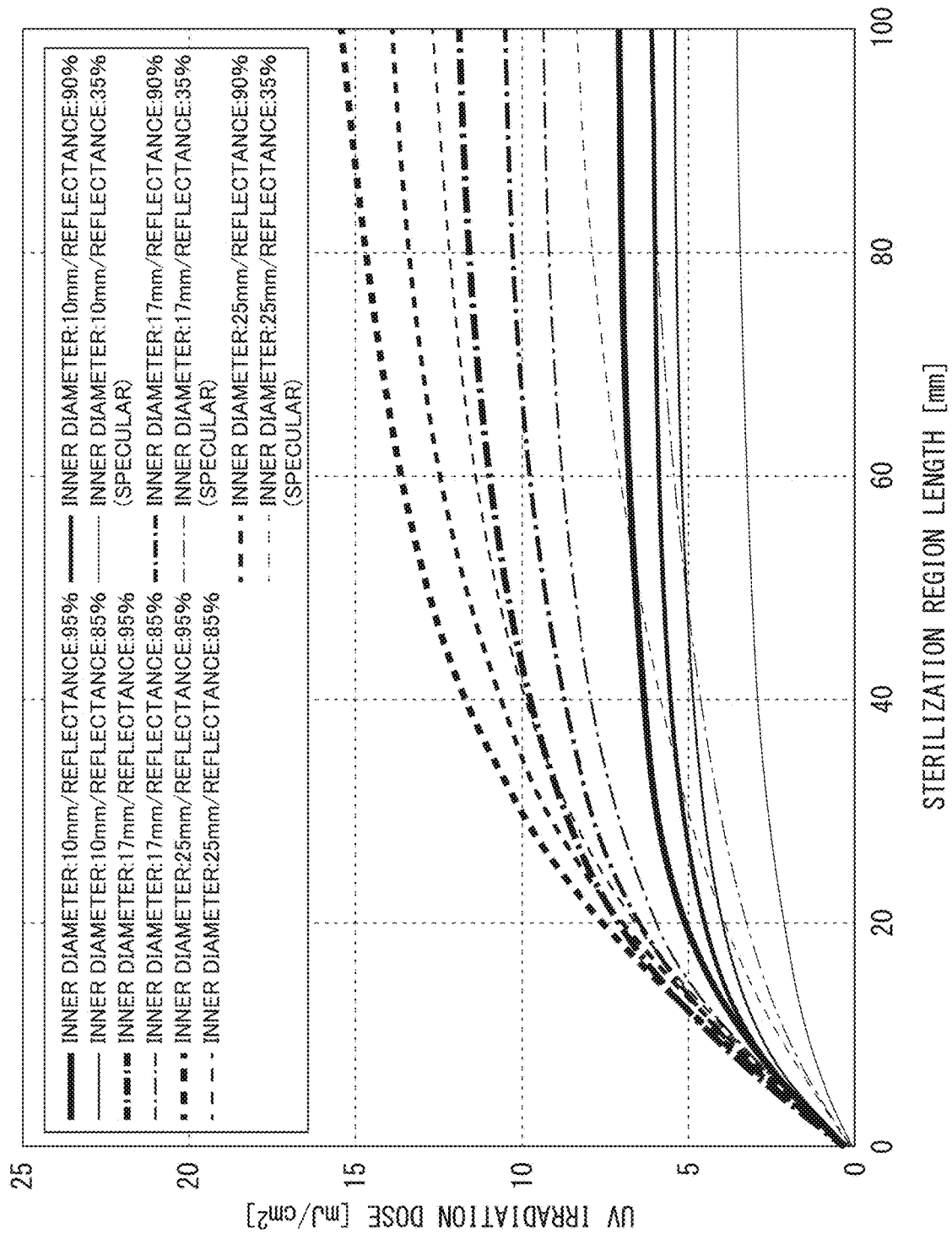
FIG. 5 illustrates one example of a characteristic diagram illustrating a relationship between sterilization region length and ultraviolet light irradiation dose necessary for sterilization.

FIG. 5 is a characteristic diagram illustrating a relationship between the length of a sterilization region, i.e., the length of the processing flow path 21d and the dose (cumulative irradiation dose) of ultraviolet light absorbed by a fluid and used for sterilization. In FIG. 5, the horizontal axis represents sterilization region length [mm], and the vertical axis represents ultraviolet light irradiation dose (cumulative irradiation dose) [mJ/cm$^2$]. In each characteristic line, the inner diameter of the processing flow path 21d and the transmittance of the processing flow path 21d are different. By determining the inner diameter of the processing flow path 21d and the transmittance of the processing flow path 21d, the length of the processing flow path 21d and the ultraviolet light irradiation dose (the cumulative irradiation dose) can be determined from FIG. 5. In other words, by making balance between the flow velocity for preventing biofilm formation and the irradiation dose for ensuring a certain sterilization capability, there can be provided a sterilization capability stable for a long time.

Note that the material of the member 24 is not limited to fluorine rubber, and can be any material that can partition such that the object does not move back and forth between the closed end side and the open end side of the case portion 22 in the gap between the inner cylinder 21 and the case portion 22 and that has durability.

In addition, the number of the protruding portions 24b provided on the member 24 is not limited to three as long as it is more than one. Providing the plurality of the protruding portions 24b enables the inner cylinder 21 and the case portion 22 to be stably fixed together. It is sufficient that the protruding portions 24b are arranged in a widthwise direction, for example, at an equal interval. In short, it is sufficient to arrange the protruding portions 24b at an equal interval such that the gap between the inner cylinder 21 and the case portion 22 does not become uniform due to a cause such as deviation of the arrangement positions of the protruding portions 24b.

Note that the equivalent inner diameter or the equivalent diameter as used herein refers to "(four times the flow path cross-sectional area)/(flow path cross-sectional peripheral length)".

In addition, the equivalent radius refers to "twice the flow path cross-sectional area/flow path cross-sectional peripheral length".

Furthermore, the flow straightening chamber refers to a space which is arranged between the processing flow path and an external device, which includes an inflow port and an outflow port for transferring an object between the fluid sterilization module 1 and the external device, and which has an equivalent inner diameter of 1.1 times or more, and preferably 1.5 times or more, with respect to the processing flow path equivalent inner diameter.

Returning to FIG. 2A, the light emitting unit 3 includes a window portion 31 (a component for covering the entire opening) and an element portion 32.

The window portion 31 is formed using, for example, stainless steel or the like, and formed into an annular shape having the same outer diameter as that of the flange portion 22a of the case portion 22. On an inner peripheral surface of the window portion 31 are formed a first step portion 31a and a second step portion 31b larger in diameter than the first step portion 31a. A disc-shaped window 33 formed using an ultraviolet light transmitting material such as, for example, quartz glass, is fitted into the second step portion 31b in such a manner as to be flush with a surface of the window portion 31 on the element portion 32 side.

The element portion 32 is formed using, for example, stainless steel or the like, and formed into an annular shape having the same outer diameter as that of the window portion 31. On a surface of the element portion 32 facing the window portion 31 is formed a recessed portion 32a having a circular shape in plan view. A light source 34 includes a light emitting element 34a such as a UVC-LED (deep ultraviolet LED) and a substrate 34b mounted with the light emitting element 34a thereon, and is fixed to the recessed portion 32a such that a light emitting surface thereof faces the window portion 33. The light source 34 is arranged such that an optical axis of irradiation light from the light source 34 is coincident with a longitudinal center axis of the processing flow path 21d.

On a surface of the element portion 32 on a side opposite to the window portion 31 is formed a recessed portion 32b for fixing a control substrate mounted with an unillustrated control device and the like thereon.

The sterilization processing unit 2 and the light emitting unit 3 are integrally fixed by a through bolt 25 at the flange portion 22a of the case portion 22.

In this case, the step portion 22b is provided with an O ring 22c formed by an elastic member such as rubber, and also provided with an annular elastic sheet 22d formed by an elastic member between the end of the inner cylinder 21 on the communication port 21a side and the window portion 31 to prevent the object from leaking outside from a contact part between the window portion 31 and the case portion 22. As the elastic member forming the elastic sheet 22d, an elastomer such as a silicon resin elastomer or a fluororesin elastomer is preferably applied.

In addition, the elastic sheet 22d is fixed by the through bolt 25 while being interposed between the end of the inner cylinder 21 on the communication port 21a side and the window portion 31, whereby the plate 23 provided on the step portion 21c of the inner cylinder 21 is pushed and pressed by the protruding portion 22α and sandwiched by the protruding portion 22α and the step portion 21c so that the plate 23 is fixed to the step portion 21c.

Additionally, an O ring 31c formed by an elastic member such as rubber is provided between the first step portion 31a of the window portion 31 and the window 33 to prevent the object from leaking outside from the contact part between the window portion 31 and the window 33.

A gap between the end of the inner cylinder 21 and a region of the window portion 31 facing the end of the inner cylinder 21 via the elastic sheet 22d can be set to 25 μm or less from the viewpoint of mechanical processing accuracy and the like. Furthermore, when the gap is 10 μm or less, no leakage substantially occurs due to surface tension of water or the like as the object.

Advantageous Effects (1) The fluid sterilization module 1 according to the first embodiment of the present invention includes the first chamber 26 having a predetermined volume or more at the upstream of the processing flow path 21d. Thus, for example, even when assembly accuracy varies, influence of the varied assembly accuracy can be mitigated by allowing an object to flow into the processing flow path 21d via the first chamber 26, as a result of which variation in the flow velocity of the object in the processing flow path 21d can be suppressed. Thus, there can be obtained the flow sterilization module 1 in which variation between individual products in terms of assembly accuracy is suppressed.

(2) The fluid sterilization module 1 according to the first embodiment of the present invention is configured to allow the object having passed through the processing flow path 21d to flow into the second chamber 27 only via the communication port 21a provided close to the end of the inner cylinder 21 on the light emitting unit 3 side and then flow out from the outflow portion 5. The object having passed through the processing flow path 21d will be all flown out only via the communication port 21a. Thus, even when the flow rate fluctuates, fluctuation of the flow velocity distribution in the processing flow path 21d due to the fluctuated flow rate can be suppressed. This can prevent sterilization failure from occurring due to the fluctuation of the flow velocity distribution.

(3) The fluid sterilization module 1 according to the first embodiment of the present invention is configured so that the cross-sectional area A26 of the first chamber 26 is from 1/10 to 1 of the cross-sectional area A21 of the processing flow path 21d, and more preferably from 1/10 to 1/2 thereof.

Thus, sterilization effect in the processing flow path 21d can be obtained, and also biofilm formation in the first chamber 26 can be prevented.

In addition, the inner cylinder 21 is formed using a material such that the static friction coefficient on the outer peripheral surface thereof is smaller than that of the inner peripheral surface of the case portion 22. This can facilitate detection of biofilm formation, and enables biofilm formation to be detected when biofilm is formed on the inner peripheral surface side of the case portion 22 prior to biofilm formation in the entire first chamber 26. This can be a contribution to reduction of risks due to biofilm.

Herein, the state of formation of biofilm adherent on the case portion 22 side can be checked by closely bringing a light source such as a flashlight to the outer peripheral surface of the case portion 22 and visually recognizing a contamination state from internal reflection of the case portion 22 at a time of regular maintenance on the fluid sterilization module 1.

By contrast, on the inner cylinder 21 side are provided the first chamber 26 serving as the inflow-side flow straightening chamber and the second chamber 27 serving as the outflow-side flow straightening chamber between the inner cylinder 21 and the case portion 22, and, in other words, there exist fluid layers different in refractive index. Due to this, biofilm adherent to the inner cylinder 21 side cannot be visually recognized from outside the case portion 22. In short, it is difficult to visually recognize biofilm adherent to the inner cylinder 21 side. Thus, it is practically very important to devise such that biofilm formation on the inner cylinder 21 side occurs later than on the case portion 22 side. Specifically, since it is expected that no biofilm is formed on the inner cylinder 21 side at the time of detection of adhesion of biofilm on the case portion 22 side, it is sufficient to take measures against biofilm on the inner cylinder 21 at the time of detection of biofilm adherent on the case portion 22 side.

In this manner, the fluid sterilization module 1 according to the first embodiment of the present invention can suppress biofilm formation in the first chamber 26. Thus, reduction in the sterilization effect by provision of the first chamber 26 can be further suppressed.

(4) In the fluid sterilization module 1 according to the first embodiment of the present invention, the thickness of the inner cylinder 21 is from 1 mm to 20 mm, and the inner cylinder 21 is formed using an ultraviolet light reflecting material having a diffuse transmittance of from 1%/mm to 20%/mm and a total reflectance of from 80%/mm to 99%/mm in the ultraviolet light region.

Figure 6:
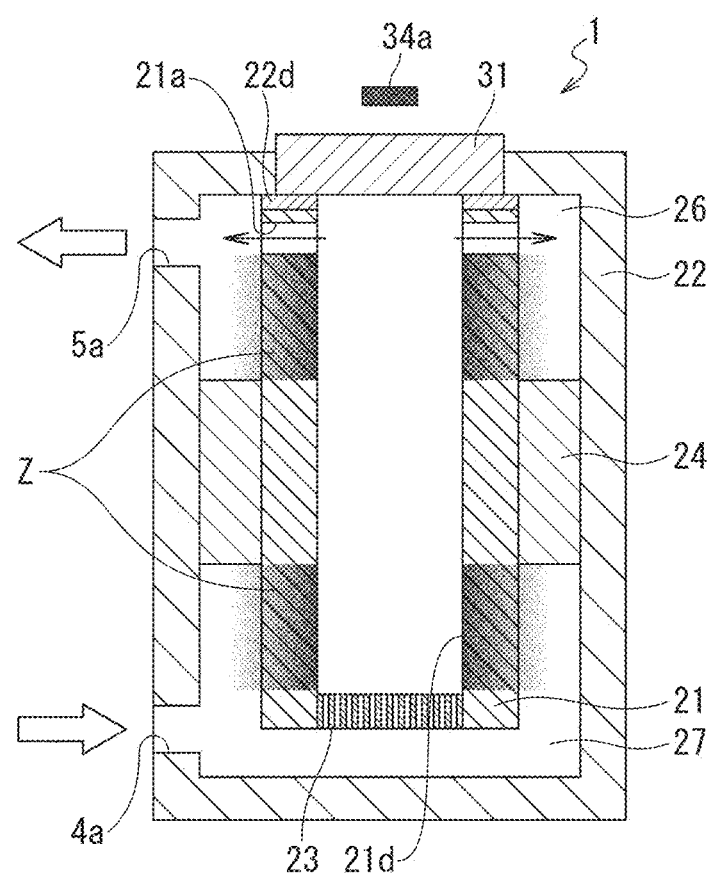
FIG. 6 is an illustrative diagram for illustrating a state of transmission of ultraviolet light.

Thus, ultraviolet light applied to the processing flow path 21d from the light emitting unit 3 can be confined with high density in the processing flow path 21d, whereby strong sterilization capability can be exerted. Additionally, since the inner cylinder 21 transmits a part of ultraviolet light therethrough, ultraviolet light applied in the processing flow path 21d is transmitted through the inner cylinder 21 and applied to insides of the first chamber 26 and the second chamber 27, as indicated by sign Z in FIG. 6. In other words, the ultraviolet light is applied also to the fluid in the first chamber 26 and the second chamber 27, which thus can prevent bacteria from growing in the object contained in the first chamber 26 and the second chamber 27. As a result, even when the object is contained in the first chamber 26 and the second chamber 27, bacterial generation can be suppressed, which can suppress outflow of the object containing grown bacteria upon start of flow of the object, so that reliability on the fluid sterilization module 1 can be further improved. Note that FIG. 6 simply illustrates the fluid sterilization module 1 illustrated in FIG. 2A.

(5) In the fluid sterilization module 1 according to the first embodiment of the present invention, the gap between the inner cylinder 21 and the case portion 22 is divided into the inflow portion 4 side and the outflow portion 5 side by the member 24. Thus, even when assembly accuracy is low, leakage of the object from the flow path including the first chamber 26 and the second chamber 27 can be reduced. In addition, the leakage reduction can be achieved by interposing the member 24 between the inner cylinder 21 and the case portion 22, and therefore can be achieved without significantly increasing manufacturing steps. Additionally, since the member 24 is formed by an elastic member, there can be obtained the fluid sterilization module also excellent in robustness, for example, in operation.

Modifications

While the above embodiment has been described the case where the invention is applied to the fluid sterilization module for sterilizing a fluid, the object to be sterilized may be a fluid such as water, an aqueous solution, or a colloidal dispersion solution, a gas such as air, a fine powder of ice or solid, or the like.

In addition, while the above embodiment has been described the case where the protruding portion 24a is provided on the inner peripheral surface side of the member 24, and the plurality of protruding portions 24b are provided on the outer peripheral surface side thereof, the invention is not limited thereto. In short, the member 24 can be of any shape as long as movement of the member 24 in the extending direction of the inner cylinder 21 can be restricted by fitting the member 24 with the groove 21b provided on the outer peripheral surface of the inner cylinder 21, it is possible to prevent the object from moving from one side partitioned by the member 24 to the other side through the contact surface between the member 24 and the inner cylinder 21 and the contact surface between the member 24 and the case portion 22, and the member 24 has sufficient durability.

Figure 7:
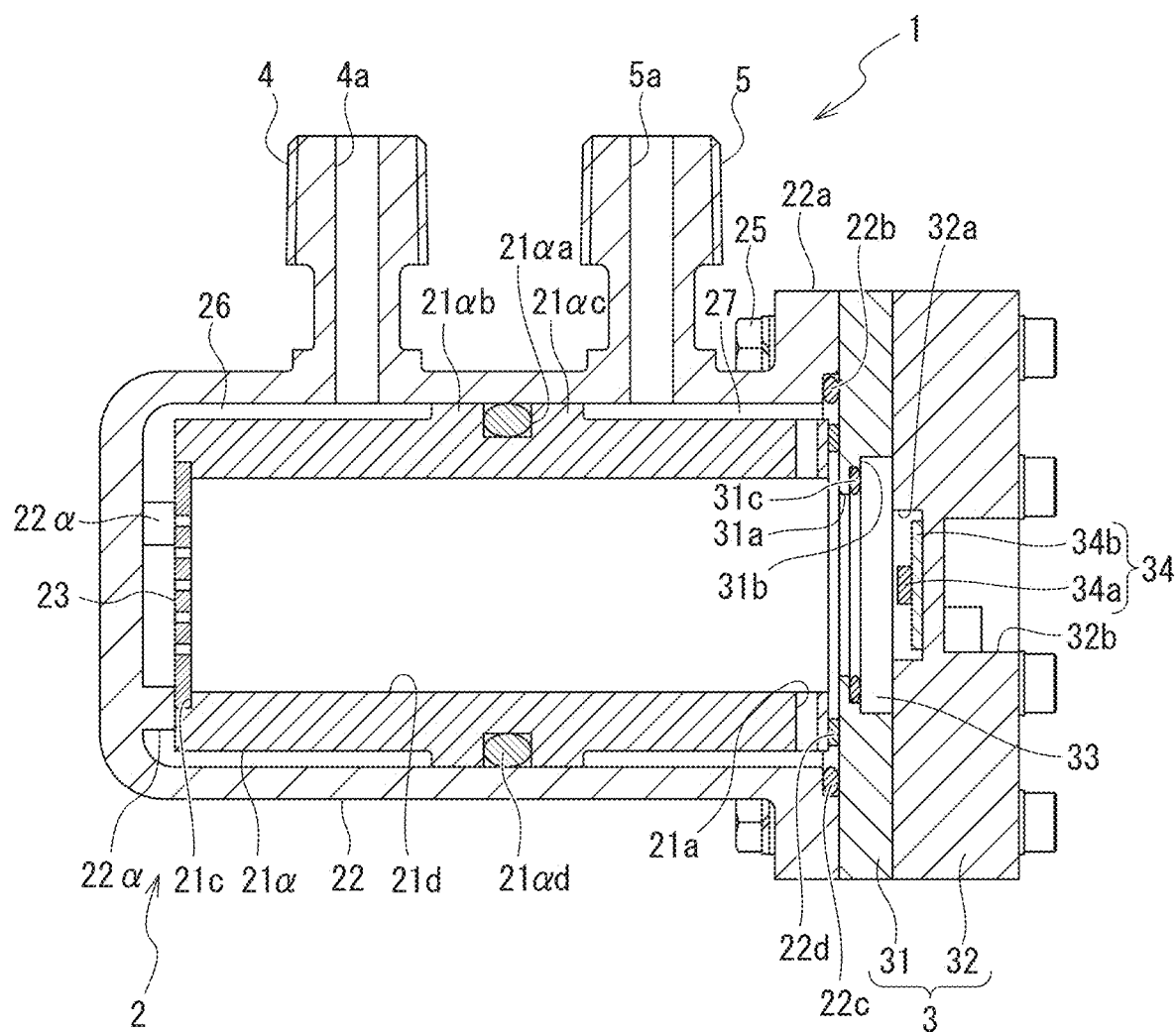
FIG. 7 illustrates a modification of the fluid sterilization module according to the first embodiment.

For example, instead of the inner cylinder 21 illustrated in FIG. 2A, an inner cylinder 21α illustrated in FIG. 7 may be used. As illustrated in FIG. 7, the inner cylinder 21α includes an annular groove 21αa formed on an outer peripheral surface of a center part in a direction in which the inner cylinder 21α extends and annular protruding portions 21αb and 21αc formed on both sides of the groove 21αa. The protruding portions 21αb and 21αc are formed in such a height that allows outer peripheral surfaces of the protruding portions 21αb and 21αc to contact with an inner peripheral surface of the case portion 22. Additionally, an O ring 21αd formed by an elastic member such as rubber is fitted in the groove 21αa. The inner cylinder 21α thus formed is housed in the case portion 22, whereby the outer peripheral surfaces of the protruding portions 21αb and 21αc and the O ring 21αd contact with the inner peripheral surface of the case portion 22 to form a gap between the case portion 22 and the inner cylinder 21α on the inflow portion 4 side of the protruding portion 21αb and on the outflow portion 5 side of the protruding portion 21αc. The gap on the inflow portion 4 side of the protruding portion 21αb forms the first chamber 26, and the gap on the outflow portion 5 side of the protruding portion 21αc forms the second chamber 27.

Using the inner cylinder 21α having such a structure can also provide functional advantageous effects equivalent to those described above.

Furthermore, in the above embodiment, as illustrated in FIG. 2A, the gap between the inner cylinder 21 and the case portion 22 is divided into two sections by the member 24, and one of the divided two sections is used as the first chamber 26, and the other one thereof is used as the second chamber 27. However, the invention is not limited thereto. For example, the first chamber 26 and the second chamber 27 may be individually formed as separate ones. Additionally, although the above embodiment includes the first chamber 26 and the second chamber 27, an embodiment including at least the first chamber 26 only is also applicable.

Still furthermore, while the above embodiment has been described the case where the light emitting element 34a is provided at the end of the processing flow path 21d on the side opposite to the plate 23, the light emitting element 34a can be provided at the end thereof on the plate 23 side, further, can be provided both on the plate 23 side and the side opposite thereto.

Second Embodiment

Next, a second embodiment will be described.

Figure 8:
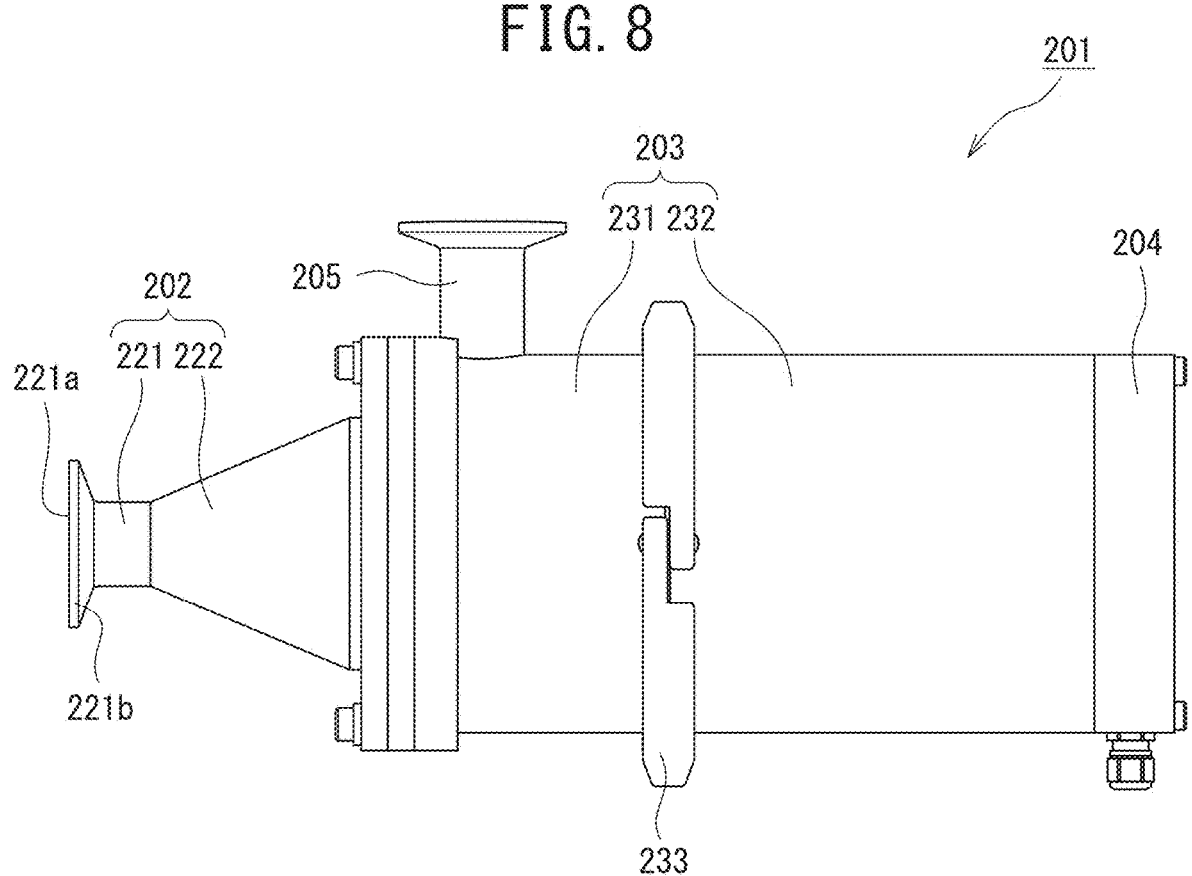
FIG. 8 is an external appearance diagram illustrating one example of a fluid sterilization module according to a second embodiment.
Figure 9:
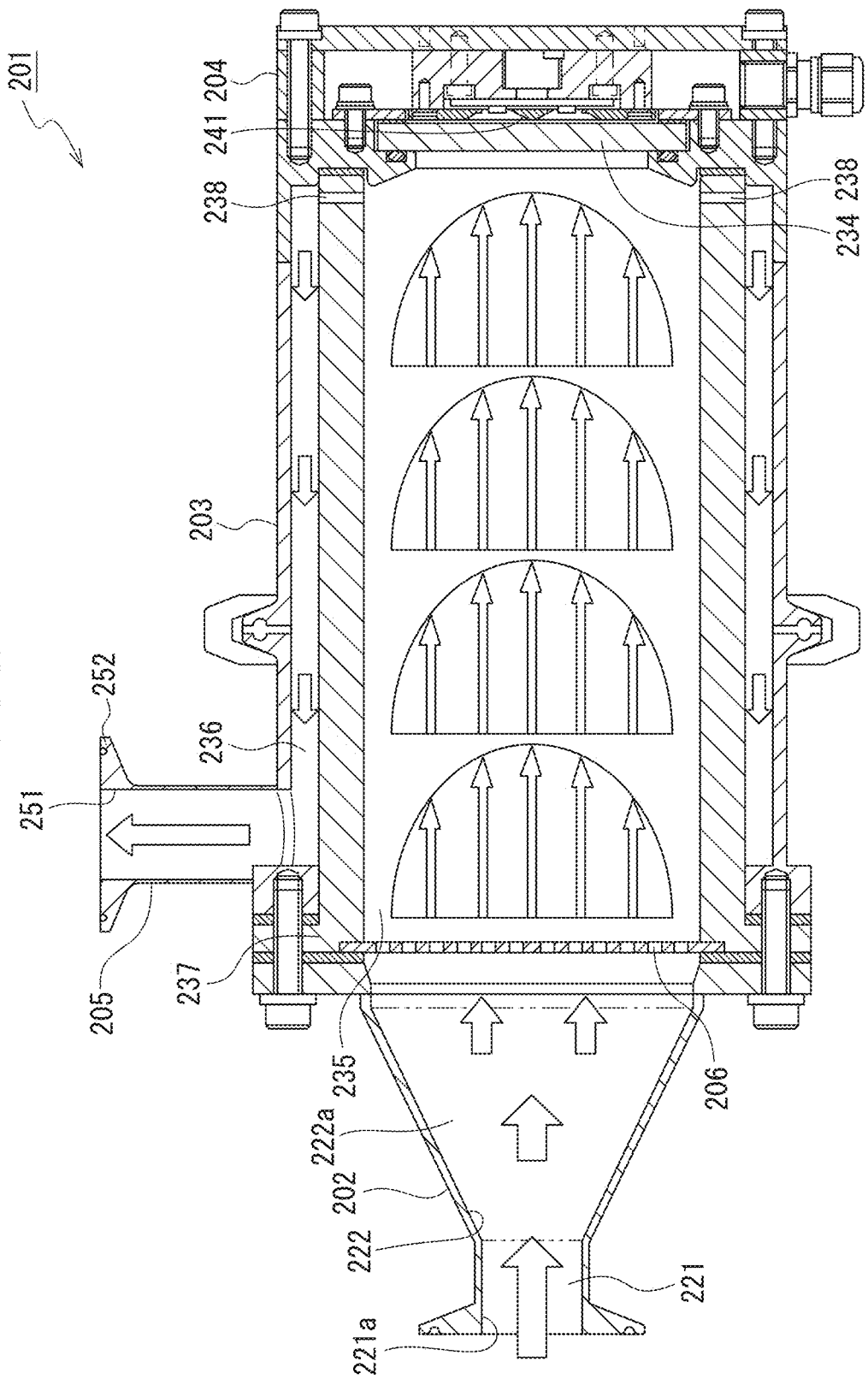
FIG. 9 is a longitudinal cross-sectional diagram of FIG. 8.

FIG. 8 depicts a fluid sterilization module to which the ultraviolet light irradiation device according to the present invention is applied, and illustrates a front view of one example of a fluid sterilization module 201. Additionally, FIG. 9 is a longitudinal cross-sectional diagram of FIG. 8.

The fluid sterilization module 201 includes an inflow portion 202, a cylindrical portion (a cylindrical portion) 203, a light emitting unit 204, and an outflow portion 205, as illustrated in FIG. 8. The inflow portion 202 is attached to one end of the cylindrical portion 203, and the light emitting unit 204 is attached to the other end of the cylindrical portion 203.

The inflow portion 202 includes an end portion 221 and a tapered portion 222, and at one end of the end portion 221 are formed an inflow port 221a configured to allow a fluid to flow in along a longitudinal direction of the cylindrical portion 203 and a flange 221b configured to connect the inflow port 221a to another tube or the like. Note that a space 222a in the tapered portion 222 corresponds to a first chamber described in the claims.

The tapered portion 222 is formed into a tapered shape whose diameter becomes wider in a flowing direction of the fluid introduced. A smaller diameter side of the tapered portion 222 is connected to the other end of the end portion 221, and a larger diameter side of the tapered portion 222 is attached to one end of the cylindrical portion 203 via a plate (a plate covering an opening of the cylindrical portion) 206, as illustrated in FIG. 9.

The tapered portion 222 is provided to form the flow of an introduced fluid into a flow with Poiseuille distribution. The flow with Poiseuille distribution can be formed by forming a tapered shape such that the inflow port for the fluid is narrowed and then becomes wider. The tapered shape has a taper ratio of preferably from 0.2 to 0.68. By setting the taper ratio in the range, a flow with Poiseuille distribution can be achieved in a longer distance.

Figure 10:
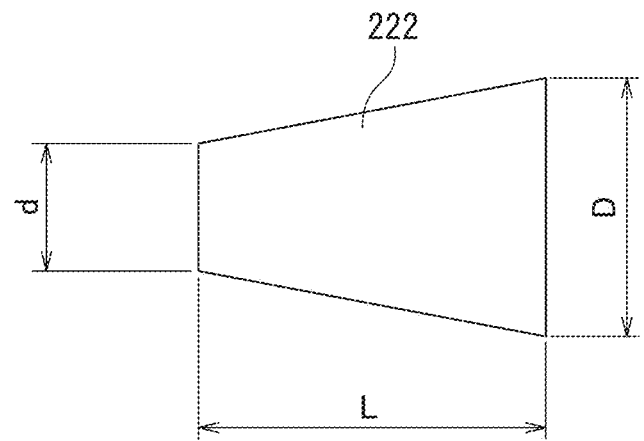
FIG. 10 is an illustrative diagram for illustrating a taper ratio.

Note that the taper ratio is represented by the following formula (1), where "d" represents a small diameter side diameter of an inside of the tapered portion 222, "D" represents a large diameter side diameter thereof, and "L" represents a length of the tapered portion 222, i.e., a distance from an end thereof on the small diameter side to an end thereof on the larger diameter side, as illustrated in FIG. 10.

$$\text{Taper ratio} = (D-d)/L \ldots \quad (1)$$

The cylindrical portion 203 includes a first member 231 on the inflow portion 202 side and a second member 232 on the light emitting unit 204 side, in which the first member 231 and the second member 232 are integrally bonded by a bonding member 233, as illustrated in FIG. 8. Additionally, on an end face of the cylindrical portion 203 on the light emitting unit 204 side is provided a window portion 234 configured to allow ultraviolet light from a light source 241 housed in the light emitting unit 204 to pass therethrough, as illustrated in FIG. 9. The window portion 234 is formed using a material having high ultraviolet light transmittance, such as quartz ($SiO_2$), sapphire ($Al_2O_3$), or amorphous fluorine-based resin.

As illustrated in FIG. 9, in the cylindrical portion 203, there is provided a separation wall 237 configured to separate the inside of the cylindrical portion 203 into an inner flow path (processing flow path) 235 having an inner diameter substantially equivalent to the large diameter side of the tapered portion 222 and an outer flow path 236 formed outside the inner flow path 235. A plurality of communication holes (communication ports) 238 allowing for communication between the inner flow path 235 and the outer flow path 236 are formed close to an end of the separation wall 237 on the light emitting unit 204 side. Note that the outer flow path 236 corresponds to a second chamber described in the claims.

In addition, on an outer periphery of the cylindrical portion 203 close to an end on the inflow portion 202 side is provided an outflow portion 205 configured to allow the fluid in the fluid sterilization module 201 to flow out. One end of the outflow portion 205 communicates with the outer flow path 236, and at the other end thereof are formed an outflow port 251 from which the fluid flows out and a flange 252 configured to connect the outflow port 251 to another tube or the like.

With this structure, the fluid introduced from the inflow port 221a passes through the tapered portion 222, the inner flow path 235, the communication holes 238, and the outer flow path 236, and flows out from the outflow port 251.

The light emitting unit 204 includes the light source 241 that is arranged such that an irradiation surface thereof faces the window portion 234, and the center of the irradiation surface faces the center of the inner flow path 235 when seen from a direction in which the fluid flows. The light source 241 emits ultraviolet light having a wavelength with high sterilization efficiency of around from 260 nm to 270 nm, and is formed by, for example, a light emitting element such as an ultraviolet light emitting diode having a center wavelength of from 230 nm to 300 nm.

Figure 11:
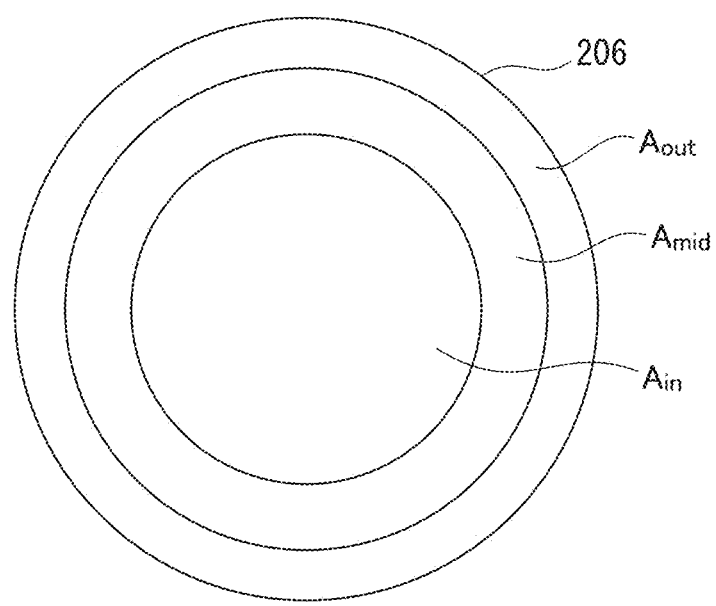
FIG. 11 is an illustrative diagram for illustrating an aperture ratio of a flow straightening plate.

The plate 206 is provided to form the flow of an introduced fluid into a flow with Poiseuille distribution. The flow with Poiseuille distribution can be formed into a shape closer to an ideal shape by providing the plate 206. The plate 206 includes a plurality of opening holes 206a penetrating between front and back surfaces, and the opening holes 206a are arranged such that the plate 206 has a large aperture ratio at a center part thereof, and has a small aperture ratio at a peripheral part thereof. In the plate 206, for example, as illustrated in FIG. 11, when divided into three regions being concentric circles and having an equal area, the aperture ratio of an innermost region (hereinafter referred to as "inner region") Ain is preferably from 6 times to 10 times with respect to the aperture ratio of an outermost region (hereinafter referred to as "outer region") Aout. The aperture ratio of a middle region Amid located between the inner region Ain and the outer region Aout is the same as either the aperture ratio of the outer region Aout or the aperture ratio of the inner region Ain or an aperture ratio between the aperture ratios of both thereof. When the aperture ratio of the inner region Ain is from 6 times to 10 times with respect to the aperture ratio of the outer region Aout, a flow with Poiseuille distribution can be maintained in a longer distance.

Note that the aperture ratio of the entire plate 206 is preferably 10% or more from the viewpoint of suppressing module pressure loss, and, from the viewpoint of flow straightening capability of the plate 206 and strength thereof, preferably 50% or less, more preferably 30% or less, and still more preferably 20% or less.

In addition, division of the aperture ratio of the plate 206 is not limited to three stages, and the aperture ratio thereof can be divided into any number of stages. In short, it is sufficient that a flow with Poiseuille distribution can be formed by allowing a fluid introduced at a Reynolds number of 3000 or more to pass through the plate 206, and similarly, the size and arrangement position of the opening holes 206a can also be optionally set.

Figure 12:
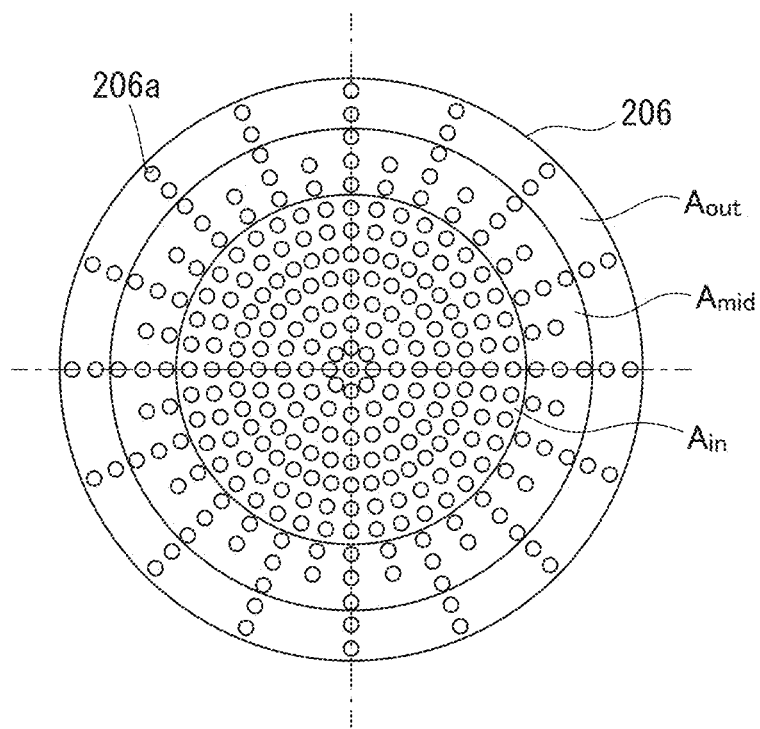
FIG. 12 is a plan view illustrating one example of the flow straightening plate.
Figure 13:
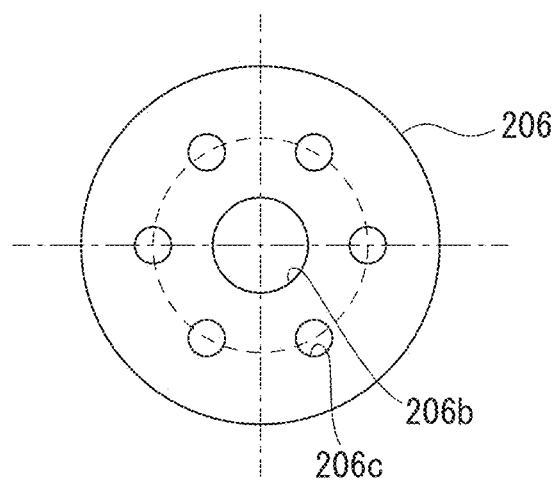
FIG. 13 is a plan view illustrating one example of the flow straightening plate.

FIGS. 12 to 14 illustrate arrangement examples of the opening holes 206a of the plate 206.

FIG. 12 illustrates an example of the aperture ratio divided into three stages in which the number of the opening holes 206a arranged is made different between the inner region Ain, the middle region Amid, and the outer region Aout to make the aperture ratios different. In other words, the sizes of the opening holes 206a are the same, and the opening holes 206a may be arranged such that the inner region Ain has a largest number of the opening holes 206a arranged, the middle region Amid has a secondly largest number of the opening holes 206a arranged, and the outer region Aout has a smallest number of the opening holes 206a arranged.

FIG. 13 illustrates an example of the aperture ratio divided into two stages, in which the sizes of opening holes are made different to make the aperture ratios different. Specifically, in the plate 206 having a circular shape in plan view, an opening hole 206b having a relatively large hole diameter is provided at the center part, and a plurality of opening holes 206c having a smaller hole diameter than that of the opening hole 206b are arranged at positions on a concentric circle of the plate 206 in such a manner as to surround the opening hole 206b. In this manner, the aperture ratio can be divided into two stages. Note that the aperture ratio may be adjusted by adjusting both the size of the opening hole 206b and the number of the opening holes 206c arranged.

Figure 14A:
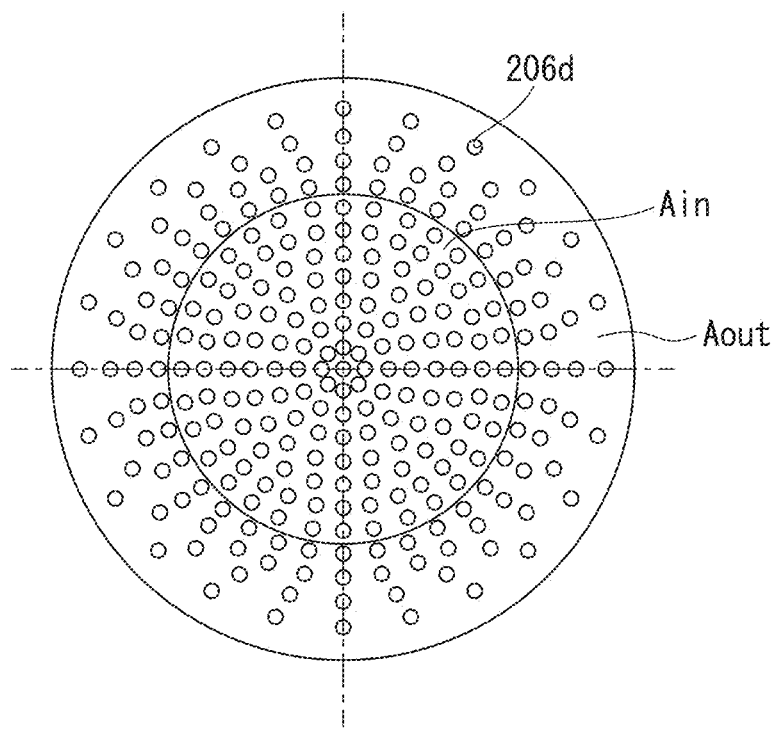
FIGS. 14A and 14B are plan views illustrating one example of the flow straightening plate.
Figure 14B:
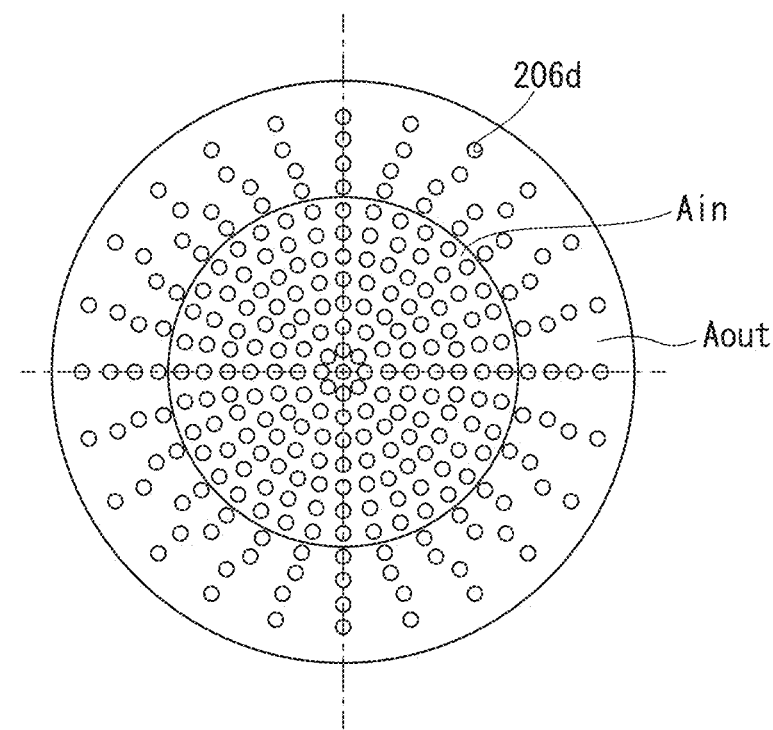

In FIGS. 14A and 14B, the aperture ratio is divided into two stages by differing the number of opening holes. Opening holes 206d have the same hole diameter. In FIG. 14A, 145 opening holes 206d are arranged in the inner region Ain, and 124 opening holes 206d are arranged in the outer region Aout so that the aperture ratio has a ratio of 2:1. In FIG. 14B, 165 opening holes 206d are arranged in the inner region Ain, and 104 opening holes 206d are arranged in the outer region Aout so that the aperture ratio has a ratio of 3:1.

In the fluid sterilization module 201 having such a structure, a Reynolds number Re of a fluid to be introduced into the inflow port 221a is set to 3000 or more.

Herein, to form the fluid flowing through the flow path into a flow with Poiseuille distribution, it is necessary that the Reynolds number of the fluid flowing through the flow path needs to be equal to or less than a critical Reynolds number in a laminar flow state, and for example, it is known that the critical Reynolds number of a flow in a circular tube is about 2300. Thus, even when a fluid having a Reynolds number of 3000 or more is introduced into a circular tube, it is difficult in this state to form the flow into a flow with Poiseuille distribution.

On the other hand, in the fluid sterilization module 201 illustrated in FIG. 9, the fluid introduced into the inflow port 221a passes through the tapered portion 222, additionally passes through the plate 206, and then flows into the inner flow path 235.

Herein, the tapered portion 222 has a smaller tube diameter on the inlet side thereof, and then the diameter becomes wider. Thus, in the tapered portion 222, the flow of the fluid becomes wider in a sidewall direction of the tapered portion 222. In other words, as indicated by arrows in FIG. 9, the flow concentrates to the center part of the tapered portion 222 when seen from a direction in which the fluid flows, and, in other words, a flow with Poiseuille distribution is formed. Then, since the taper ratio of the tapered portion 222 is set to be from 0.2 to 0.68, the flow with Poiseuille distribution can be maintained in a long distance of the inner flow path 235.

Furthermore, the plate 206 is provided between the tapered portion 222 and the inner flow path 235. The plate 206, when divided into three regions being concentric circles and having an equal area, is formed such that the aperture ratio of the inner region is larger than the aperture ratio of the outer region. Arranging the plate 206 widens the flow of the fluid in the sidewall direction of the inner flow path 235. However, since the aperture ratio of the inner region is larger, the flow rate of the fluid flowing in the inner region becomes larger than in the outer region. Due to this, as indicated by arrows in FIG. 9, when seen from the direction in which the fluid flows, the flow velocity of the fluid flowing in the center part of the inner flow path 235 becomes higher, whereas the velocity of the fluid flowing closer to the sidewall of the inner flow path 235 becomes lower than the fluid flowing in the center part. In other words, a flow with Poiseuille distribution is formed. In addition, the aperture ratio of the inner region is from 6 times to 10 times with respect to the aperture ratio of the outer region. Thus, providing the plate 206 also enables the flow with Poiseuille distribution to be maintained in the long distance of the inner flow path 235.

Then, as illustrated in FIG. 15, the light source 241 has intensity distribution characteristics in which the closer to the center of the irradiation surface, the higher the light emission intensity, and the closer to the edge of the irradiation surface, the lower the light emission intensity. Additionally, the light source 241 is arranged such that the center of the irradiation surface faces the center of the inner flow path 235 when seen from the direction of flow of the fluid. Thus, the light source 241 irradiates the center part having the higher flow velocity with the part having the highest light emission intensity. As a result, the amount of energy of ultraviolet light that acts on the fluid having a flow velocity distribution like Poiseuille distribution and passing through the inner flow path 235 can be equalized regardless of the position of a radial direction through which the fluid passes. By doing this, ultraviolet light with a predetermined amount or more of energy can be applied to the entire part of the fluid flowing through the inner flow path 235, thereby enabling improvement in the sterilization effect on the entire fluid.

FIG. 16 illustrates one example of a flow velocity distribution when a fluid is introduced into the fluid sterilization module 201 illustrated in FIG. 8. As illustrated in FIG. 16, it can be seen that a region near the center part in the fluid sterilization module 201 when seen from the direction of flow of the fluid has a highest flow velocity. Note that FIG. 16 simply depicts the fluid sterilization module 201 illustrated in FIG. 9.

Note that while the second embodiment has been described the case where the flow with Poiseuille distribution is formed by the tapered portion 222 and the plate 206, as illustrated in FIG. 9, the invention is not limited thereto. As described above, a flow with Poiseuille distribution can be formed by providing at least one of the tapered portion 222 or the plate 206. Thus, even when either the tapered portion 222 or the plate 206 only is provided, a flow with Poiseuille distribution can be formed.

In addition, while the second embodiment has been described the case where the ultraviolet light irradiation device according to the present invention is applied to the fluid sterilization module having the double structure, as illustrated in FIG. 9, the invention is not limited thereto, and can be also applied to fluid sterilization modules configured to apply ultraviolet light to a fluid passing through the inside of a flow path. Additionally, the shape of the fluid sterilization module 201 is not limited to the double structure illustrated in FIG. 9, the ultraviolet light irradiation device of the invention can be applied to those configured to allow a fluid to pass through the inside of a circular tube or a cylindrical member, as a flow path.

In addition, while the second embodiment has been described the sterilization of a fluid, the object to be sterilized may be a fluid such as water, an aqueous solution, or a colloidal dispersion solution, a gas such as air, a fine powder of ice or a solid, or the like.

Additionally, while the second embodiment has been described the case where the light emitting unit 204 is provided at the end of the cylindrical portion 203 on the side opposite to the inflow portion 202, the light emitting unit 204 can be provided at the inflow portion 202 side, and alternatively, can be provided both on the inflow portion 202 side and the side opposite thereto.

While some exemplary embodiments of the present invention have been described hereinabove, the embodiments are those exemplifying devices and methods for embodying the technological idea of the present invention, and the technological idea of the invention should not be construed as specifying the materials, shapes, structures, arrangements, and the like of the constituent components. The technological idea of the present invention can be modified in various ways within the technological scope defined by the claims.

EXAMPLES

Hereinafter, a description will be given of Examples of fluid sterilization modules using the ultraviolet irradiation device according to the present invention.

Example A

The following illustrates a flow velocity distribution in the processing flow path 21d of the fluid sterilization module 1 according to the first embodiment.

Figure 17:
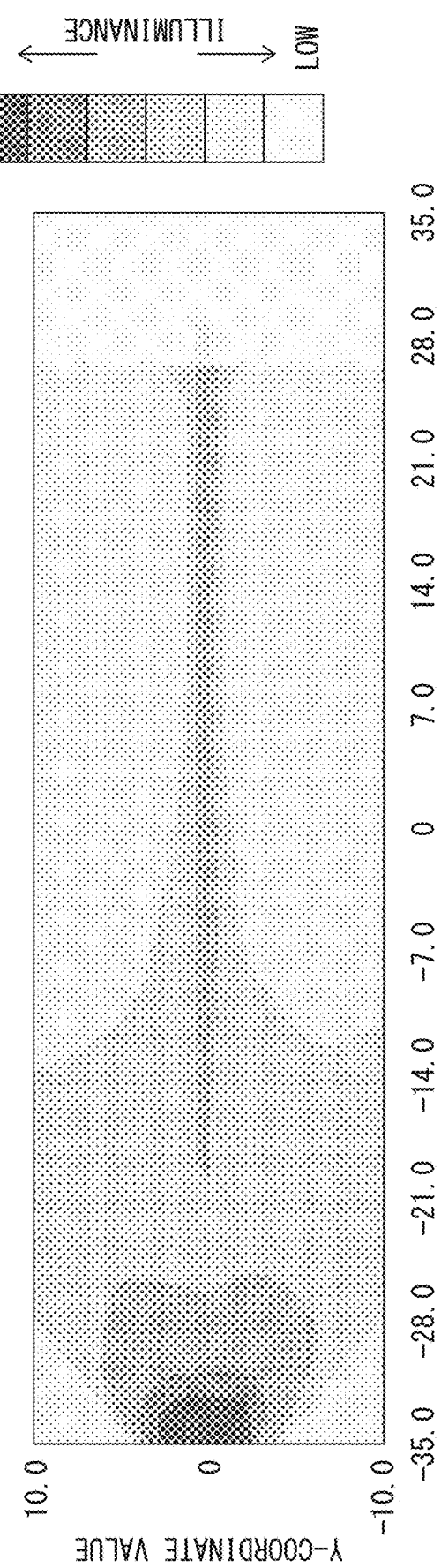
FIG. 17 is an illustrative diagram for illustrating ultraviolet light intensity of a light source according to the first embodiment.

Herein, it is preferable that the flow velocity distribution in the processing flow path 21d is uniform as much as possible. Specifically, for example, as illustrated in FIG. 17, in an illuminance distribution of the light emitting element such as a UVC-LED, illuminance in a center portion is higher by about 1.4 times than in a wall side region. Due to this, when the flow velocity in the processing flow path 21d does not match with the illuminance distribution, sufficient sterilization effect may be unobtainable at a portion where the flow velocity is high relative to the illuminance. Thus, the flow velocity distribution is preferably a distribution in which the flow velocity in the center portion is higher by about 1.4 times relative to that at a wall surface. However, since the wall surface flow velocity in the processing flow path is always 0, sterilization capability is expected to further improve as the flow velocity in the processing flow path is substantially more uniform.

Note that the following FIGS. 18 to 22 simply illustrate the fluid sterilization module 1. In addition, arrows in the drawings indicate flow directions.

Comparative Example A

Figure 18:
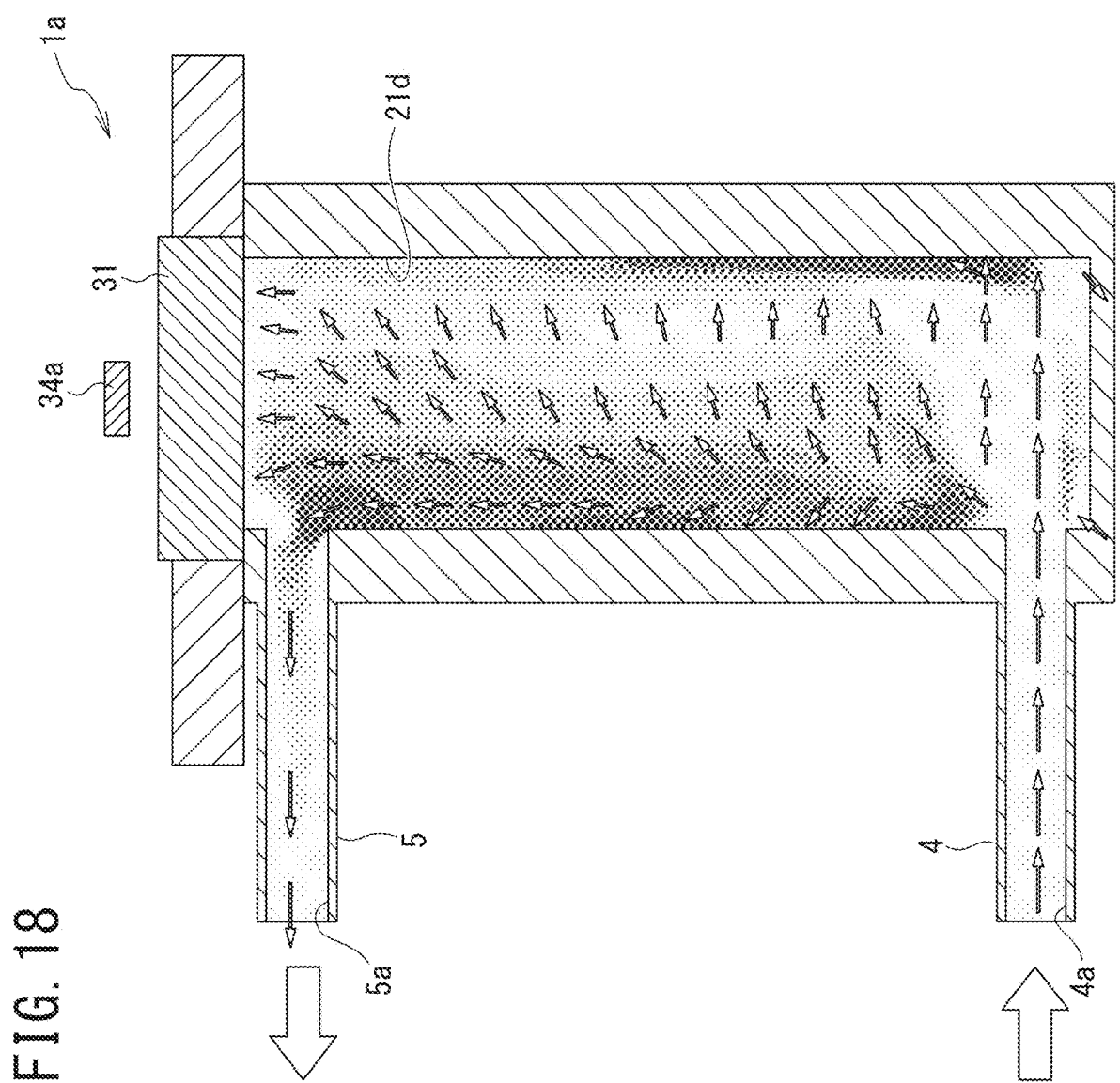
FIG. 18 illustrates one example of a flow velocity distribution of a fluid sterilization module in Comparative Example A of the first embodiment.

FIG. 18 illustrates a flow velocity distribution in a fluid sterilization module 1a not including the first chamber 26, as Comparative Example. The fluid sterilization module 1a as Comparative Example does not include both the first chamber 26 and the second chamber 27. Additionally, the inflow portion 4 and the outflow portion 5, respectively, are provided at both ends of the inner cylinder 21.

As illustrated in FIG. 18, in the flow velocity distribution in the processing flow path 21d of the fluid sterilization module 1a as Comparative Example, flow velocity is higher in the vicinity of the wall surface than in the center portion, so that sufficient sterilization performance cannot be obtained.

Example A1

Figure 19:
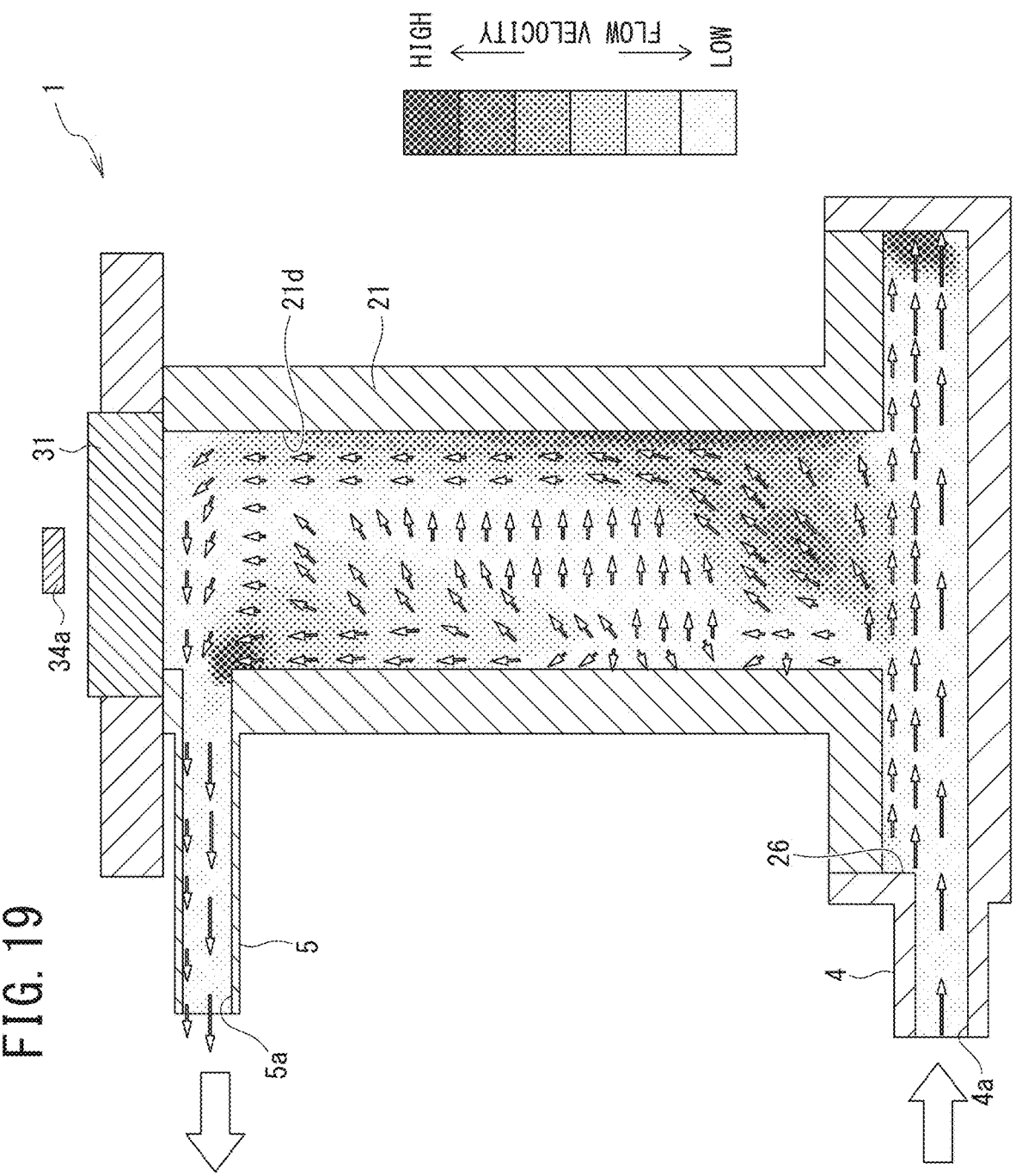
FIG. 19 illustrates one example of a flow velocity distribution of a fluid sterilization module in Example A1 of the first embodiment.

As illustrated in FIG. 19, a fluid sterilization module 1 of Example A1 is a module in which the first chamber 26 is provided in the fluid sterilization module 1a of Comparative Example.

It can be seen that flow velocity variation in the vicinity of the center portion of the processing flow path 21d is suppressed, as illustrated in FIG. 19.

Example A2

Figure 20:
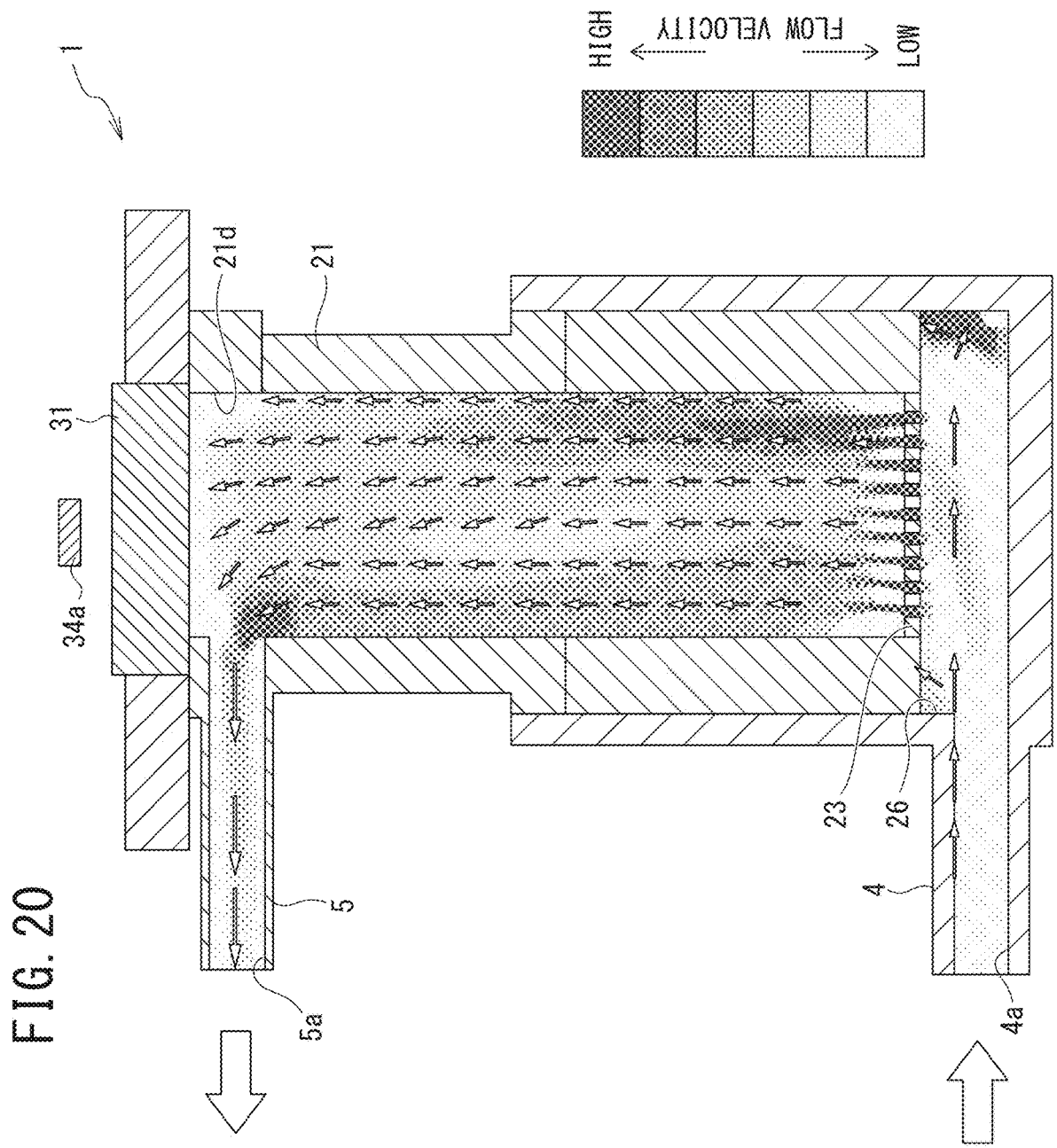
FIG. 20 illustrates one example of a flow velocity distribution of a fluid sterilization module in Example A2 of the first embodiment.

A fluid sterilization module 1 of Example A2 is a module in which the plate 23 is further provided on an inflow side of the processing flow path 21d in the fluid sterilization module 1 of Example A1, as illustrated in FIG. 20.

As illustrated in FIG. 20, it can be seen that flow directions in the processing flow path 21d are aligned as compared with Example A1.

Example A3

Figure 21:
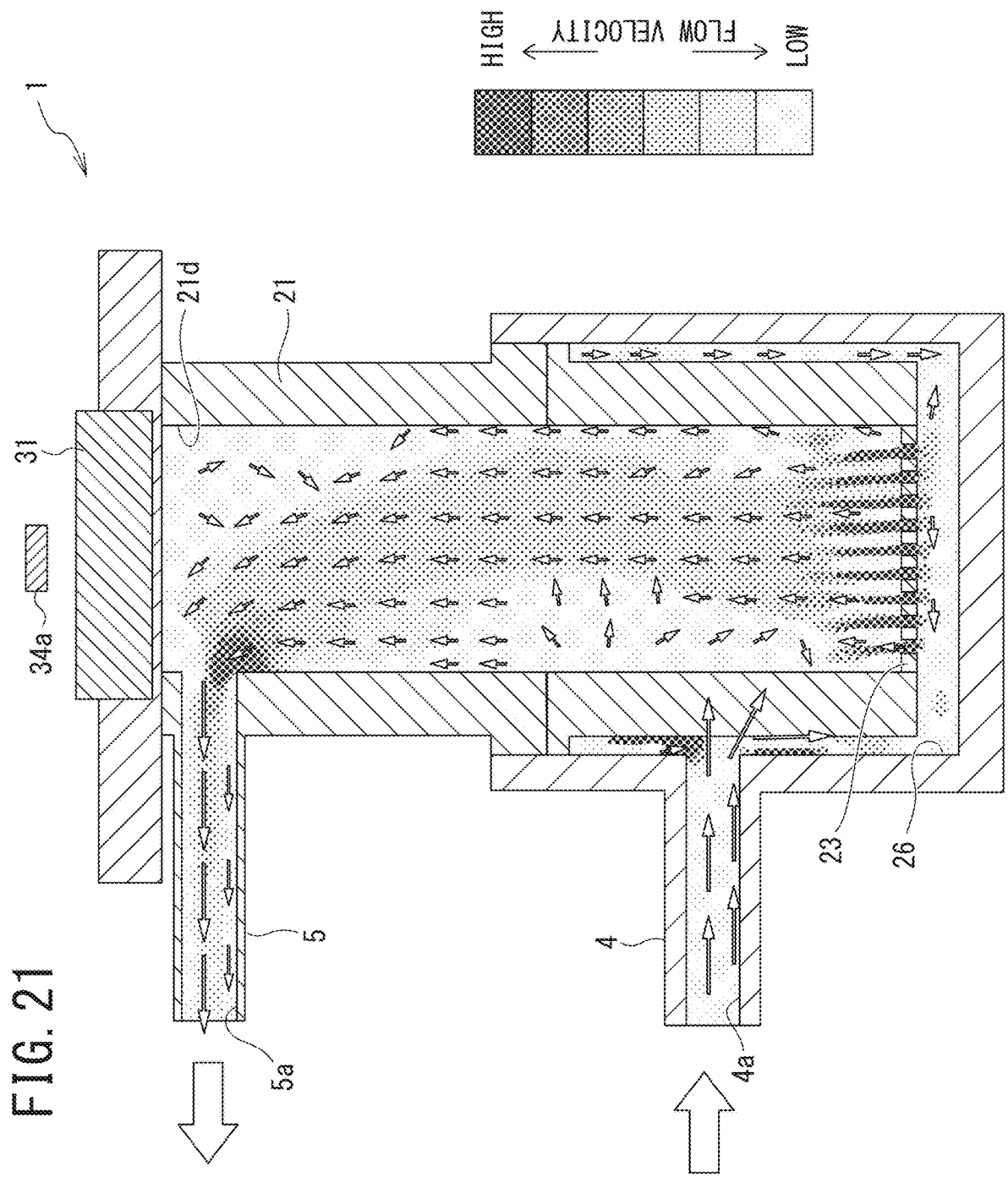
FIG. 21 illustrates one example of a flow velocity distribution of a fluid sterilization module in Example A3 of the first embodiment.

In a fluid sterilization module 1 of Example A3, the inflow portion 4 is moved at a position close to a longitudinal center of the processing flow path 21d in the fluid sterilization module 1 of Example A2, as illustrated in FIG. 21.

As illustrated in FIG. 21, it can be understood that moving the inflow portion 4 to the position close to the longitudinal center of the processing flow path 21d leads to further suppression of flow velocity variation in the processing flow path 21d.

Example A4

Figure 22:
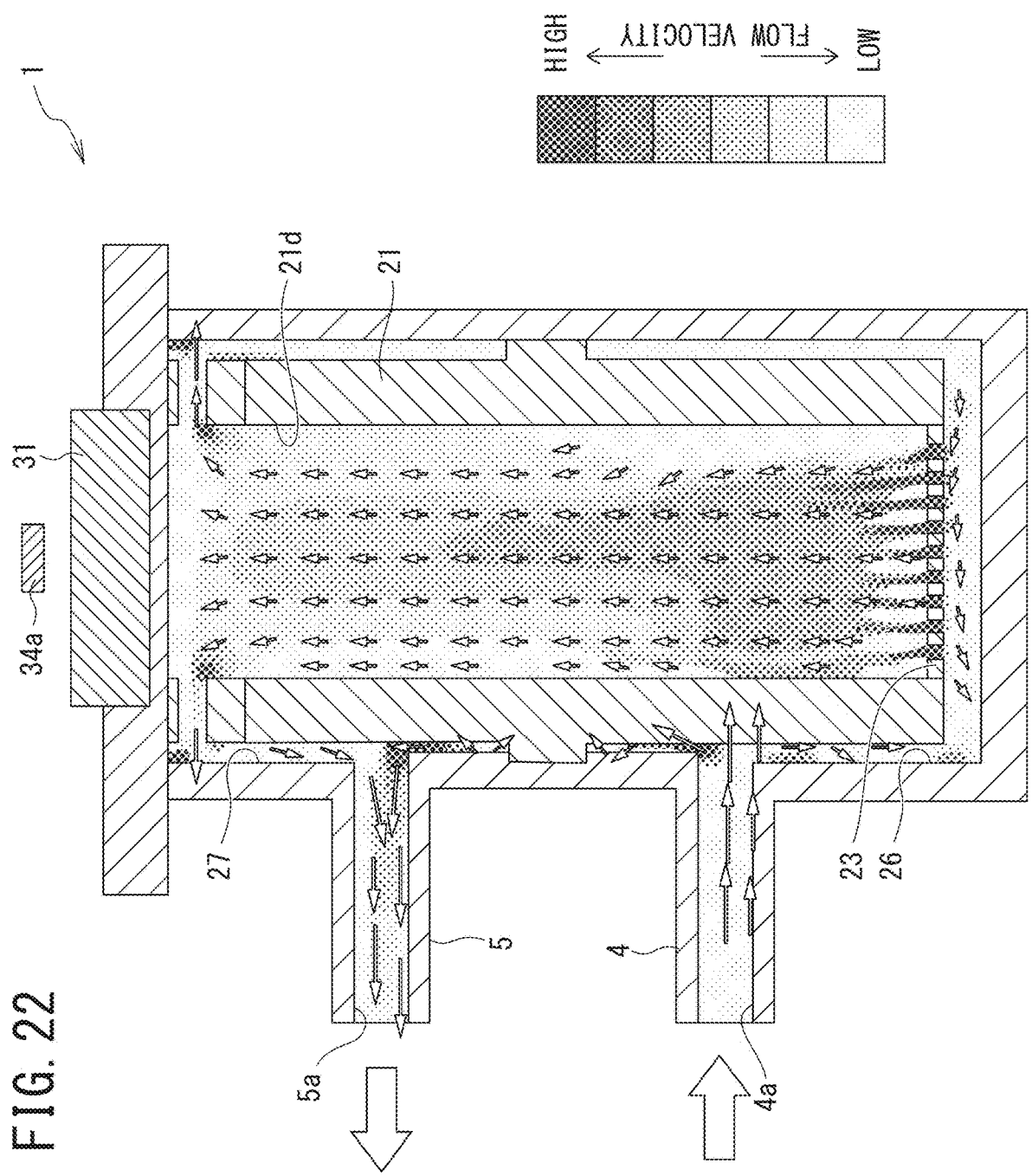
FIG. 22 illustrates one example of a flow velocity distribution of a fluid sterilization module in Example A4 of the first embodiment.

In a fluid sterilization module 1 of Example A4, the second chamber 27 is further provided, and the outflow portion 5 is moved at a position close to the longitudinal center of the processing flow path 21d in the fluid sterilization module 1 of Example A3, as illustrated in FIG. 22.

As illustrated in FIG. 22, it can be understood that providing the second chamber 27 in addition to the first chamber 26 and furthermore moving the inflow portion 4 and the outflow portion 5 at the positions close to the longitudinal center of the processing flow path 21d lead to further suppression of flow velocity variation in the processing flow path 21d, and also the flow directions are further aligned in one direction.

Example B

Sterilization efficiency of the fluid sterilization module 1 according to the first embodiment was measured.

Measurement of the sterilization efficiency was performed using a solution at 25° C. and with a transmittance of 97%/cm, containing *E. Coli* NBRC 3972 ($1 \times 10^6$ CFU/ml). The solution was introduced at a flow velocity of 2.0 L/min from the inflow portion 4. In addition, the light source 34 included two light emitting elements 34a, and light sources used as the light emitting elements 34a emitted ultraviolet light of 35 mW when a pulsed current of 1 millisecond at 500 mA was supplied. Light emission measurement using the pulsed current was for checking optical output power of the light emitting elements, regardless of heat, and sterilization was performed by continuous light emission with continuous current. As sterilization efficiency, residual bacteria (%) and logarithmic reduction value (LRV) were measured. The LRV is a value calculated by the following formula (2):

$$\text{LRV} = -\log(\text{number of bacteria in sterilized solution} \div \text{number of bacteria in raw liquid (solution)}) \quad (2)$$

Note that the following FIGS. 23 to 27 each simply illustrate the fluid sterilization module 1.

Example B1

Figure 23:
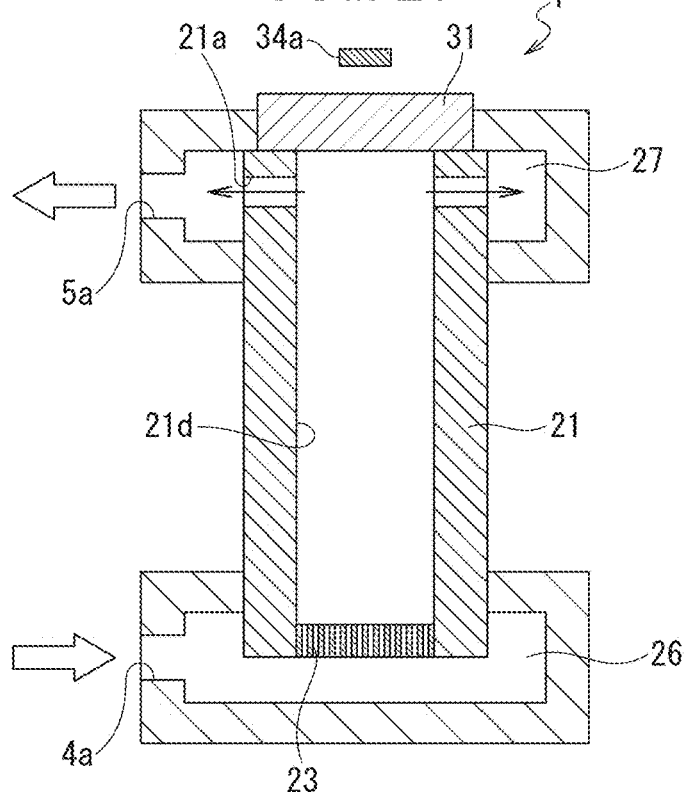
FIG. 23 is a structural diagram illustrating the outline of a fluid sterilization module in Example B1 of the first embodiment.

In a fluid sterilization module 1 of Example B1, the first chamber 26 and the second chamber 27 are provided at an end on the inflow portion 4 side and an end of the outflow portion 5 side of the inner cylinder 21, as illustrated in FIG. 23. The first chamber 26 and the second chamber 27 are respectively formed as separate ones, and provided only at portions close to the ends in such a manner as to surround the opening and the outer peripheral surface, respectively, on the inflow portion 4 side and the outflow portion 5 side of the inner cylinder 21. Additionally, at the opening of the inflow portion 4 side of the inner cylinder 21 is provided the plate 23.

Example B2

Figure 24:
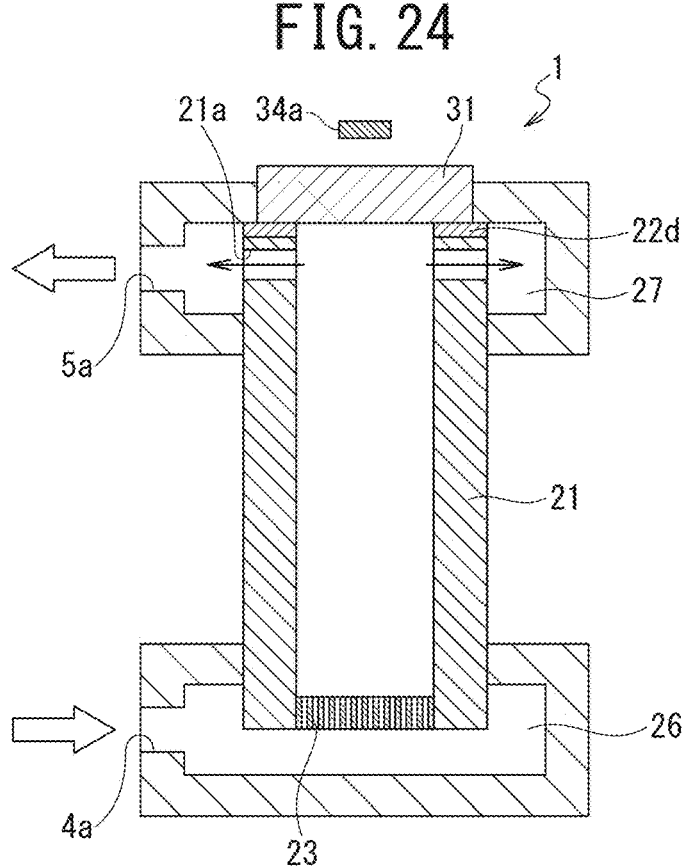
FIG. 24 is a structural diagram illustrating the outline of a fluid sterilization module in Example B2 of the first embodiment.

A fluid sterilization module 1 of Example B2 is the fluid sterilization module 1 of Example B1 in which the elastic sheet 22d is provided between the window portion 31 including the window 33 formed using quartz glass or the like and an end face of the inner cylinder 21, as illustrated in FIG. 24.

Example B3

Figure 25:
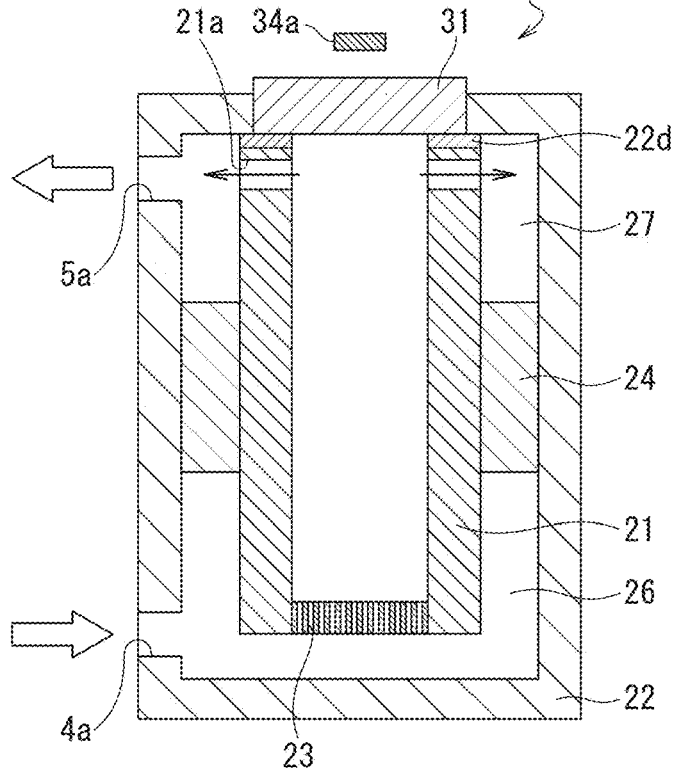
FIG. 25 is a structural diagram illustrating the outline of a fluid sterilization module in Example B3 of the first embodiment.

A fluid sterilization module 1 of Example B3 corresponds to the fluid sterilization module 1 illustrated in FIGS. 2A and 2B, as illustrated in FIG. 25.

Comparative Example B1

Figure 26:
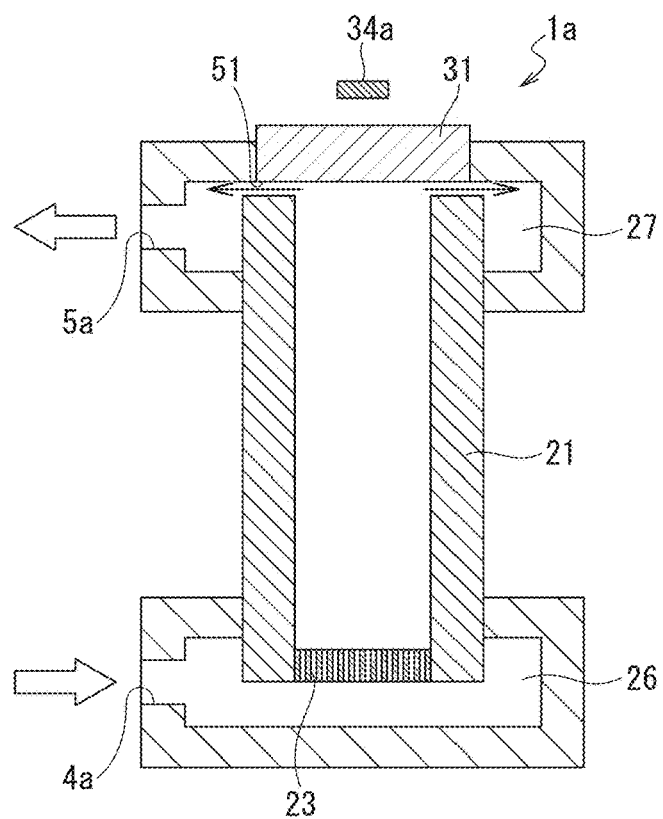
FIG. 26 is a structural diagram illustrating the outline of a fluid sterilization module in Comparative Example B1 of the first embodiment.

A fluid sterilization module 1a of Comparative Example B1 is the fluid sterilization module 1 of Example B1 illustrated in FIG. 23 in which a gap 51 in place of the communication port 21a is provided between the inner cylinder 21 and the window portion 31 to allow an object having passed through the processing flow path 21d to flow out from the outflow portion 5 via the gap 51, as illustrated in FIG. 26.

Comparative Example B2

Figure 27:
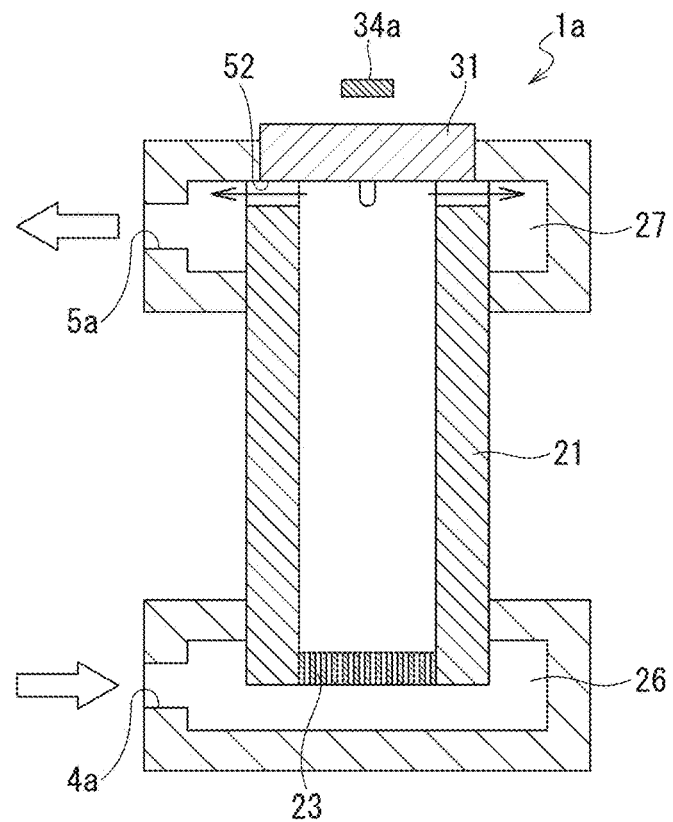
FIG. 27 is a structural diagram illustrating the outline of a fluid sterilization module in Comparative Example B2 of the first embodiment.

A fluid sterilization module 1a of Comparative Example B2 is the fluid sterilization module 1a of Comparative Example B1 illustrated in FIG. 26 in which, instead of the gap 51, a groove portion 52 oriented radially is provided at an end of the inner cylinder 21 on the window portion 31 side to allow an object having passed through the processing flow path 21d to flow out from the outflow portion 5 through a flow path formed between the window portion 31 and the groove portion 52 of the inner cylinder 21, as illustrated in FIG. 27.

[Sterilization Efficiency]

Table 3 depicts measurement results of sterilization efficiency in Examples B1 to B3 and Comparative Examples B1 and B2.

As can be seen in Table 3, residual bacteria (%) in the fluid sterilization modules 1 of Examples B1 to B3 were significantly reduced as compared with those in the fluid sterilization modules 1a of Comparative Examples B1 and B2. In addition, similarly, LRV is found to be higher in the fluid sterilization modules 1 of Examples B1 to B3 than the fluid sterilization modules 1a of Comparative Examples B1 and B2.

TABLE 3

|  | Ex. B1 | Ex. B2 | Ex. B3 | Comp. Ex. B1 | Comp. Ex. B2 |
| --- | --- | --- | --- | --- | --- |
| Residual bacteria (%) | 0.00038% | 0.00031% | 0.000083% | 3.8% | 0.037% |
| LRV | 5.4 | 5.5 | 6.1 | 1.4 | 3.4 |

Example C

Regarding the fluid sterilization module 1 according to the first embodiment, fluid simulation was performed.

Figure 28:
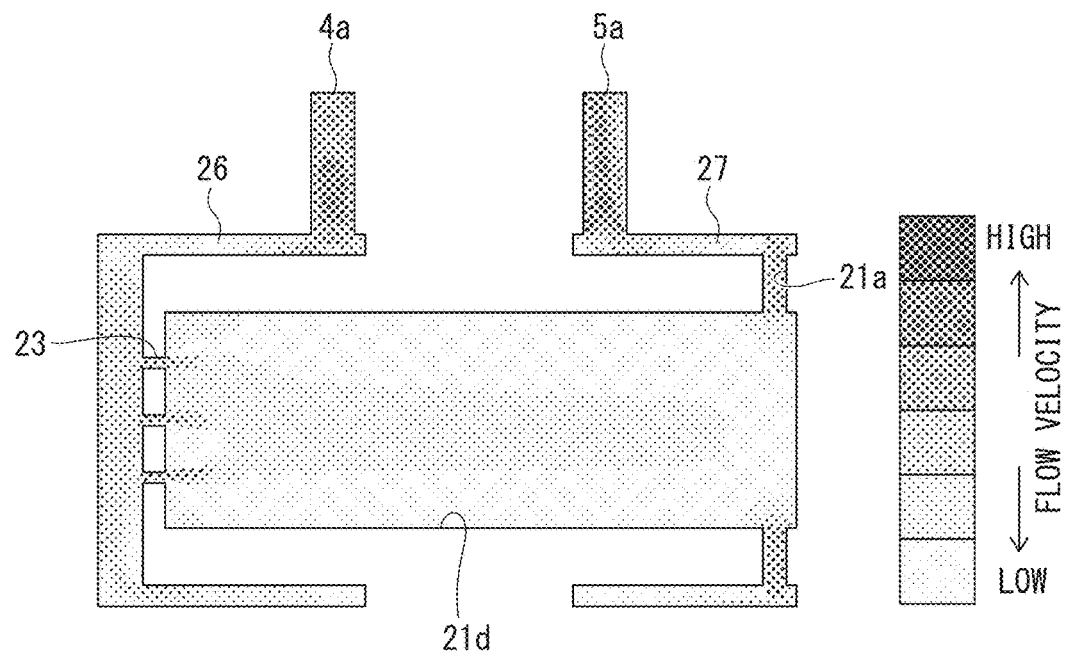
FIG. 28 illustrates one example of results of fluid simulation using the fluid sterilization module according to the first embodiment.

FIG. 28 illustrates fluid simulation results of the fluid sterilization module 1 according to the first embodiment of the present invention.

As illustrated in FIG. 28, turbulence was confirmed to occur at a relatively low flow velocity (e.g., flow velocity>about 1 m/s) in the first chamber 26. In other words, it was confirmed that biofilm formation hardly occurs. Note that FIG. 28 simply illustrates the fluid sterilization module 1.

Example D

In a fluid sterilization module 1 according to the first embodiment, simulation on computer was performed regarding a relationship between the inner volume of the first chamber 26 and sterilization performance by ultraviolet light.

Figure 29A:
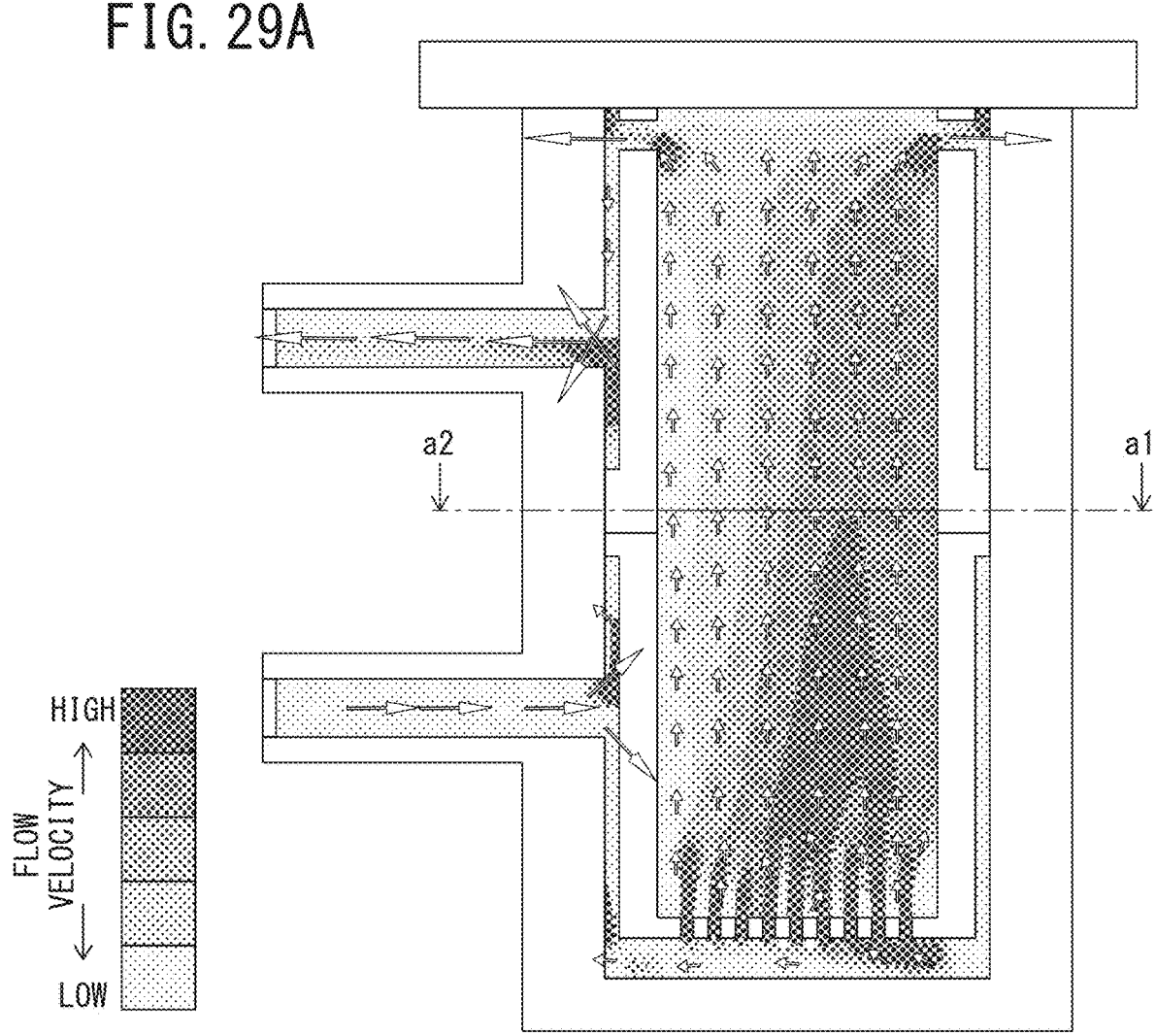
FIGS. 29A and 29B illustrate one example of results of fluid simulation using the fluid sterilization module according to the first embodiment.
Figure 29B:
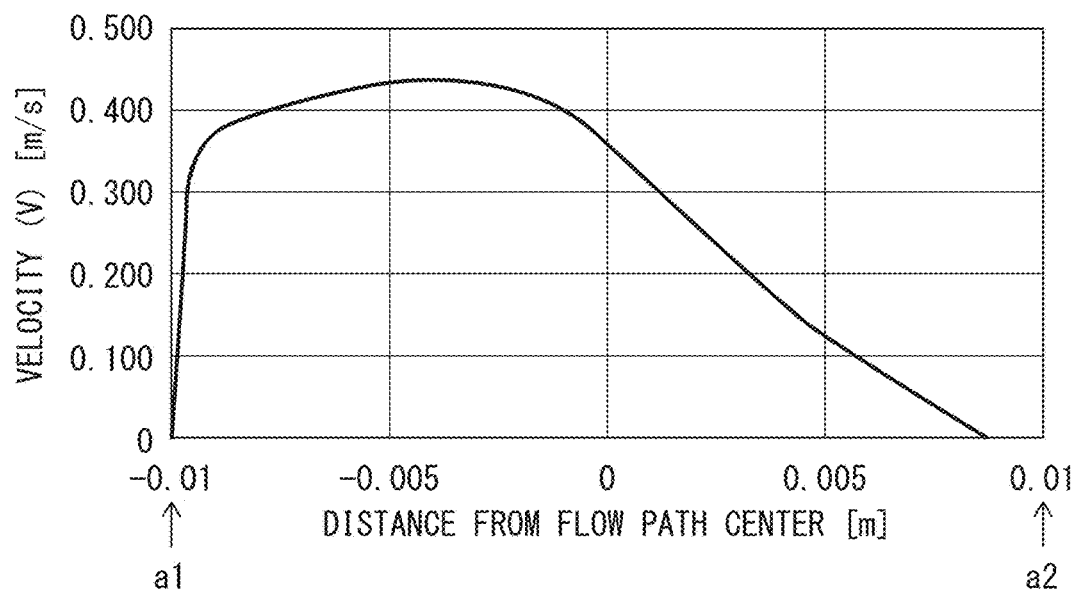
Figure 30A:
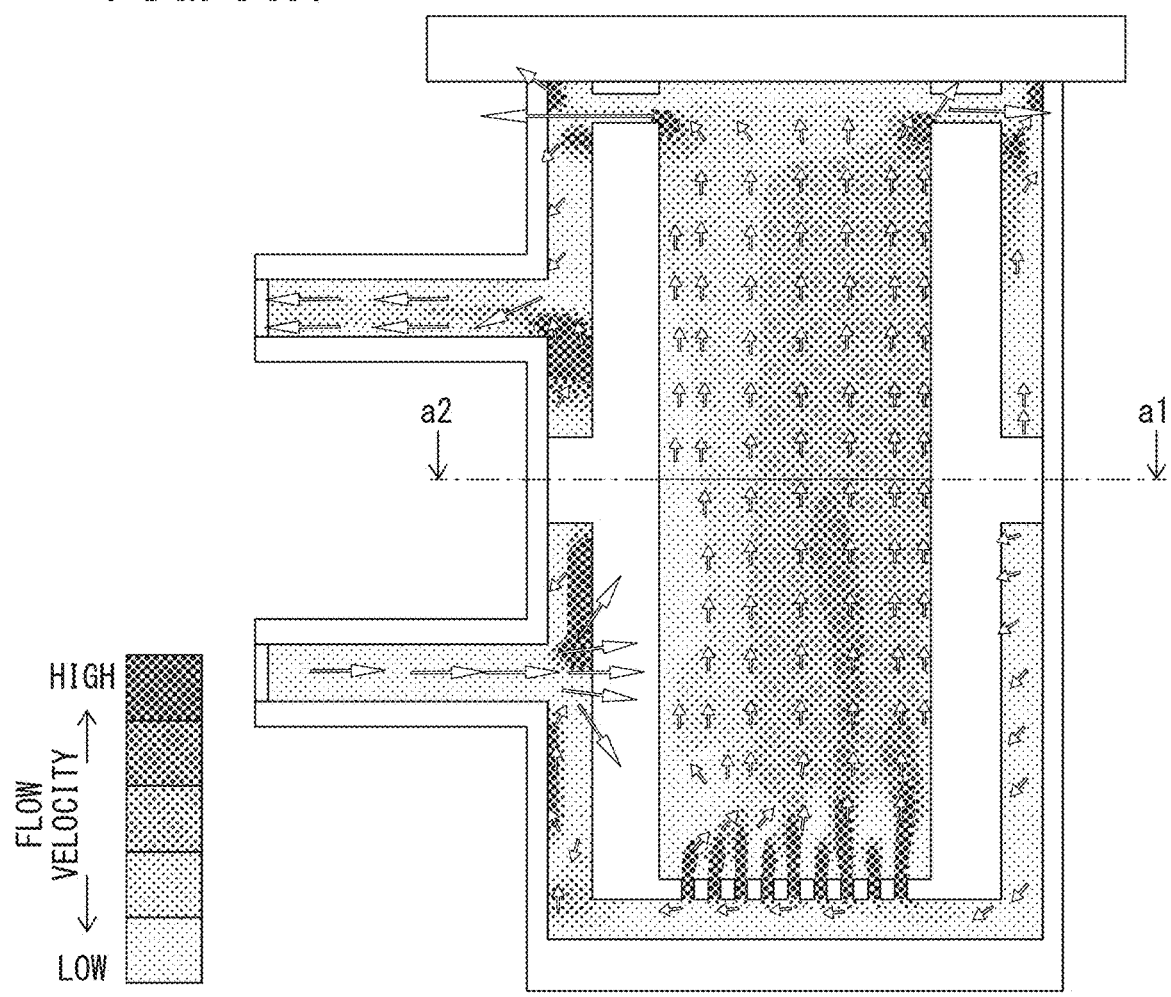
FIGS. 30A and 30B illustrate one example of results of fluid simulation using the fluid sterilization module according to the first embodiment.
Figure 30B:
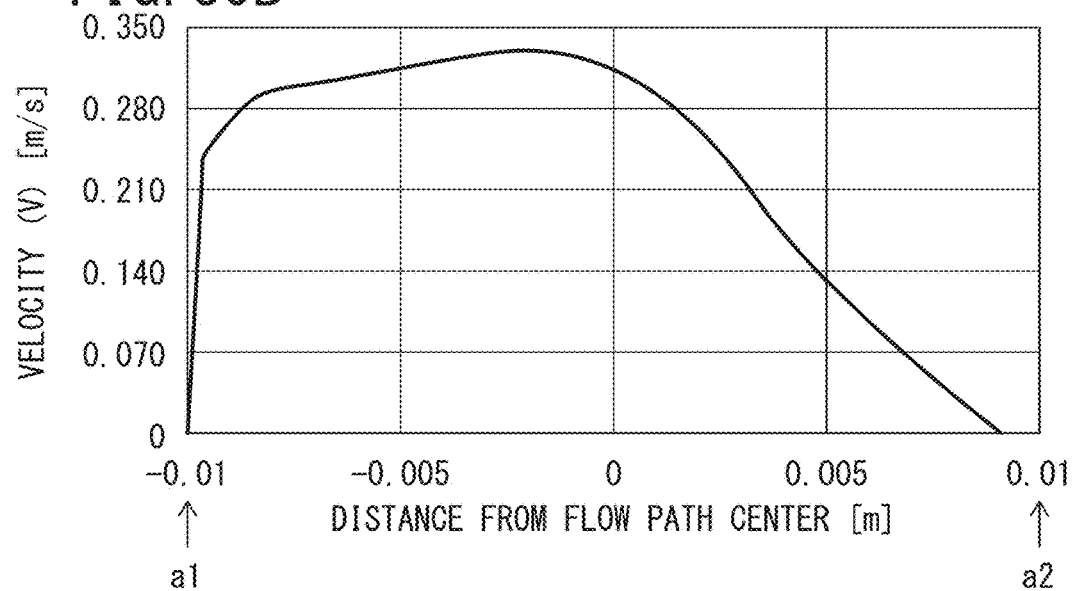
Figure 31A:
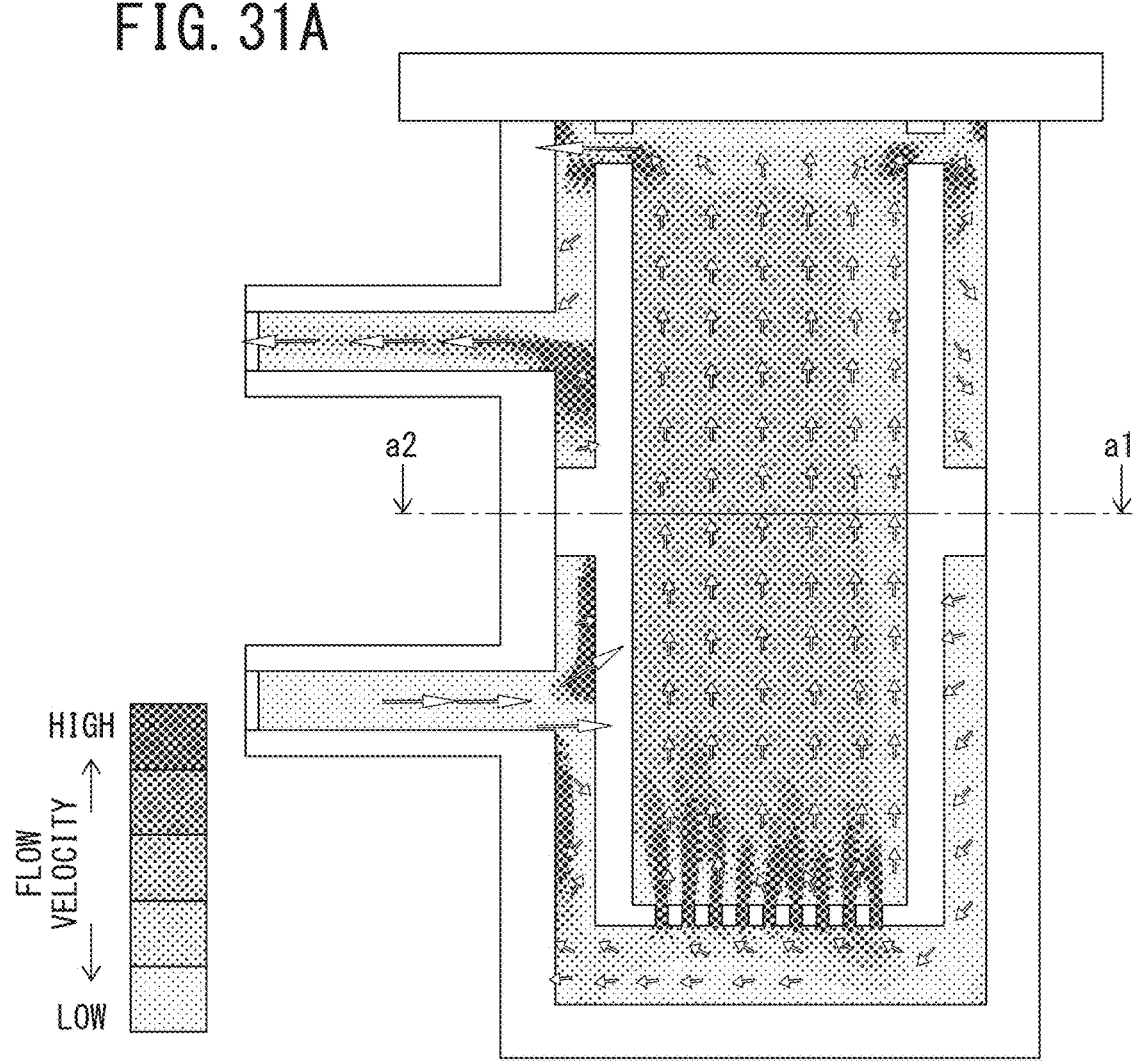
FIGS. 31A and 31B illustrate one example of results of fluid simulation using the fluid sterilization module according to the first embodiment.
Figure 31B:
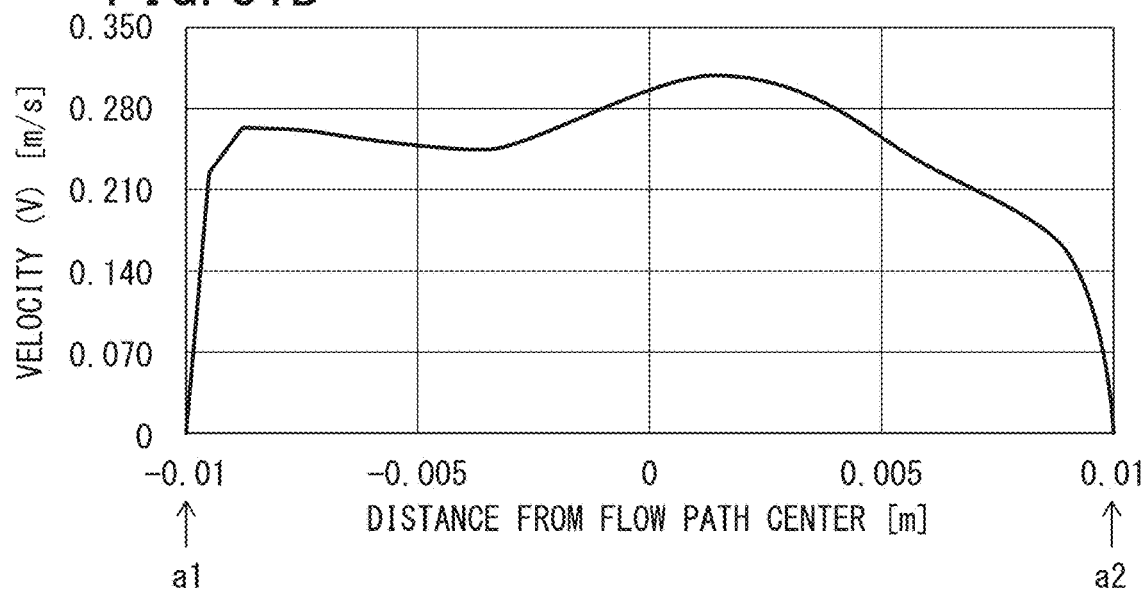

FIGS. 29A, 29B, 30A, 30B, 31A, and 31B illustrate simulation results in cases where a magnification of the volume of the first chamber 26 with respect to the cube of the equivalent inner diameter of the processing flow path 21d is 0.51 (FIGS. 29A and 29B), 1.46 (FIGS. 30A and 30B), and 1.51 (FIGS. 31A and 31B). FIGS. 29A, 30A, and 31A each illustrate a flow velocity distribution in the processing flow path 21d of the fluid sterilization module 1 according to the first embodiment. Note that FIGS. 29A, 29B, 30A, 30B, 31A, and 31B simply illustrate the fluid sterilization module 1. Additionally, arrows in the drawings indicate flow directions. In addition, FIGS. 29B, 30B, and 31B each illustrate flow velocity [m/s] in the processing flow path 21d, in which the horizontal axis represents distance [m] from a processing flow path center in a cross section taken along line a1-a2 at a substantially center position in the longitudinal direction of the processing flow path 21d, and the vertical axis represents flow velocity [m/s].

The fluid simulation results illustrated in FIGS. 29A, 29B, 30A, 30B, 31A, and 31B indicate that when the magnification of the volume of the first chamber 26 with respect to the cube of the equivalent inner diameter of the processing flow path 21d is larger, the flow distribution in the processing flow path 21d is more uniform.

Figure 32:
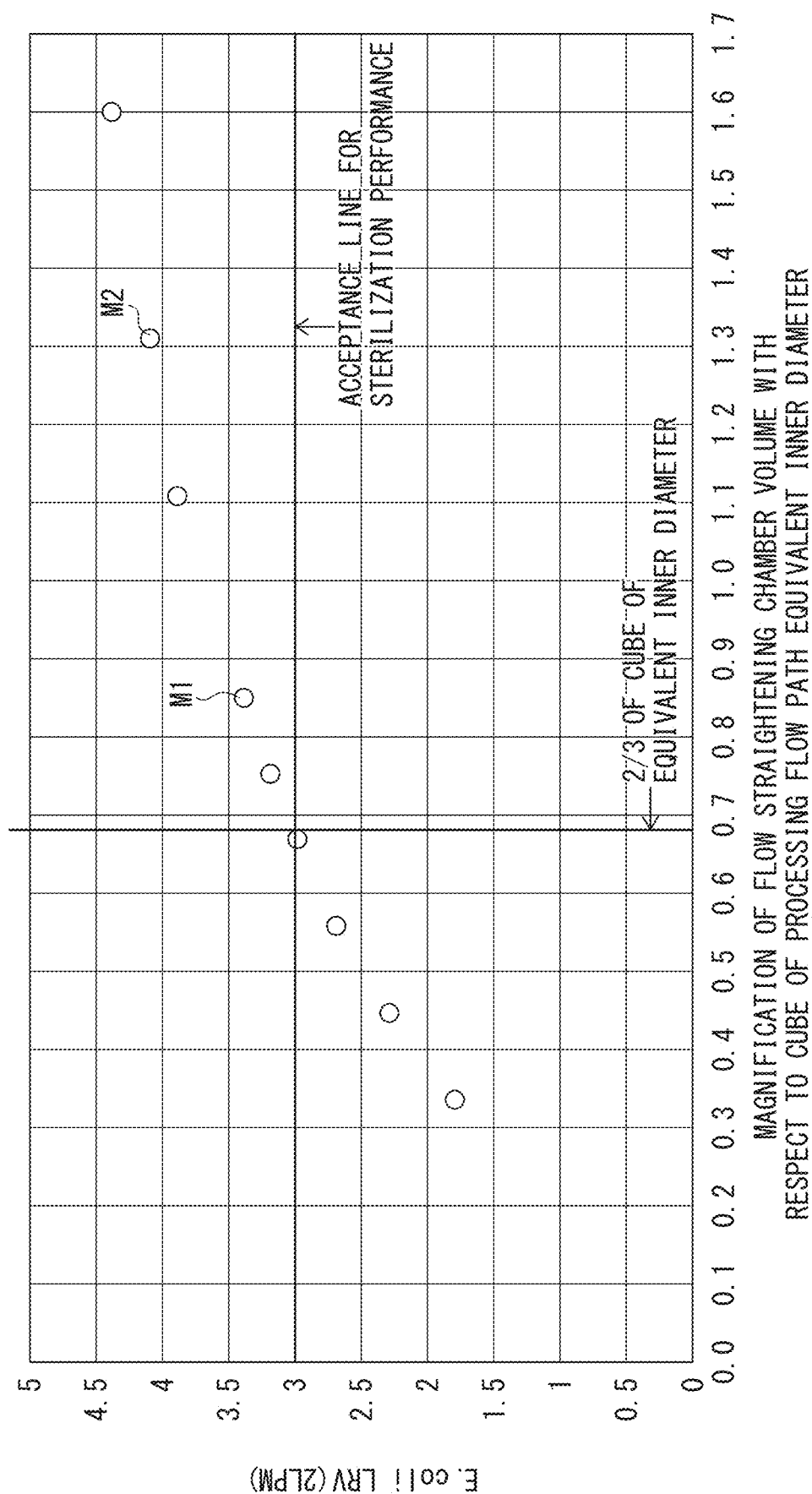
FIG. 32 illustrates one example of results of simulation using the fluid sterilization module according to the first embodiment.

FIG. 32 illustrates simulation results indicating a correspondence between the volume of the first chamber 26 and LRV, in which the horizontal axis represents magnification with respect to the cube of the equivalent inner diameter of the processing flow path 21d, and the vertical axis represents LRV obtained when a bacterial solution containing $E.\ Coli$ NBRC 3972, as a fluid to be sterilized, was flown into the processing flow path 21d at a flow velocity of 2 L/min. Note that, in the fluid sterilization module 1 illustrated in FIGS. 2A and 2B, two UVC-LEDs with an output power of 28 mW were used as the light emitting elements 34a.

The results show, as illustrated in FIG. 32, that LRV becomes larger as the volume of the first chamber 26 increases. In addition, it is found that when the acceptance line for sterilization performance is set to LRV=3, LRV≥3 is satisfied if the volume of the first chamber 26 is equal to or more than about ⅔ (about 0.67) of the cube of the equivalent inner diameter of the processing flow path 21d.

Figure 33:
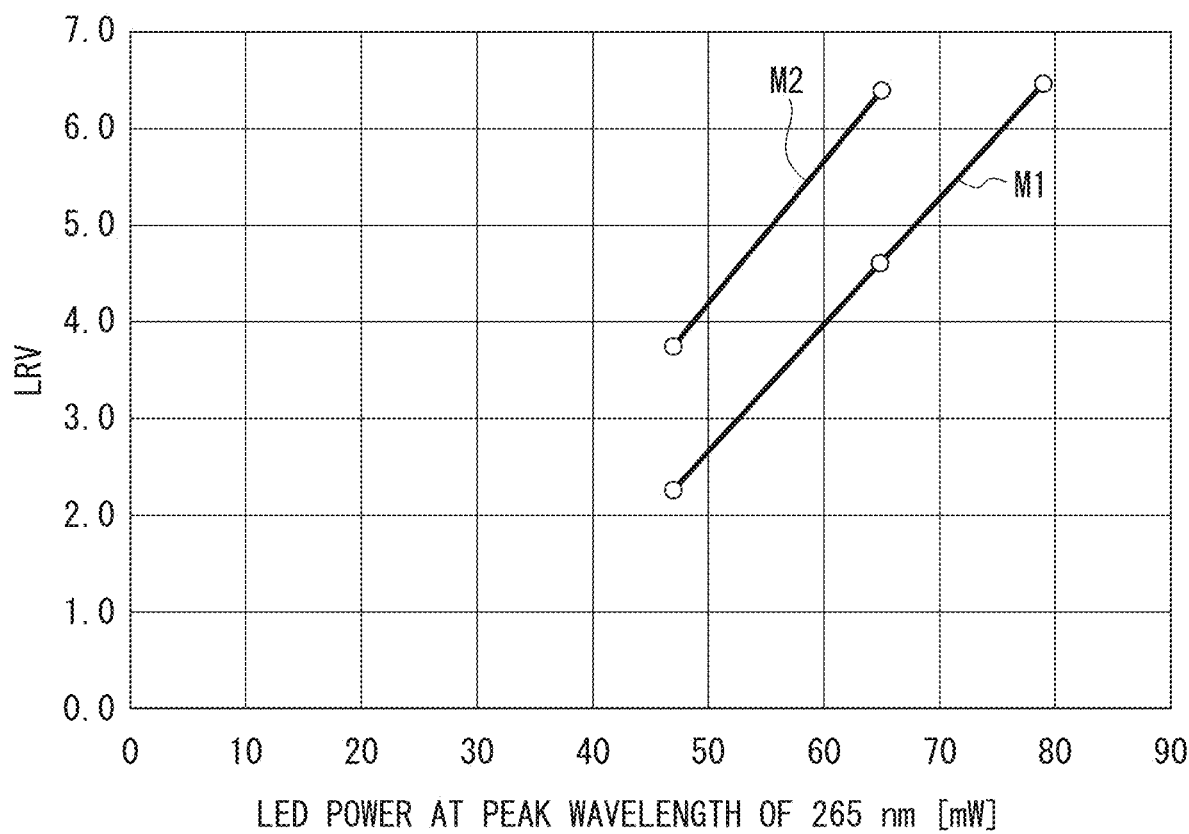
FIG. 33 illustrates one example of results of sterilization tests performed using the fluid sterilization module according to the first embodiment.

Next, regarding estimation points M1 and M2 in the simulation results illustrated in FIG. 32, sterilization tests were actually performed using the fluid sterilization module 1 illustrated in FIGS. 2A and 2B. FIG. 33 illustrates the results.

Note that a magnification at the estimation point M1 with respect to the cube of the equivalent inner diameter of the processing flow path 21d was 0.85, and a magnification at the estimation point M2 with respect thereto was 1.31.

Additionally, in the fluid sterilization module 1 illustrated in FIGS. 2A and 2B, two UVC-LEDs were used as the light emitting elements 34a.

LRV obtained when optical output powers of the UVC-LEDs at a peak wavelength of 265 nm were 79.0 mW, 64.9 mW, and 46.9 mW were measured regarding each of the estimation points M1 and M2.

In FIG. 33, the horizontal axis represents optical output power [mW] of the UVC-LEDs at the peak wavelength of 265 [nm], and the vertical axis represents sterilization performance (LRV) against $E.\ Coli$ NBRC 3972 at the flow rate of 2 L/min.

FIG. 33 indicates that sterilization performance (LRV) corresponding to an LED output power of 56 mW from the two 28 mW LEDs has achieved results equal to or more than the simulation results illustrated in FIG. 32.

Example E

Regarding the fluid sterilization module 201 according to the second embodiment of the present invention, optical simulation and flow velocity simulation on computer were performed.

Figure 34A:
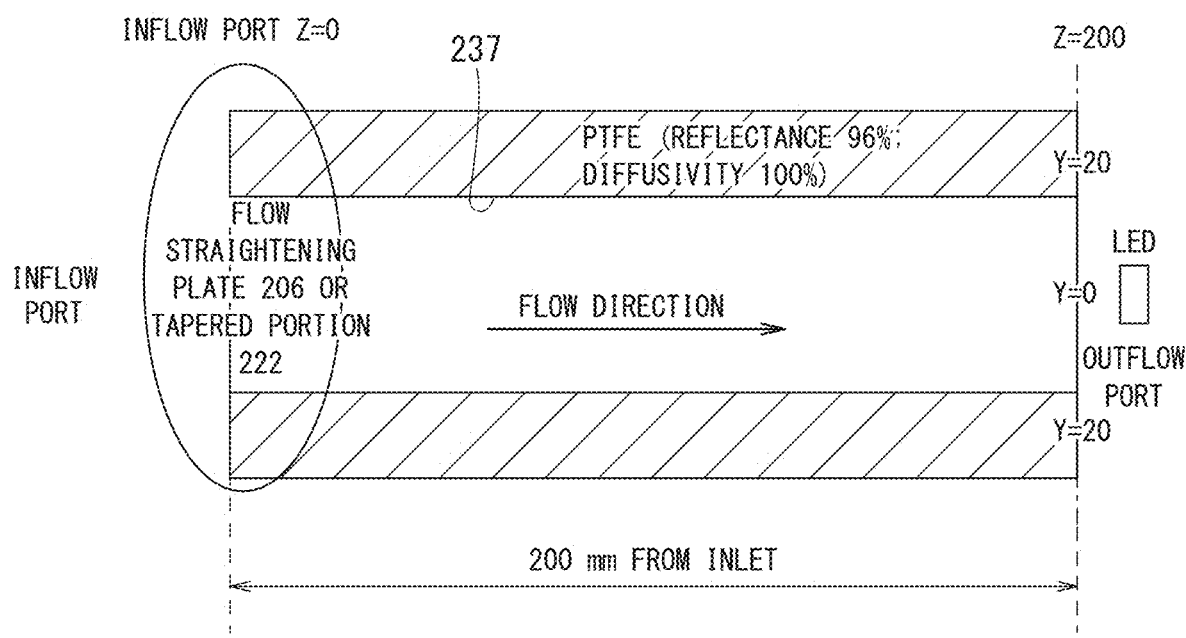
FIGS. 34A and 34B illustrate one example of an inner flow path of the fluid sterilization module according to the second embodiment assumed in performing simulation on computer.

In the optical simulation and the flow velocity simulation, simulation on computer was performed by assuming the inside of a straight tube having a circular cross-section illustrated in FIG. 34A, as an inner flow path 237.

Specifically, a straight tube having a tubular diameter of 40 mm and a length of 300 mm was assumed. As conditions for allowing an object to flow, a flow rate of 5 L/min, an average flow velocity of 0.07 m/s, and a Reynolds number of 2957 were set, and turbulence was produced. Additionally, an inlet zone distance of from 1000 mm to 1600 mm was set.

Additionally, the straight tube was formed using polytetrafluoroethylene, whose reflectance in an ultraviolet light region was 96% and whose diffusivity in the ultraviolet light region was 100%.

[Optical Simulation]

Figure 34B:
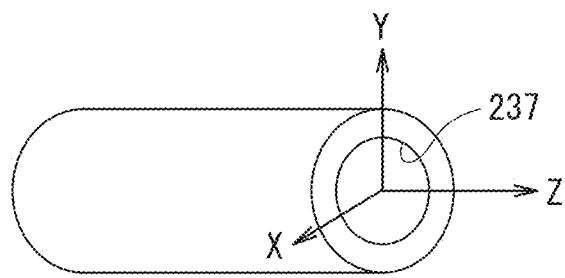

In a flow path formed by such a straight tube, optical evaluation was performed on an object in a cross-section at a point located 200 mm toward a downstream side from an inflow port-side end of the straight tube. Note that, in FIG. 34A, an extending direction of the straight tube was defined as a Z axis, as illustrated in FIG. 34B. Additionally, a direction perpendicular to the Z axis with reference to a circular center in the cross-section, i.e., a tube center (an upward direction in FIG. 34B) was defined as a Y axis, and a direction perpendicular to the Z axis and the Y axis, similarly, with reference to the tube center, was defined as an X axis direction, in which coordinates of the X axis and the Y axis at the tube center were set as X=0 and Y=0, respectively. In the XYZ coordinate system, respective points at each interval of 0.5 mm in a range of from Y=−20 mm to +20 mm on the Y axis passing through Z=200 mm and X=0 were set as estimation points. Regarding the respective estimation points, dose equivalent value: "ultraviolet light intensity×(1/flow velocity)" (hereinafter referred to also as "ultraviolet light intensity ratio") was calculated.

In the cross-section passing through Z=200 and X=0, if the distribution of the ultraviolet light intensity ratio of 40 estimation points is uniform in a range of from the tube center (X=0, Y=0, and Z=200) to a peripheral edge of the straight tube, efficiency can be considered favorable. Conversely, if there is any variation in the range from the tube center to the peripheral edge of the straight tube, efficiency can be considered poor.

Then, optical simulation was performed to estimate a standard deviation of the ultraviolet light intensity ratio of the 40 estimation points, followed by evaluation.

Figure 35A:
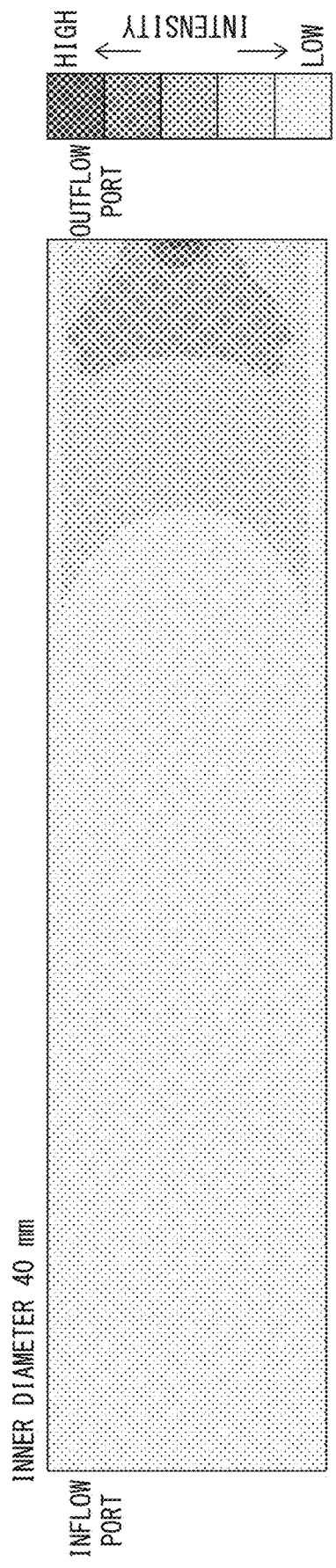
FIGS. 35A and 35B illustrate one example of results of optical simulation using the fluid sterilization module according to the second embodiment.
Figure 35B:
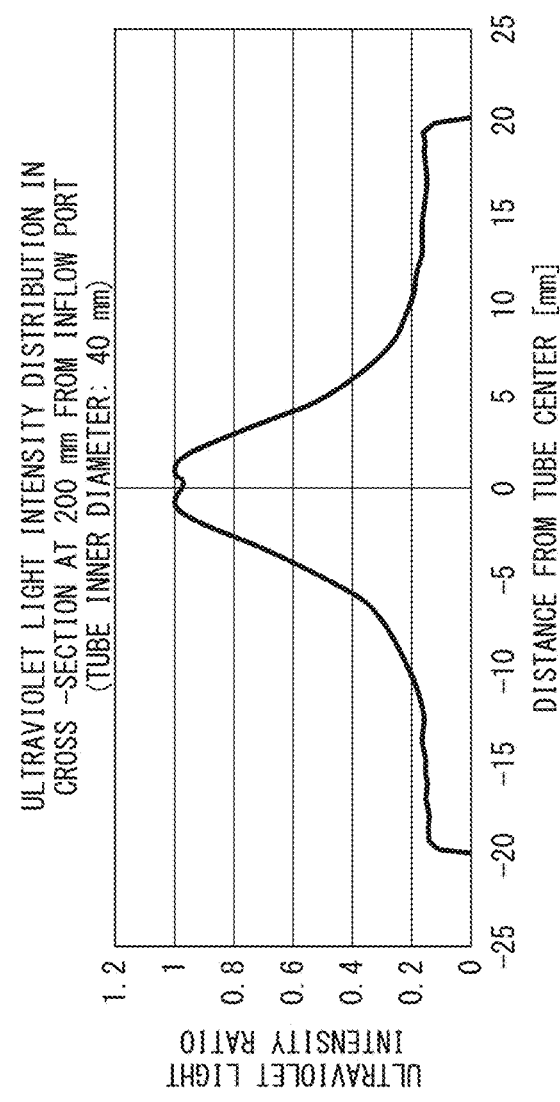
Figure 37A:
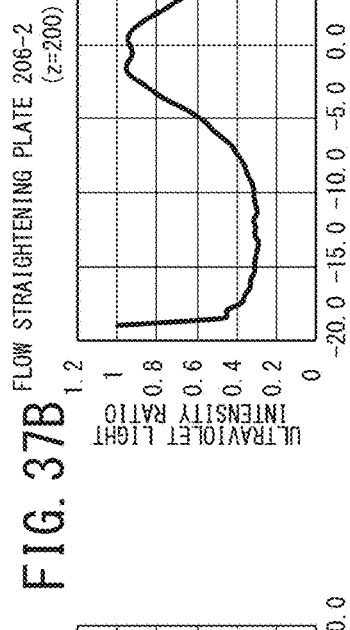
FIGS. 37A to 37F illustrate one example of ultraviolet light intensity ratios in flow velocity simulation using the fluid sterilization module according to the second embodiment.
Figure 37B:
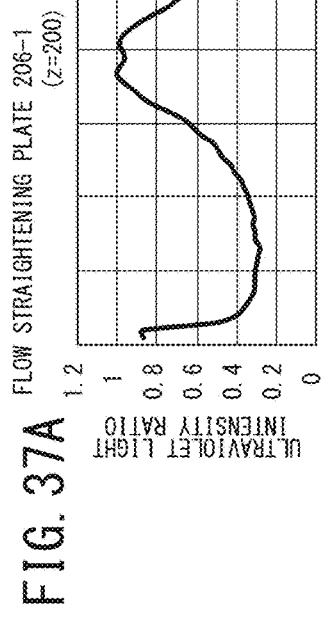
Figure 37C:
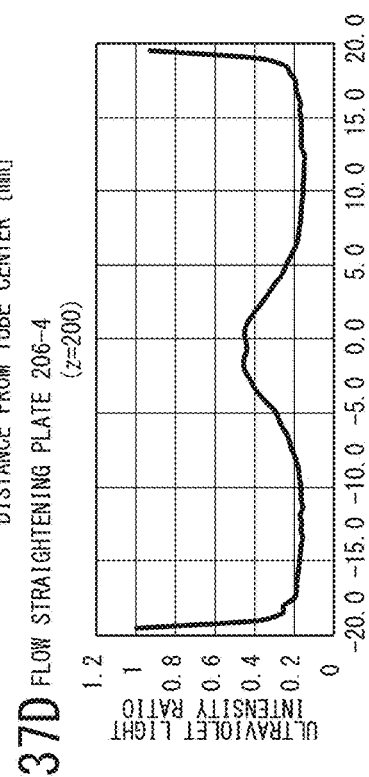
Figure 37D:
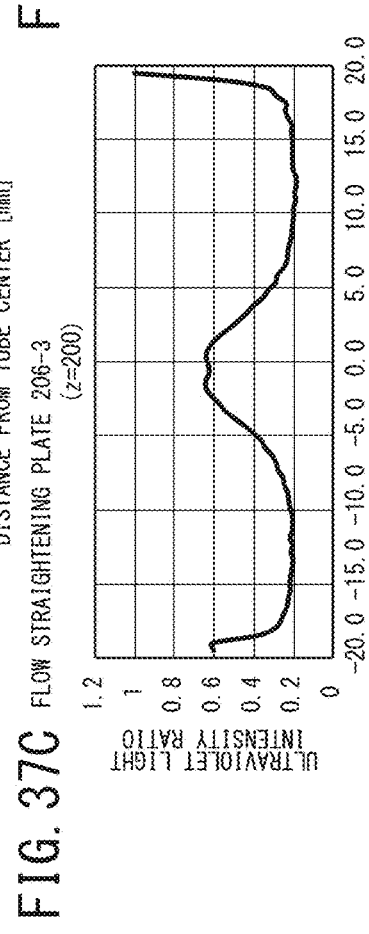
Figure 37E:
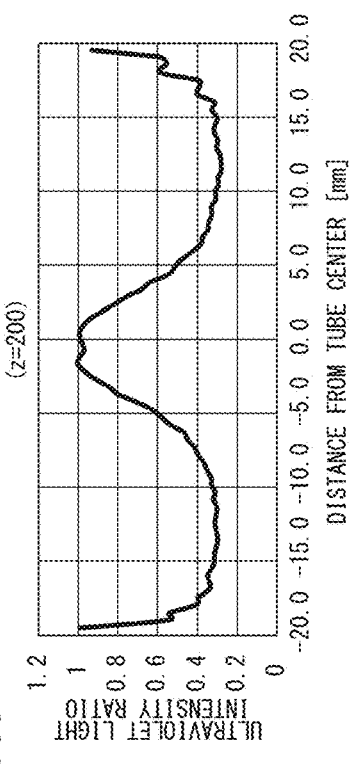
Figure 37F:
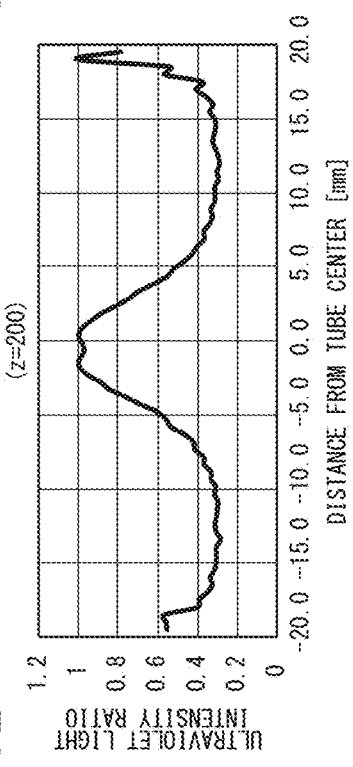

FIG. 35A illustrates an ultraviolet light distribution in a range of from the inflow-side end to the outflow-side end of the straight tube assumed in FIG. 34A, obtained as the results of the optical simulation. Additionally, FIG. 35B illustrates ultraviolet light intensity ratios in the cross-section passing through Z=200 mm and X=0 of the flow path using the straight tube assumed in FIG. 34A. The horizontal axis represents distance [mm] in the Y axis direction from the tube center (X=0, Y=0, and Z=200) in the cross-section, and the vertical axis represents ultraviolet light intensity ratio.

As illustrated in FIG. 35B, it can be seen that, in the cross-section passing through Z=200 and X=0, the ultraviolet light intensity ratio is the highest in the vicinity of the tube center, and becomes smaller at positions closer to the peripheral edge.

[Flow Velocity Simulation (Flow Straightening Plate)]

Using the straight tube assumed in FIG. 34A, flow velocity simulation on computer was performed regarding cases where plates 206-1 to 206-6 were provided as the plate 206. Note that the tapered portion 222 was not provided.

As the plate 206, there were used the six plates 206-1 to 206-6 different in aperture ratio, illustrated in FIGS. 36A to 36F. Table 4 illustrates specifications of the plates 206-1 to 206-6. Note that, similarly to FIG. 11, each of the plates 206-1 to 206-6 was divided into three regions being concentric circles and having an equal area.

value σs1 can be considered to have reduced variation in the ultraviolet light irradiation dose, thereby having improved efficiency. Conversely, in the case of a flow straightening plate having a standard deviation of the ultraviolet light intensity ratio equal to or more than the standard deviation reference value σs1, using the plate can be considered to increase variation in the ultraviolet light irradiation dose, thereby degrading efficiency.

TABLE 4

| | Flow straightening plate 206-1 | | Flow straightening plate 206-2 | | Flow straightening plate 206-3 | | Flow straightening plate 206-4 | | Flow straightening plate 206-5 | | Flow straightening plate 206-6 | |
|---|---|---|---|---|---|---|---|---|---|---|---|---|
| | Number of holes | Aperture ratio | Number of holes | Aperture ratio | Number of holes | Aperture ratio | Number of holes | Aperture ratio | Number of holes | Aperture ratio | Number of holes | Aperture ratio |
| Inner region (φ24 mm) | 93 | 5.8% | 145 | 9.1% | 165 | 10.3% | 181 | 11.3% | 165 | 10.3% | 165 | 10.3% |
| Middle region (φ33 mm) | 132 | 8.3% | 100 | 6.3% | 80 | 5.0% | 80 | 5.0% | 86 | 5.4% | 92 | 5.8% |
| Outer region (φ40 mm) | 44 | 2.3% | 24 | 1.5% | 24 | 1.5% | 24 | 1.5% | 18 | 1.1% | 16 | 1.0% |
| Total | 269 | 16.8% | 269 | 16.8% | 269 | 16.8% | 285 | 17.8% | 269 | 16.8% | 273 | 17.1% |
| Aperture ratio of inner region ÷ aperture ratio of outer region | 2 times | | 6 times | | 7 times | | 8 times | | 9 times | | 10 times | |

Using the above plates 206-1 to 206-6, flow velocity simulation was performed by assuming the straight tube illustrated in FIG. 34A, similarly to the optical simulation. In the flow velocity simulation, conditions for allowing an object to flow were the same as those in the optical simulation.

[Verification of Range of "(Aperture Ratio of Inner Region)÷(Aperture Ratio of Outer Region)"]

Regarding the same 40 estimation points as those in the optical simulation, ultraviolet light intensity ratio was calculated. FIGS. 37A to 37F illustrate results of the calculation. In each of FIGS. 37A to 37F, the horizontal axis represents distance [mm] in the Y axis direction from the tube center (X=0, Y=0, and Z=200) in the cross-section passing through Z=200 and X=0, and the vertical axis represents ultraviolet light intensity ratio.

FIG. 38 illustrates a correspondence between standard deviation of ultraviolet light intensity ratio and "(aperture ratio of inner region)+(aperture ratio of outer region)" regarding each of the plates 206-1 to 206-6.

Herein, flow velocity simulation was performed without providing the plate 206 in the straight tube assumed in FIG. 34A, and ultraviolet light intensity ratio of the above-mentioned 40 estimation points was calculated to obtain a standard deviation of the ultraviolet light intensity ratio.

The obtained standard deviation was defined as a standard deviation reference value σs1. When the standard deviation of the ultraviolet light intensity ratio obtained in each of the plates 206-1 to 206-6 is smaller than the standard deviation reference value σs1, it can be considered that providing the plate 206 has reduced the standard deviation. Accordingly, using any flow straightening plate among the plates 206-1 to 206-6 that has a standard deviation of the ultraviolet light intensity ratio smaller than the standard deviation reference When, as illustrated in FIG. 38, the standard deviation of the ultraviolet light intensity ratio obtained regarding each of the plates 206-1 to 206-6 includes values of, for example, from about 0.15 to about 0.25, and the standard deviation reference value σs1 in this case is, for example, 0.2, it can be considered that using the plate 206-3 or 206-4 having a standard deviation smaller than the standard deviation reference value σs1 improves ultraviolet light irradiation efficiency.

In other words, in FIG. 38, when the "(aperture ratio of inner region)+(aperture ratio of outer region)" is in a range of about from 6.3 to 8.6 where the standard deviation of the ultraviolet light intensity ratio is below than the standard deviation reference value σs1, it can be considered to be an efficient flow straightening plate.

Accordingly, it is obviously preferable that when the flow straightening plate is divided into three regions being concentric circles and having an equal area, as illustrated in FIG. 11, the aperture ratio of the innermost area Ain is preferably from 6 times to 10 times, and more preferably from 6.3 to 8.6, with respect to the aperture ratio of the outermost area Aout.

[Verification of Range of Aperture Ratio]

Next, flow velocity simulation was performed using two plates 206-11 and 206-12 having different aperture ratios illustrated in FIG. 39. The flow velocity simulation was also performed on computer using the straight tube illustrated in FIG. 34A. Note that the tapered portion 222 was not provided.

Table 5 depicts results of the flow velocity simulation.

TABLE 5

|  | Flow straightening plate 206-11 | Flow straightening plate 206-12 |
|---|---|---|
| Aperture ratio | 9.4% | 16.6% |
| Number of holes | 151 | 265 |
| Pressure loss | 0.5 kPa | 0.2 kPa |
| Ratio | 2.6 | 1 |

The plate 206-11 had 151 holes and an aperture ratio of 9.4%. The plate 206-12 had 265 holes and an aperture ratio of 16.6%.

By the flow velocity simulation, pressure at each of the inflow-side end and the outflow-side end of the straight tube illustrated in FIG. 34A was calculated to obtain pressure loss.

As a result, as depicted in Table 5, pressure losses of the plates 206-11 and 206-12 were 0.5 kPa and 0.2 kPa, respectively. Thus, the pressure loss at the aperture ratio of 9.4% was 2.5 times that at the aperture ratio of 16.6%.

Table 5 indicates that it is preferable to set the aperture ratio to 10% or more to suppress the pressure loss to about 0.5 kPa.

Next, regarding plates 206-21 to 206-24 having different aperture ratios, safety factor was calculated. Table 6 depicts results of the calculation.

TABLE 6

|  | Flow straightening plate 206-21 | Flow straightening plate 206-22 | Flow straightening plate 206-23 | Flow straightening plate 206-24 |
|---|---|---|---|---|
| Number of holes | 349 | 487 | 649 | 806 |
| Aperture ratio | 22% | 30% | 41% | 50% |
| von Mises equivalent stress | 335 MPa | 365 MPa | 432 MPa | 467 MPa |
| Safety factor | 1.6 | 1.4 | 1.2 | 1.1 |

As the plates 206-21 to 206-24, stainless steel SUS 304 was used whose tensile strength was 520 MPa. The specifications of the plates 206-21 to 206-24 were as depicted in Table 6, in which aperture ratios of the plates 206-21, 206-22, 206-23, and 206-24 were 22%, 30%, 41%, and 50%, respectively.

As stress under a pressure of 3 MPa applied to each of the plates 206-21 to 206-24, von Mises equivalent stress was calculated, followed by calculation of safety factor (=(tensile strength)÷(von Mises equivalent stress)).

Figure 40:
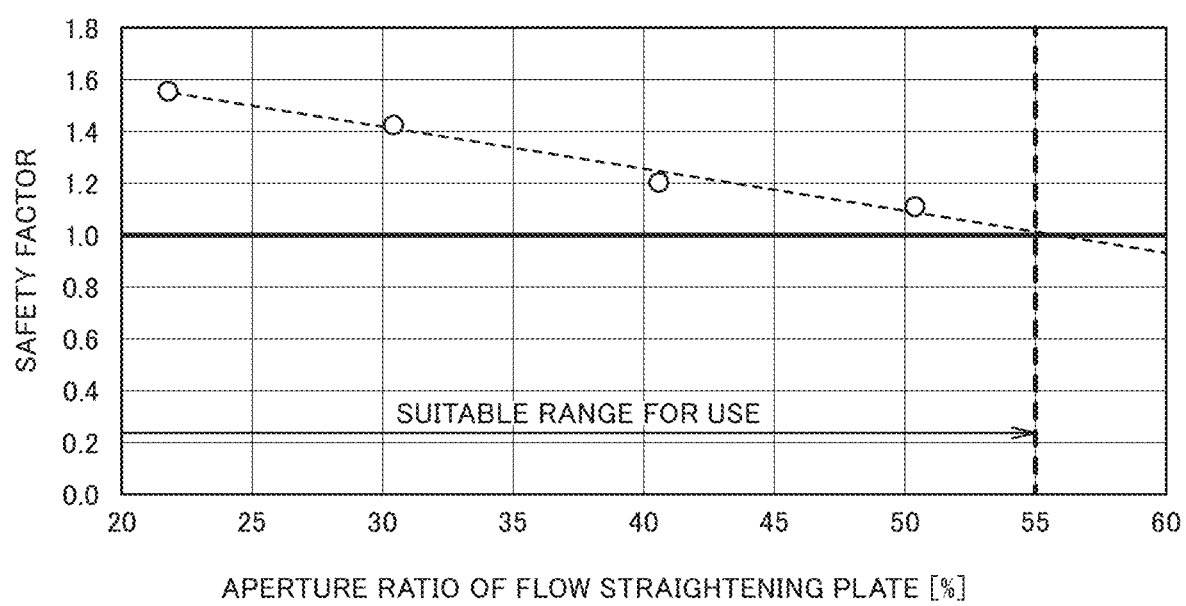
FIG. 40 illustrates one example of correspondences between aperture ratios of flow straightening plates and safety factors by flow velocity simulation using the fluid sterilization module according to the second embodiment.
Figure 42A:
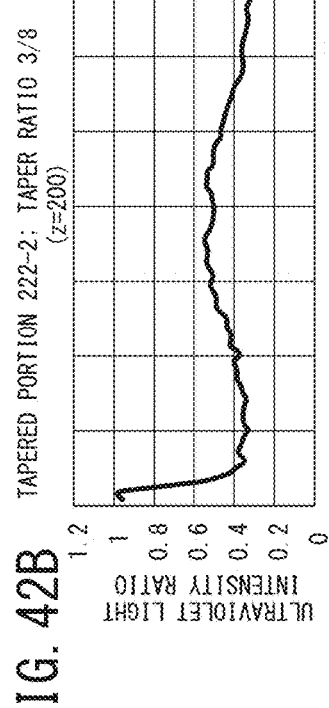
FIGS. 42A to 42E illustrate one example of correspondences between taper ratios and ultraviolet light intensity ratios by flow velocity simulation using the fluid sterilization module according to the second embodiment.
Figure 42B:
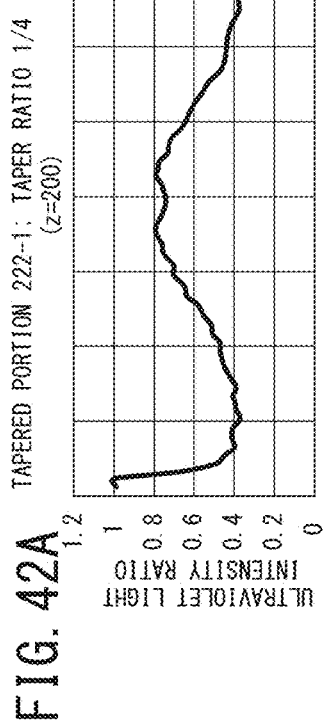
Figure 42C:
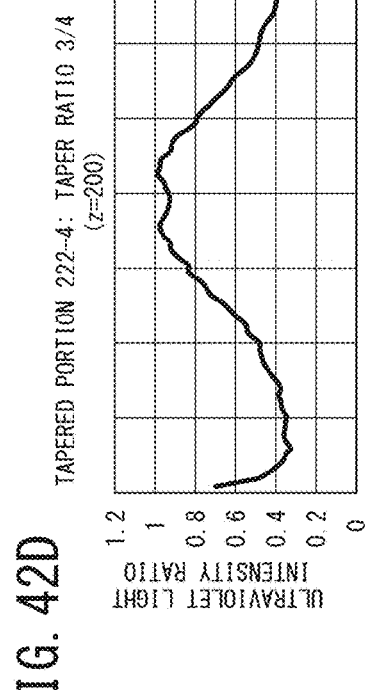
Figure 42D:
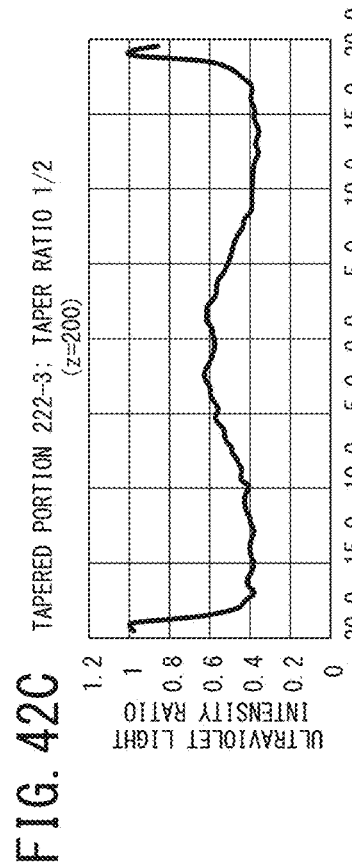
Figure 42E:
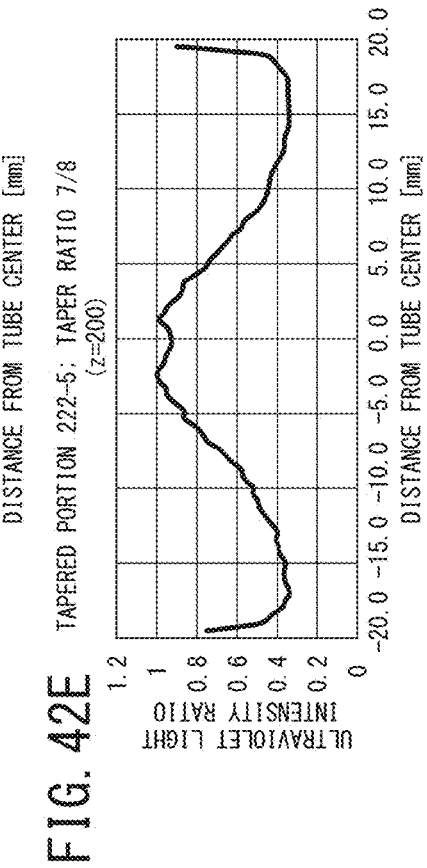

FIG. 40 illustrates a correspondence between the aperture ratio [%] of flow straightening plate and safety factor, in which the horizontal axis represents aperture ratio of flow straightening plate, and the vertical axis represents safety factor.

As illustrated in FIG. 40, the safety factor becomes lower as the aperture ratio becomes higher. Lower safety factors may result in breakage of the flow straightening plates, so that the safety factor is preferably "1" or more, and the aperture ratio is preferably 50% or less, since the safety factor becomes less than "1" at an aperture ratio of about 55%.

Thus, from the viewpoints of pressure loss and safety factor, it is obviously preferable that the aperture ratio is from 10% to 50%.

[Fluid Simulation (Tapered Shape)]

Next, using FIG. 34A, fluid simulation on computer was performed by providing the tapered portion 222. Note that the plate 206 was not provided.

As the tapered portion 222, tapered portions 222-1 to 222-5 were used, as illustrated in FIGS. 41A to 41E. Taper ratios of the tapered portions 222-1 to 222-5 were ¼, ⅜, ½, ¾, and ⅞, respectively. In the fluid simulation, conditions for allowing an object to flow were the same as those in the optical simulation.

Regarding the same 40 estimation points as those in the optical simulation, ultraviolet light intensity ratio was calculated. FIGS. 42A to 42E illustrate results of the calculation. In each of FIGS. 42A to 42E, the horizontal axis represents distance [mm] in the Y axis direction from the tube center (X=0, y=0, and Z=200) in the cross-section passing through Z=200 and X=0, and the vertical axis represents ultraviolet light intensity ratio.

FIG. 43 illustrates a correspondence between the standard deviation of ultraviolet light intensity ratio and tapered ratio regarding each of the tapered portions 222-1 to 222-5.

Herein, fluid simulation was performed without providing the tapered portion in the straight tube illustrated in FIG. 34A, and ultraviolet light intensity ratio regarding the above-mentioned 40 estimation points was calculated to obtain a standard deviation of the ultraviolet light intensity ratio. The obtained standard deviation was defined as a standard deviation reference value σs2. When the standard deviation of ultraviolet light intensity ratio obtained regarding each of the tapered portions 222-1 to 222-5 is smaller than the standard deviation reference value σs2, it can be considered that providing the tapered portion has reduced the standard deviation. Accordingly, using any one of the respective tapered portions 222-1 to 222-5 that has a standard deviation of the ultraviolet light intensity ratio smaller than the standard deviation reference value σs2 can be considered to have reduced variation in the ultraviolet light irradiation dose, thereby having improved efficiency. Conversely, in the case of a tapered portion having a standard deviation of the ultraviolet light intensity ratio equal to or more than the standard deviation reference value σs2, using the tapered portion can be considered to increase variation in the ultraviolet light irradiation dose, thereby degrading efficiency.

When, as illustrated in FIG. 43, the standard deviation of the ultraviolet light intensity ratio obtained regarding the respective tapered portions 222-1 to 222-5 includes values of, for example, from about 0.13 to about 0.23, and the standard deviation reference value σs2 in this case is, for example, 0.2, it can be considered that using the tapered portion 222-1, 222-2, or 222-3 having a standard deviation smaller than the standard deviation reference value σs2 improves ultraviolet light irradiation efficiency.

In other words, in FIG. 43, when the taper ratio is in a range of from 0.2 to 0.68 where the standard deviation of the ultraviolet light intensity ratio is below the standard deviation reference value σs2, it can be considered to be an efficient taper ratio.

Accordingly, it is obviously preferable that the taper ratio of the tapered portion 222 is from 0.2 to 0.68.

Example F

In the fluid sterilization module 1 according to the first embodiment, simulation was performed to describe a relationship between the cross-sectional area A26 of the first chamber 26 and the cross-sectional area A21 of the processing flow path 21d illustrated in FIG. 2B.

As illustrated in FIGS. 44A to 44C, using three fluid sterilization modules 1-1 to 1-3 different in an outer diameter φD1 of the inner cylinder 21, flow velocity at a communicating portion between the inflow portion 4 and the first chamber 26 was measured.

In each of the fluid sterilization modules 1-1 to 1-3, an inner diameter φd1 of the inner cylinder 21 was 020 mm, and an inner diameter φd2 of the case portion 22 was 034 mm. In addition, in the fluid sterilization module 1-1, the outer diameter φD1 of the inner cylinder 21 was 031 mm, and the ratio between the cross-sectional area A26 of the first chamber 26 and the cross-sectional area A21 of the processing flow path 21d (A26/A21) was 48.8%. In the fluid sterilization module 1-2, the outer diameter φD1 of the inner cylinder 21 was 028 mm, and the ratio between the cross-sectional area A26 of the first chamber 26 and the cross-sectional area A21 of the processing flow path 21d (A26/A21) was 93%. In the fluid sterilization module 1-3, the outer diameter φD1 of the inner cylinder 21 was φ26 mm, and the ratio between the cross-sectional area A26 of the first chamber 26 and the cross-sectional area A21 of the processing flow path 21d (A26/A21) was 120%.

FIGS. 44A to 44C illustrate flow velocity distributions in the flow paths of the respective fluid sterilization modules 1-1 to 1-3. Note that each FIGS. 44A to 44C simply illustrate the fluid sterilization module 1 illustrated in FIG. 2A.

In the fluid sterilization modules 1-1 and 1-2 having a cross-sectional ratio A26/A21 smaller than "1", a minimum value of flow velocity at a communication portion K between the inflow portion 4 and the first chamber 26 was larger than 1 m/sec, whereby it was confirmed that biofilm formation can be favorably suppressed.

On the other hand, the fluid sterilization module 1-3 having a cross-sectional ratio A26/A21 larger than "1" had a minimum value of flow velocity at the communication portion K between the inflow portion 4 and the first chamber 26 smaller than 1 m/sec, so that it was confirmed that biofilm formation may be unable to be suppressed.

Thus, it is obviously preferable that the ratio (A26/A21) between the cross-sectional area A26 of the first chamber 26 and the cross-sectional area A21 of the processing flow path 21d is smaller than "1" to suppress biofilm formation.

REFERENCE SIGNS LIST

1: Fluid sterilization module
2: Sterilization processing unit
3: Light emitting unit
4: Inflow portion
5: Outflow portion
21: Inner cylinder
21d: Processing flow path
22: Case portion
23: Plate (Flow straightening plate)
24: Member
26: First chamber
27: Second chamber
34: Light source
34a: Light emitting element
201: Fluid sterilization module
202: Inflow portion
203: Cylindrical portion
204: Light emitting unit
205: Outflow portion
206: Plate (Flow straightening plate)
221a: Inflow port
222: Tapered portion
234: Window portion
235: Inner flow path
241: Light source

The invention claimed is:

1. An ultraviolet light irradiation device comprising:
a cylindrical portion configured to form a cylindrical processing flow path extending in a longitudinal direction and include an opening at one end side of the cylindrical portion;
a case portion configured to house the cylindrical portion;
formed between the cylindrical portion and the case portion, a first chamber configured to cover the opening and communicate with the cylindrical processing flow path via the opening;
an inflow portion configured to allow an object to flow into the first chamber;
an outflow portion configured to allow the object having passed through the cylindrical processing flow path to flow out from an other end side of the cylindrical portion; and
a light emitting element provided at least on the one end side or the other end side of the cylindrical portion and configured to apply ultraviolet light to the object passing through the cylindrical processing flow path,
wherein:
the cylindrical processing flow path is a straight tube,
a static friction coefficient of an outer peripheral surface of the cylindrical portion is smaller than a static friction coefficient of an inner peripheral surface of the case portion,
the cylindrical portion is formed using an ultraviolet light reflecting material, and
the first chamber has an inner volume equal to or more than $2/3$ of the cube of an equivalent inner diameter of the cylindrical processing flow path and equal to or less than 3 times of inner volume of the cylindrical processing flow path.

2. The ultraviolet light irradiation device according to claim 1, wherein the first chamber is formed along an outer periphery of the cylindrical portion.

3. The ultraviolet light irradiation device according to claim 1, wherein an amount of change in a main cross-sectional area from a most upstream portion to a most downstream portion of the cylindrical processing flow path is 5% or less.

4. The ultraviolet light irradiation device according to claim 1, further comprising a plate configured to cover the opening at the one end side of the cylindrical portion, wherein the plate includes a plurality of opening holes penetrating between front and back surfaces of the plate, and has an aperture ratio of from 5% to 80%.

5. The ultraviolet light irradiation device according to claim 4, wherein the plurality of opening holes have an equivalent diameter equal to or more than 0.5 mm and equal to or less than $1/3$ of the equivalent inner diameter of the cylindrical processing flow path.

6. The ultraviolet light irradiation device according to claim 4, further comprising a protruding portion at a position facing the opening on a wall surface of the first chamber, wherein the plate is fixed by being sandwiched between the protruding portion and an end face of the cylindrical portion.

7. The ultraviolet light irradiation device according to claim 4, wherein the plate is circular in plan view, and the aperture ratio is set to be larger at positions closer to a center of the plate and smaller at positions closer to a periphery of the plate, and wherein the light emitting element is provided on the other end side of the cylindrical portion, and applies ultraviolet light to the object flowing through the cylindrical processing flow path, in which, in a cross-section of the cylindrical processing flow path orthogonal to the longitudinal direction, an intensity distribution of the ultraviolet light applied by the light emitting element has higher ultraviolet light intensity in a vicinity of a center than ultraviolet light intensity in a periphery of the center.

8. The ultraviolet light irradiation device according to claim 7, wherein when the plate is divided into three regions being concentric circles and having an equal area, the aperture ratio of an innermost region is from 6 times to 10 times with respect to the aperture ratio of an outermost region.

9. The ultraviolet light irradiation device according to claim 7, wherein the first chamber includes a tapered portion having an inner diameter gradually increasing along the longitudinal direction, and communicating with the cylindrical processing flow path, the inflow portion being provided at a small diameter side end of the tapered portion.

10. The ultraviolet light irradiation device according to claim 9, wherein the tapered portion has a tapered shape with a taper ratio of from 0.2 to 0.68.

11. The ultraviolet light irradiation device according to claim 4, wherein the aperture ratio of the plate is from 10% to 50%.

12. The ultraviolet light irradiation device according to claim 1, wherein the inflow portion is arranged at a position close to the other end side of the cylindrical portion by a distance equal to or more than an inflow port equivalent radius of the inflow portion and equal to or less than $2/3$ of a processing flow path length from an end on the one end side of the cylindrical portion.

13. The ultraviolet light irradiation device according to claim 1, further comprising a second chamber between the cylindrical processing flow path and the outflow portion.

14. The ultraviolet light irradiation device according to claim 13, wherein on the other end side of the cylindrical portion is provided a communication port configured to allow for communication between the cylindrical processing flow path and the second chamber, the second chamber being provided along an outer peripheral surface of the cylindrical portion.

15. The ultraviolet light irradiation device according to claim 14, wherein the outflow portion is arranged at a position close to the one end side of the cylindrical portion by a distance equal to or more than an outflow port equivalent radius of the outflow portion and equal to or less than $2/3$ of a length of the cylindrical processing flow path.

16. The ultraviolet light irradiation device according to claim 1, wherein on an end face on the other end side of the cylindrical portion is provided a component configured to cover an entire opening on the other end side of the cylindrical portion, the component being bonded to the end face on the other end side of the cylindrical portion via an elastic member.

17. The ultraviolet light irradiation device according to claim 1, wherein, in the cross-section orthogonal to the longitudinal direction at a position including the first chamber of the cylindrical portion, a cross-sectional area of the first chamber is from $1/10$ to 1 of a cross-sectional area of the cylindrical processing flow path.

18. The ultraviolet light irradiation device according to claim 1, wherein the ultraviolet light reflecting material from which the cylindrical portion is formed has a diffuse transmittance of from 1%/mm to 20%/mm and a total reflectance of from 80%/mm to 99%/mm in an ultraviolet light region.

19. The ultraviolet light irradiation device according to claim 1, wherein the inflow portion is formed using polyolefin.

20. The ultraviolet light irradiation device according to claim 1, wherein the ultraviolet light irradiation device is a fluid sterilization module configured to sterilize a fluid as the object.

* * * * *